United States Patent
Nebel et al.

(10) Patent No.: US 9,512,120 B2
(45) Date of Patent: Dec. 6, 2016

(54) MICROBICIDALLY ACTIVE IMIDAZOPYRIDINE DERIVATIVES

(71) Applicant: Syngenta Participations AG, Basel (CH)

(72) Inventors: Kurt Nebel, Stein (CH); Martin Pouliot, Stein (CH)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 14/771,572

(22) PCT Filed: Mar. 17, 2014

(86) PCT No.: PCT/EP2014/055292
§ 371 (c)(1),
(2) Date: Aug. 31, 2015

(87) PCT Pub. No.: WO2014/140365
PCT Pub. Date: Sep. 18, 2014

(65) Prior Publication Data
US 2016/0016949 A1    Jan. 21, 2016

(30) Foreign Application Priority Data
Mar. 15, 2013    (EP) ..................... 13159554

(51) Int. Cl.
*C07D 401/14* (2006.01)
*A61K 31/437* (2006.01)
*C07D 471/04* (2006.01)
*A01N 43/90* (2006.01)

(52) U.S. Cl.
CPC ............ *C07D 471/04* (2013.01); *A01N 43/90* (2013.01)

(58) Field of Classification Search
CPC ........................... C07D 401/14; A61K 31/437
USPC ......................................... 546/119; 514/303
See application file for complete search history.

(56) References Cited

U.S. PATENT DOCUMENTS

| | | | | |
|---|---|---|---|---|
| 4,281,005 A | * | 7/1981 | Baldwin | ............ C07D 471/04 514/341 |
| 2007/0066670 A1 | | 3/2007 | Eberle et al. | |

FOREIGN PATENT DOCUMENTS

| | | |
|---|---|---|
| EP | 0145340 A3 | 6/1985 |
| EP | 0646579 A1 | 4/1995 |
| WO | 03/011864 A1 | 2/2003 |
| WO | 2005/011700 A1 | 2/2005 |
| WO | 2005/051324 A2 | 6/2005 |
| WO | 2006/031878 A2 | 3/2006 |
| WO | 2009/000413 A1 | 12/2008 |
| WO | 2009/152584 A1 | 12/2009 |
| WO | 2011/038293 A1 | 3/2011 |

OTHER PUBLICATIONS

Yashioka H et al: New Synthetic route to Imidazo [4,5-C] Pyridines by the thermal electrocyclic reaction of 1-azahexatriene systems, Heterocycles: An International Journal for reviews and communications in Heterocyclic chemistry, vol. 41, No. 1, 1995, pp. 161-174.
Database Registry [online],Chemical Abstracts Service, Columbus, Ohio, US, Mar. 12, 2013, retrieved from STN Database accession No. 1423032-66-9, CAS Registry No. 1423032-66-9.
Database Registry [online],Chemical Abstracts Service, Columbus, Ohio, US, Apr. 21, 2011, retrieved from STN Database accession No. 1283176-16-8, CAS Registry No. 1283176-16-8.
Database Registry [online],Chemical Abstracts Service, Columbus, Ohio, US, Aug. 4, 2011, retrieved from STN Database accession No. 1314961-48-2, CAS Registry No. 1314961-48-2.
Database Registry [online],Chemical Abstracts Service, Columbus, Ohio, US, Jun. 15, 2012, retrieved from STN Database accession No. 1378819-14-7, CAS Registry No. 1378819-14-7.
Database Registry [online],Chemical Abstracts Service, Columbus, Ohio, US, Apr. 16, 2012, retrieved from STN Database accession No. 1369348-04-8, CAS Registry No. 1369348-04-8.

\* cited by examiner

*Primary Examiner* — Niloofar Rahmani
(74) *Attorney, Agent, or Firm* — R. Kody Jones

(57) ABSTRACT

The present invention provides compounds of formula (I) wherein $Y^1$, $Y^2$, $Y^3$, G, $V^1$, $V^2$, $V^3$ and $V^4$ are as defined in the claims. The invention further relates to compositions which comprise these compounds and to their use in agriculture or horticulture for controlling or preventing infestation of plants by phytopathogenic microorganisms, preferably fungi.

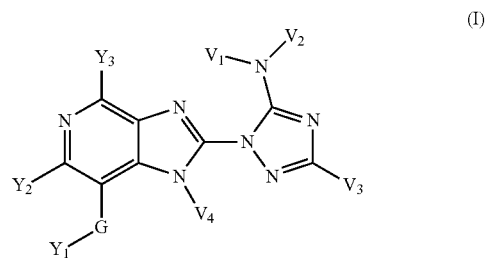

(I)

18 Claims, No Drawings

MICROBICIDALLY ACTIVE IMIDAZOPYRIDINE DERIVATIVES

RELATED APPLICATION INFORMATION

This application is a 371 of International Application No. PCT/EP2014/055292, filed 17 Mar. 2014, which claims priority to EP Patent Application No. 13159554.8, filed 15 Mar. 2013, the contents of which are incorporated by reference herein.

The present invention relates to novel microbiocidally active, in particular fungicidally active, imidazopyridine derivatives. It further relates to intermediates used in the preparation of these compounds, to compositions which comprise these compounds and to their use in agriculture or horticulture for controlling or preventing infestation of plants by phytopathogenic microorganisms, preferably fungi.

The application WO2009000413 is in the pharmaceutical field and is related to substituted benzoimidazoles, their preparation and their use for inducing apoptosis.

Surprisingly, it has been found that novel compounds have microbiocidal activity.

The present invention accordingly relates to oxime derivatives of formula (I)

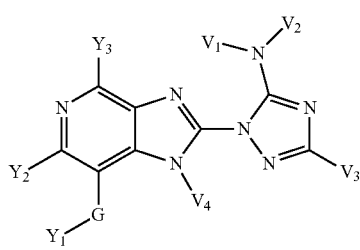

wherein $Y_1$ represents hydrogen, halogen, CN, $NO_2$, $C_1$-$C_6$ alkyl, $C_3$-$C_8$ cycloalkyl, $C_3$-$C_8$ cycloalkenyl, $C_2$-$C_6$ alkenyl, $C_2$-$C_6$ alkynyl, phenyl, naphthyl, a 5- to 10-membered mono- or bicyclic heterocycle containing one to three heteroatoms independently selected from O, S and N, providing that the heterocycle does not contain adjacent oxygen atoms, adjacent sulphur atoms, or adjacent sulphur and oxygen atoms, wherein the heterocycle can be aromatic, or fully or partially saturated, $OR^1$, $CO_2R^1$, $COR^2$, $CON(R^3)_2$, $N(R^3)_2$, $NR^3COR^2$ and $C(R^2)\!\!=\!\!N\!\!-\!\!OR^1$, wherein the alkyl, cycloalkyl, cycloalkenyl, alkenyl, alkynyl, phenyl, naphthyl, and heterocycle are optionally substituted by one or more groups independently selected from halogen, CN, OH, $NH_2$, $NR^3COR^2$, SH, $NO_2$, $OR^1$, $C_1$-$C_4$ alkyl, $C_1$-$C_4$ haloalkyl, phenyl, halophenyl, $C_1$-$C_4$ alkylphenyl, $C_3$-$C_8$ cycloalkyl, $C_3$-$C_8$ cycloalkenyl, $C_1$-$C_4$ alkylthio, $C_1$-$C_4$ alkylsulphinyl and $C_1$-$C_4$ alkylsulphonyl;

$Y_2$ and $Y_3$ are independently selected from hydrogen, halogen, CN, $NO_2$, $C_1$-$C_8$ alkyl, $C_3$-$C_8$ cycloalkyl, $C_3$-$C_8$ cycloalkenyl, $C_2$-$C_8$ alkenyl, $C_2$-$C_8$ alkynyl, phenyl, phenyl-$C_1$-$C_6$-alkyl, a 5- or 6-membered heterocycle containing one to three heteroatoms independently selected from O, S and N, providing that the heterocycle does not contain adjacent oxygen atoms, adjacent sulphur atoms, or adjacent sulphur and oxygen atoms, $OR^1$, $COR^2$, SH, $C_1$-$C_8$ alkylthio, $C_1$-$C_8$ alkylsulphinyl, $C_1$-$C_8$ alkylsulphonyl, phenylthio, phenylsulphinyl, phenylsulphonyl, $N(R^3)_2$, $CO_2R^1$, $O(CO)R^2$, $CON(R^3)_2$, $NR^3COR^2$ and $C(R^2)\!\!=\!\!N\!\!-\!\!OR^1$, wherein the alkyl, cycloalkyl, cycloalkenyl, alkenyl, alkynyl, phenyl, benzyl, and heterocycle are optionally substituted by one or more groups independently selected from halogen, CN, OH, $NH_2$, SH, $NO_2$, $OR^1$, $C_1$-$C_4$ alkyl, $C_1$-$C_4$ haloalkyl, $C_1$-$C_4$ alkylthio, $C_1$-$C_4$ alkylsulphinyl and $C_1$-$C_4$ alkylsulphonyl;

or $Y_3$ is defined as above and $Y_1$ and $Y_2$ together with the fragment of the compound to which they are attached form a partially or fully unsaturated 5- to 7-membered carbocyclic ring or a partially or fully unsaturated 5- to 7-membered heterocyclic ring containing one to three heteroatoms independently selected from O, S, N and $N(R^3)$, providing that the heterocycle does not contain adjacent oxygen atoms, adjacent sulphur atoms, or adjacent sulphur and oxygen atoms, and wherein the ring formed by $Y_1$ and $Y_2$ is optionally substituted by one or more groups independently selected from halogen, CN, $NH_2$, $NO_2$, OH, SH, $C_1$-$C_4$ alkyl, $C_1$-$C_4$ haloalkyl, $C_1$-$C_4$ alkoxy and $C_1$-$C_4$ haloalkoxy;

G represents a direct bond, O, S, S(O), $SO_2$, C(O), $CO_2$, $C(R^4)(R^5)$, $C(R^4)(R^5)\!\!-\!\!C(R^6)(R^7)$, $C(R^4)\!\!=\!\!C(R^5)$, C≡C, $O\!\!-\!\!C(R^4)(R^5)$, $S\!\!-\!\!C(R^4)(R^5)$, $C(R^4)(R^5)\!\!-\!\!O$, $C(R^4)(R^5)\!\!-\!\!S$ or phenyl;

each $R^1$ is independently selected from hydrogen, $C_1$-$C_8$ alkyl, $C_3$-$C_8$ cycloalkyl, $C_3$-$C_8$ cycloalkyl-$C_1$-$C_2$ alkyl, $C_3$-$C_8$ cycloalkenyl, $C_3$-$C_8$ alkenyl, $C_3$-$C_8$ alkynyl, phenyl, benzyl or a 5- or 6-membered heterocycle containing one to three heteroatoms independently selected from O, S, N and $N(R^3)$, providing that the heterocycle does not contain adjacent oxygen atoms, adjacent sulphur atoms, or adjacent sulphur and oxygen atoms, wherein the alkyl, cycloalkyl, cycloalkenyl, alkenyl, alkynyl, phenyl, benzyl and heterocycle are optionally substituted by one or more groups independently selected from halogen, CN, OH, $NH_2$, $NO_2$, SH, $C_1$-$C_4$ alkyl, $C_1$-$C_4$ haloalkyl, $C_1$-$C_4$ alkoxy, $C_1$-$C_4$ haloalkoxy, $C_1$-$C_4$-alkoxy-$C_1$-$C_4$-alkyl and $C_1$-$C_4$ alkoxycarbonyl, and wherein the heterocycle may be attached to the rest of the molecule via a $C_1$-$C_2$ alkylene moeity;

each $R^2$ is independently selected from hydrogen, $C_1$-$C_8$ alkyl, $C_3$-$C_8$ cycloalkyl, $C_3$-$C_8$ cycloalkenyl, $C_2$-$C_8$ alkenyl, $C_2$-$C_8$ alkynyl, phenyl, benzyl and pyridyl, wherein the alkyl, cycloalkyl, cycloalkenyl, alkenyl, alkynyl, phenyl, benzyl and pyridyl groups are optionally substituted by one or more groups independently selected from halogen, CN, $NH_2$, $NO_2$, OH, $C_1$-$C_4$ alkyl, $C_1$-$C_4$ haloalkyl, $C_1$-$C_4$ alkoxy, $C_1$-$C_4$ alkylthio and $C_1$-$C_4$ haloalkoxy;

each $R^3$ is independently selected from hydrogen, $C_1$-$C_8$ alkyl, $C_3$-$C_8$ alkenyl, $C_3$-$C_8$ cycloalkyl, $C_3$-$C_8$ cycloalkenyl, $C_3$-$C_8$ alkynyl, phenyl, benzyl, CN, $OR^1$, $COR^2$, $C_1$-$C_8$ alkylsulphonyl, and a 5- or 6-membered heterocycle containing one to three heteroatoms independently selected from O, S, N and $N(R^8)$, providing that the heterocycle does not contain adjacent oxygen atoms, adjacent sulphur atoms, or adjacent sulphur and oxygen atoms, wherein the alkyl, cycloalkyl, cycloalkenyl, alkenyl, alkynyl, phenyl, benzyl and heterocycle are optionally substituted by one or more groups independently selected from halogen, CN, $NH_2$, $NO_2$, OH, $C_1$-$C_4$ alkyl, $C_1$-$C_4$-haloalkyl, $C_1$-$C_4$ alkoxy, $C_1$-$C_4$ haloalkoxy and $C_1$-$C_4$-alkoxy-$C_1$-$C_4$-alkyl;

wherein when two radicals $R^3$ are attached to the same nitrogen atom, these radicals can be identical or different;

wherein when two radicals $R^3$ are attached to the same nitrogen atom, both of these radicals cannot be $OR^1$;

and wherein when two radicals $R^3$ are attached to the same nitrogen atom, these two radicals together with the nitrogen atom to which they are attached may form a cycle selected from B-1, B-2, B-3, B-4, B-5, B-6, B-7 and B-8:

may form a 3- to 6-membered carbocycle or heterocycle containing one to three heteroatoms independently selected from O, S, N and N(R$^8$), providing that the heterocycle does not contain adjacent oxygen atoms, adjacent sulphur atoms, or adjacent sulphur and oxygen atoms, wherein carbocycle and heterocycle are optionally substituted by one or more groups independently selected from halogen, CN, NH$_2$, NO$_2$, OH, C$_1$-C$_4$ alkyl, C$_1$-C$_4$-haloalkyl, C$_1$-C$_4$ alkoxy, C$_1$-C$_4$ haloalkoxy and C$_1$-C$_4$-alkoxy-C$_1$-C$_4$-alkyl;

R$^8$ represents hydrogen, C$_1$-C$_8$ alkyl, C$_1$-C$_8$ haloalkyl, C$_3$-C$_8$ cycloalkyl, C$_3$-C$_8$ alkenyl, C$_3$-C$_8$ alkynyl or C$_1$-C$_8$ alkoxy-C$_1$-C$_8$ alkyl;

V$_1$ and V$_2$ independently of one another represent hydrogen, C$_1$-C$_8$ alkyl, C$_3$-C$_8$ alkenyl, C$_3$-C$_8$ cycloalkyl, C$_3$-C$_8$ cycloalkenyl, C$_3$-C$_8$ alkynyl, benzyl, C$_2$-C$_9$ alkoxycarbonyl, C$_4$-C$_9$ alkenyloxycarbonyl, benzyloxycarbonyl or COR$^2$, wherein the alkyl, alkenyl, alkynyl, cycloalkyl, cycloalkenyl and benzyl are optionally substituted by one or more groups independently selected from halogen, CN, OH, C$_1$-C$_4$ alkyl, C$_1$-C$_4$ haloalkyl, C$_1$-C$_4$ alkoxy or C$_1$-C$_4$ haloalkoxy;

and wherein V$_1$ and V$_2$ together with the nitrogen atom to which they are attached may form a cycle selected from B-9, B-10, B-11, B-12 and B-13:

wherein the cycle so formed is optionally substituted by one or more groups independently selected from halogen, CN, NH$_2$, OH, C$_1$-C$_4$ alkyl, C$_1$-C$_4$ haloalkyl, C$_1$-C$_4$ alkoxy and C$_1$-C$_4$ haloalkoxy;

V$_3$ is selected from hydrogen, halogen, CN, NO$_2$, C$_1$-C$_8$ alkyl, C$_3$-C$_8$ cycloalkyl, C$_3$-C$_8$ cycloalkenyl, C$_2$-C$_8$ alkenyl, wherein the cycle formed is optionally substituted by one or more groups independently selected from halogen, CN, NH$_2$, NO$_2$, OH, C$_1$-C$_4$ alkyl, C$_1$-C$_4$ haloalkyl, C$_1$-C$_4$ alkoxy and C$_1$-C$_4$ haloalkoxy;

R$^4$, R$^5$, R$^6$ and R$^7$ independently of one another represent hydrogen, halogen, cyano, C$_1$-C$_4$ alkyl, C$_1$-C$_4$ alkoxy, C$_3$-C$_5$ cycloalkyl, C$_1$-C$_4$ haloalkyl, or C$_1$-C$_4$ alkylthio;

wherein two radicals R$^4$ and R$^5$ or R$^6$ and R$^7$ or R$^4$ and R$^6$ together with the carbon atom to which they are attached $C_2$-$C_8$ alkynyl, phenyl, benzyl, a 5- or 6-membered heterocycle containing one to three heteroatoms independently selected from O, S, N and $N(R^3)$, providing that the heterocycle does not contain adjacent oxygen atoms, adjacent sulphur atoms, or adjacent sulphur and oxygen atoms, $OR^1$, $COR^2$, SH, $C_1$-$C_8$ alkylthio, $C_1$-$C_8$ alkylsulphinyl, $C_1$-$C_8$ alkylsulphonyl, phenylthio, phenylsulphinyl, phenylsulphonyl, $N(R^3)_2$, $CO_2R^1$, $O(CO)R^2$, $CON(R^3)_2$, $NR^3COR^2$ and $C(R^2)=N-OR^1$, wherein the alkyl, cycloalkyl, cycloalkenyl, alkenyl, alkynyl, phenyl, benzyl, and heterocycle are optionally substituted by one or more groups independently selected from halogen, CN, $NH_2$, SH, $NO_2$, $OR^1$, $C_1$-$C_4$ alkyl and $C_1$-$C_4$ haloalkyl;

$V_4$ is selected from hydrogen, OH, $C_1$-$C_8$ alkyl, $C_1$-$C_8$ alkoxy, $C_3$-$C_8$ alkenyl, $C_3$-$C_8$ alkenyloxy, $C_3$-$C_8$ cycloalkyl, $C_3$-$C_8$ cycloalkenyl, $C_3$-$C_8$ cycloalkoxy, $C_3$-$C_8$ alkynyl, $C_3$-$C_8$ alkynyloxy, phenyl, phenyl-$C_1$-$C_6$-alkyl, benzyloxy, pyridyl, pyridyl-$C_1$-$C_6$-alkyl, $COR^2$, $CO_2R^2$, $CON(R^3)_2$ and $SO_2$—$C_1$-$C_8$-alkyl, wherein the alkyl, alkenyl, alkynyl, cycloalkyl, cycloalkenyl, phenyl, benzyl and pyridyl are optionally substituted by one or more groups independently selected from halogen, CN, $NH_2$, $NO_2$, OH, $C_1$-$C_4$ alkyl, $C_1$-$C_4$ haloalkyl, $C_1$-$C_4$ alkoxy and $C_1$-$C_4$ haloalkoxy;

or agriculturally acceptable tautomers, salts or N-oxides thereof.

Halogen, either as a lone substituent or in combination with another substituent (e.g. haloalkyl) is generally fluorine, chlorine, bromine or iodine, and usually fluorine, chlorine or bromine.

Each alkyl moiety (including the alkyl moiety of alkoxy, alkylthio, etc.) is a straight or branched chain and, depending on the number of carbon atoms it contains, is, for example, methyl, ethyl, n-propyl, n-butyl, n-pentyl, n-hexyl, isopropyl, sec-butyl, iso-butyl, tert-butyl, neo-pentyl, n-heptyl or 1,3-dimethylbutyl, and usually methyl or ethyl.

The alkenyl and alkynyl groups can be mono- or di-unsaturated and examples thereof are derived from the above mentioned alkyl groups.

The alkenyl group is an unsaturated straight or branched chain having a carbon-carbon double bond and, depending on the number of carbon atoms it contains, is, for example ethenyl, 1-propenyl, 2-propenyl, 1-methyl-ethenyl, 1-butenyl, 2-butenyl, 3-butenyl, 1-methyl-1-propenyl, 2-methyl-1-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, and usually 2-propenyl, 1-methyl-2-propenyl, 2-butenyl, 2-methyl-2-propenyl.

The alkynyl group is an unsaturated straight or branched chain having a carbon-carbon triple bond and, depending on the number of carbon atoms it contains, is, for example ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 3-methyl-1-butynyl, 1-methyl-2-butynyl, 1-methyl-3-butynyl, 2-methyl-3-butynyl, 1,1-dimethyl-2-propynyl, 1-ethyl-2-propynyl, 1-hexynyl, 2-hexynyl, 3-hexynyl, 4-hexynyl, 5-hexynyl, 3-methyl-1-pentynyl, 4-methyl-1-pentynyl, 1-methyl-2-pentynyl, 4-methyl-2-pentynyl, 1-methyl-3-pentynyl, 2-methyl-3-pentynyl, 1-methyl-4-pentynyl, 2-methyl-4-pentynyl, 3-methyl-4-pentynyl, 3,3,-dimethyl-1-butynyl, 1-ethyl-2-butynyl, 1,1-dimethyl-2-butynyl, 1-ethyl-3-butynyl, 2-ethyl-3-butynyl, 1,1-dimethyl-3-butynyl, 2,2-dimethyl-3-butynyl, 1,2-dimethyl-3-butynyl.

Haloalkyl moieties are alkyl moieties which are substituted by one or more of the same or different halogen atoms and are, for example, monofluoromethyl, difluoromethyl, trifluoromethyl, monochloromethyl, dichloromethyl, trichloromethyl, 2,2,2-trifluoroethyl, 2,2-difluoroethyl, 2-fluoroethyl, 1,1-difluoroethyl, 1-fluoroethyl, 2-chloroethyl, pentafluoroethyl, 1,1-difluoro-2,2,2-trichloroethyl, 2,2,3,3-tetrafluoroethyl and 2,2,2-trichloroethyl, and typically trichloromethyl, difluorochloromethyl, difluoromethyl, trifluoromethyl and dichlorofluoromethyl.

Alkoxy is, for example, methoxy, ethoxy, propoxy, isopropoxy, n-butoxy, iso-butoxy, sec-butoxy and tert-butoxy, and usually methoxy or ethoxy.

Haloalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy and 2,2,2-trichloroethoxy, and usually difluoromethoxy, 2-chloroethoxy and trifluoromethoxy.

Alkylthio is, for example, methylthio, ethylthio, propylthio, iso-propylthio, n-butylthio, iso-butylthio, sec-butylthio or tert-butylthio, and usually methylthio or ethylthio.

Alkylsulphonyl is, for example, methylsulphonyl, ethylsulphonyl, propylsulphonyl, iso-propylsulphonyl, n-butylsulphonyl, iso-butylsulphonyl, sec-butylsulphonyl or tert-butylsulphonyl, and usually methylsulphonyl or ethylsulphonyl.

Alkylsulphinyl is, for example, methylsulphinyl, ethylsulphinyl, propylsulphinyl, iso-propylsulphinyl, n-butylsulphinyl, iso-butylsulphinyl, sec-butylsulphinyl or tert-butylsulphinyl, and usually methylsulphinyl or ethylsulphinyl.

Cycloalkyl may be saturated or partially unsaturated, preferably fully saturated, and is, for example, cyclopropyl, cyclobutyl, cyclopentyl or cyclohexyl.

Alkoxyalkyl is, for example, methoxymethyl, methoxyethyl, ethoxymethyl, ethoxyethyl, n-propoxymethyl, n-propoxyethyl, iso-propoxymethyl or iso-propoxyethyl.

Aryl includes phenyl, naphthyl, anthracyl, fluorenyl and indanyl, but is usually phenyl.

Carbocycle includes cycloalkyl groups and aryl groups.

Heterocycloalkyl is a non-aromatic ring that may be saturated or partially unsaturated, preferably fully saturated, containing carbon atoms as ring members and at least one heteroatom selected from O, S and N as ring members. Examples include oxiranyl, oxetanyl, tetrahydrofuranyl, tetrahydropyranyl, 1,3-dioxolanyl, 1,4-dioxanyl, aziridinyl, azetidinyl, pyrrolidinyl, piperidinyl, oxazinanyl, morpholinyl, thiomorpholinyl, imidazolidinyl, pyrazolidinyl and piperazinyl, preferably morpholinyl, pyrrolidinyl, piperdinyl and piperazinyl, more preferably morpholinyl and pyrollidinyl.

Heteroaryl is, for example, a monovalent monocyclic or bicyclic aromatic hydrocarbon radical. Examples of monocyclic groups include pyridyl, pyridazinyl, pyrimidinyl, pyrazinyl, pyrrolyl, pyrazolyl, imidazolyl, triazolyl, tetrazolyl, furanyl, thiophenyl, oxazolyl, isoxazolyl, oxadiazolyl, thiazolyl, isothiazolyl, and thiadiazolyl. Examples of bicyclic groups include quinolinyl, cinnolinyl, quinoxalinyl, benzimidazolyl, benzothiophenyl, and benzothiadiazolyl. Monocyclic heteroaryl groups are preferred, preferably pyridyl, pyrrolyl, imidazolyl and triazolyl, e.g. 1,2,4 triazolyl, pyridyl and imidazolyl being most preferred.

The terms "heterocycle" and "heterocyclic ring" are used interchangeably and are defined to include heterocycloalkyl and heteroaryl groups. Any reference herein to a heterocycle or heterocyclic ring preferably refers to the specific examples given under the definition of heteroaryl and heterocycloalkyl above, and are preferably morpholinyl, pyrrolidinyl, piperdinyl, piperazinyl pyridyl, pyrrolyl, imidazolyl and triazolyl, e.g. 1,2,4 triazolyl, more preferably morpholinyl, pyrollidinyl, pyridyl and imidazolyl. No heterocycle contains adjacent oxygen atoms, adjacent sulphur atoms, or adjacent oxygen and sulphur atoms.

Where a moiety is indicated as being (optionally) substituted, e.g. alkyl, this includes those moieties where they are part of a larger group, e.g. the alkyl in the alkylthio group. The same applies, e.g. to the phenyl moiety in phenylthio etc. Where a moiety is indicated as being optionally substituted by one or more other groups, preferably there are one to five optional substituents, more preferably one to three optional substituents. Where a moiety is substituted by a cyclic group, e.g. aryl, heteroaryl, cycloalkyl, preferably there are no more than two such substituents, more preferably no more than one such substituent.

The following substituents definitions, including preferred definitions, may be combined in any combination:

$Y_1$ represents hydrogen, halogen, CN, $NO_2$, $C_1$-$C_6$ alkyl, $C_3$-$C_8$ cycloalkyl, $C_3$-$C_8$ cycloalkenyl, $C_2$-$C_6$ alkenyl, $C_2$-$C_6$ alkynyl, phenyl, naphthyl, a 5- to 10-membered mono- or bicyclic heterocycle containing one to three heteroatoms independently selected from O, S and N, providing that the heterocycle does not contain adjacent oxygen atoms, adjacent sulphur atoms, or adjacent sulphur and oxygen atoms, wherein the heterocycle can be aromatic, or fully or partially saturated, $OR^1$, $CO_2R^1$, $COR^2$, $CON(R^3)_2$, $N(R^3)_2$, $NR^3COR^2$ and $C(R^2)$=N—$OR^1$, wherein the alkyl, cycloalkyl, cycloalkenyl, alkenyl, alkynyl, phenyl, naphthyl, and heterocycle are optionally substituted by one or more groups independently selected from halogen, CN, OH, $NH_2$, $NR^3COR^2$, SH, $NO_2$, $OR^1$, $C_1$-$C_4$ alkyl, $C_1$-$C_4$ haloalkyl, phenyl, halophenyl, $C_1$-$C_4$ alkylphenyl, $C_3$-$C_8$ cycloalkyl, $C_3$-$C_8$ cycloalkenyl, $C_1$-$C_4$ alkylthio, $C_1$-$C_4$ alkylsulphinyl and $C_1$-$C_4$ alkylsulphonyl.

Preferably, $Y_1$ represents hydrogen, halogen, CN, $C_1$-$C_6$ alkyl, $C_3$-$C_8$ cycloalkenyl, $C_2$-$C_6$ alkenyl, $C_2$-$C_6$ alkynyl, phenyl, a 5- to 10-membered mono- or bicyclic heterocycle containing one or two heteroatoms independently selected from O, S and N, providing that the heterocycle does not contain adjacent oxygen atoms, adjacent sulphur atoms, or adjacent sulphur and oxygen atoms, wherein the heterocycle can be aromatic, or fully or partially saturated, $C_1$-$C_4$ alkoxy, $C_1$-$C_4$ alkoxycarbonyl, $C_1$-$C_4$ alkylcarbonyl, $C_1$-$C_4$ alkenylcarbonyl and $C(R^2)$=N—$OR^1$, wherein the alkyl, cycloalkenyl, alkenyl, alkynyl, phenyl, benzyl and heterocycle are optionally substituted by one or more groups independently selected from halogen, $NH_2$, $NHCO(C_1$-$C_4$ alkyl), $C_1$-$C_4$ alkoxy, $C_1$-$C_4$ alkyl, $C_1$-$C_4$ haloalkyl, phenyl, halophenyl, $C_1$-$C_4$ alkylphenyl and $C_3$-$C_6$ cycloalkyl.

More preferably, $Y_1$ represents hydrogen, halogen, CN, $C_1$-$C_6$ alkyl, $C_3$-$C_8$ cycloalkenyl, $C_2$-$C_6$ alkenyl, $C_2$-$C_6$ alkynyl, phenyl, a 5- to 10-membered mono- or bicyclic heterocycle containing one or two heteroatoms independently selected from O, S and N, providing that the heterocycle does not contain adjacent oxygen atoms, adjacent sulphur atoms, or adjacent sulphur and oxygen atoms, wherein the heterocycle can be aromatic, or fully or partially saturated, $C_1$-$C_4$ alkoxy, $C_1$-$C_4$ alkoxycarbonyl, $C_1$-$C_4$ alkenylcarbonyl and $C(R^2)$=N—$OR^1$, wherein the alkyl, cycloalkenyl, alkenyl, alkynyl, phenyl, benzyl and heterocycle are optionally substituted by one or more groups independently selected from halogen, $NH_2$, $NHCO(C_1$-$C_4$ alkyl), $C_1$-$C_4$ alkoxy, $C_1$-$C_4$ alkyl, $C_1$-$C_4$ haloalkyl, phenyl, halophenyl, $C_1$-$C_4$ alkylphenyl and $C_3$-$C_6$ cycloalkyl.

In another group of compounds, $Y_1$ represents hydrogen, halogen, CN, $NO_2$, $C_1$-$C_6$ alkyl, $C_3$-$C_8$ cycloalkyl, $C_3$-$C_8$ cycloalkenyl, $C_2$-$C_6$ alkenyl, $C_2$-$C_6$ alkynyl, phenyl, naphthyl, a 5- to 10-membered mono- or bicyclic heterocycle containing one to three heteroatoms independently selected from O, S and N, providing that the heterocycle does not contain adjacent oxygen atoms, adjacent sulphur atoms, or adjacent sulphur and oxygen atoms, wherein the heterocycle can be aromatic, or fully or partially saturated, $CO_2R^1$, $COR^2$, $CON(R^3)_2$, $N(R^3)_2$, $NR^3COR^2$ and $C(R^2)$=N—$OR^1$, wherein the alkyl, cycloalkyl, cycloalkenyl, alkenyl, alkynyl, phenyl, naphthyl, and heterocycle are optionally substituted by one or more groups independently selected from halogen, CN, OH, $NH_2$, SH, $NO_2$, $OR^1$, $C_1$-$C_4$ alkyl, $C_1$-$C_4$ haloalkyl, $C_1$-$C_4$ alkylthio, $C_1$-$C_4$ alkylsulphinyl and $C_1$-$C_4$ alkylsulphonyl.

Preferably in this group of compounds, $Y_1$ represents hydrogen, halogen, CN, $NO_2$, $C_1$-$C_6$ alkyl, $C_3$-$C_8$ cycloalkyl, $C_2$-$C_6$ alkenyl, phenyl, naphthyl, a 5- to 10-membered mono- or bicyclic heterocycle containing one to three heteroatoms independently selected from O, S and N, providing that the heterocycle does not contain adjacent oxygen atoms, adjacent sulphur atoms, or adjacent sulphur and oxygen atoms, wherein the heterocycle can be aromatic, or fully or partially saturated, $CO_2R^1$, $COR^2$, $N(R^3)_2$ and $C(R^2)$=N—$OR^1$, wherein the alkyl, cycloalkyl, alkenyl, phenyl, naphthyl and heterocycle are optionally substituted by one or more groups independently selected from halogen, CN, OH, $NH_2$, SH, $NO_2$, $OR^1$, $C_1$-$C_4$ alkyl, $C_1$-$C_4$ haloalkyl, $C_1$-$C_4$ alkylthio, $C_1$-$C_4$ alkylsulphinyl and $C_1$-$C_4$ alkylsulphonyl.

More preferably in this group of compounds, $Y_1$ represents hydrogen, halogen, CN, $NO_2$, $C_1$-$C_4$ alkyl, $C_3$-$C_8$ cycloalkyl, $C_2$-$C_6$ alkenyl, phenyl, naphthyl, a 5- to 10-membered mono- or bicyclic heterocycle containing one to three heteroatoms independently selected from O, S and N, providing that the heterocycle does not contain adjacent oxygen atoms, adjacent sulphur atoms, or adjacent sulphur and oxygen atoms, wherein the heterocycle can be aromatic, or fully or partially saturated, $CO_2H$, $C_1$-$C_4$ alkoxycarbonyl, $C_1$-$C_4$ alkylcarbonyl, $NH_2$, $NH(C_1$-$C_4$ alkyl) and $N(C_1$-$C_4$ alkyl)$_2$, wherein the alkyl, cycloalkyl, alkenyl, phenyl, naphthyl and heterocycle are optionally substituted by one or more groups independently selected from halogen, CN, OH, $NH_2$, SH, $NO_2$, $C_1$-$C_4$ alkoxy, $C_1$-$C_4$ alkyl and $C_1$-$C_4$ haloalkyl.

In another group of compounds, $Y_1$ represents hydrogen, halogen, CN, $NO_2$, $C_1$-$C_6$ alkyl, $C_3$-$C_8$ cycloalkyl, $C_3$-$C_8$ cycloalkenyl, $C_2$-$C_6$ alkenyl, $C_2$-$C_6$ alkynyl, phenyl, naphthyl, a 5- to 10-membered mono- or bicyclic heterocycle containing one to three heteroatoms independently selected from O, S and N, providing that the heterocycle does not contain adjacent oxygen atoms, adjacent sulphur atoms, or adjacent sulphur and oxygen atoms, wherein the heterocycle can be aromatic, or fully or partially saturated, $CO_2R^1$, $COR^2$, $CON(R^3)_2$, $N(R^3)_2$, $NR^3COR^2$ and $C(R^2)$=N—$OR^1$, wherein the alkyl, cycloalkyl, cycloalkenyl, alkenyl, alkynyl, phenyl, naphthyl, and heterocycle are optionally substituted by one or more groups independently selected from halogen, CN, OH, $NH_2$, SH, $NO_2$, $OR^1$, $C_1$-$C_4$ alkyl, $C_1$-$C_4$ haloalkyl, $C_1$-$C_4$ alkylthio, $C_1$-$C_4$ alkylsulphinyl and $C_1$-$C_4$ alkylsulphonyl.

Preferably in this group of compounds, $Y_1$ represents hydrogen, halogen, CN, $NO_2$, $C_1$-$C_6$ alkyl, $C_3$-$C_8$ cycloalkyl, $C_2$-$C_6$ alkenyl, phenyl, naphthyl, a 5- to 10-membered mono- or bicyclic heterocycle containing one to three heteroatoms independently selected from O, S and N, providing that the heterocycle does not contain adjacent oxygen atoms, adjacent sulphur atoms, or adjacent sulphur and oxygen atoms, wherein the heterocycle can be aromatic, or fully or partially saturated, $CO_2R^1$, $COR^2$, $N(R^3)_2$ and $C(R^2)=N-OR^1$, wherein the alkyl, cycloalkyl, alkenyl, phenyl, naphthyl and heterocycle are optionally substituted by one or more groups independently selected from halogen, CN, OH, $NH_2$, SH, $NO_2$, $OR^1$, $C_1$-$C_4$ alkyl, $C_1$-$C_4$ haloalkyl, $C_1$-$C_4$ alkylthio, $C_1$-$C_4$ alkylsulphinyl and $C_1$-$C_4$ alkylsulphonyl.

More preferably in this group of compounds, $Y_1$ represents hydrogen, halogen, CN, $NO_2$, $C_1$-$C_4$ alkyl, $C_3$-$C_8$ cycloalkyl, $C_2$-$C_6$ alkenyl, phenyl, naphthyl, a 5- to 10-membered mono- or bicyclic heterocycle containing one to three heteroatoms independently selected from O, S and N, providing that the heterocycle does not contain adjacent oxygen atoms, adjacent sulphur atoms, or adjacent sulphur and oxygen atoms, wherein the heterocycle can be aromatic, or fully or partially saturated, $CO_2H$, $C_1$-$C_4$ alkoxycarbonyl, $C_1$-$C_4$ alkylcarbonyl, $NH_2$, $NH(C_1$-$C_4$ alkyl) and $N(C_1$-$C_4$ alkyl$)_2$, wherein the alkyl, cycloalkyl, alkenyl, phenyl, naphthyl and heterocycle are optionally substituted by one or more groups independently selected from halogen, CN, OH, $NH_2$, SH, $NO_2$, $C_1$-$C_4$ alkoxy, $C_1$-$C_4$ alkyl and $C_1$-$C_4$ haloalkyl.

$Y_2$ and $Y_3$ are independently selected from hydrogen, halogen, CN, $NO_2$, $C_1$-$C_8$ alkyl, $C_3$-$C_8$ cycloalkyl, $C_3$-$C_8$ cycloalkenyl, $C_2$-$C_8$ alkenyl, $C_2$-$C_8$ alkynyl, phenyl, phenyl-$C_1$-$C_6$-alkyl, a 5- or 6-membered heterocycle containing one to three heteroatoms independently selected from O, S and N, providing that the heterocycle does not contain adjacent oxygen atoms, adjacent sulphur atoms, or adjacent sulphur and oxygen atoms, $OR^1$, $COR^2$, SH, $C_1$-$C_8$ alkylthio, $C_1$-$C_8$ alkylsulphinyl, $C_1$-$C_8$ alkylsulphonyl, phenylthio, phenylsulphinyl, phenylsulphonyl, $N(R^3)_2$, $CO_2R^1$, $O(CO)R^2$, $CON(R^3)_2$, $NR^3COR^2$ and $C(R^2)=N-OR^1$, wherein the alkyl, cycloalkyl, cycloalkenyl, alkenyl, alkynyl, phenyl, benzyl, and heterocycle are optionally substituted by one or more groups independently selected from halogen, CN, OH, $NH_2$, SH, $NO_2$, $OR^1$, $C_1$-$C_4$ alkyl, $C_1$-$C_4$ haloalkyl, $C_1$-$C_4$ alkylthio, $C_1$-$C_4$ alkylsulphinyl and $C_1$-$C_4$ alkylsulphonyl.

Preferably, the groups $Y_2$ and $Y_3$ are independently selected from hydrogen, halogen, CN, $C_1$-$C_8$ alkyl, $C_3$-$C_8$ cycloalkyl, $C_3$-$C_8$ cycloalkenyl, $C_2$-$C_8$ alkenyl, $C_2$-$C_8$ alkynyl, phenyl, phenyl-$C_1$-$C_6$ alkyl, $OR^1$, $COR^2$, SH, $C_1$-$C_8$ alkylthio, $C_1$-$C_8$ alkylsulphinyl, $C_1$-$C_8$ alkylsulphonyl, phenylthio, phenylsulphinyl, phenylsulphonyl and $N(R^3)_2$, wherein the alkyl, cycloalkyl, cycloalkenyl, alkenyl, alkynyl, phenyl, benzyl are optionally substituted by one or more groups independently selected from halogen, CN, $NH_2$, $NO_2$, $OR^1$, $C_1$-$C_4$ alkyl, $C_1$-$C_4$ haloalkyl, $C_1$-$C_4$ alkylthio, $C_1$-$C_4$ haloalkylthio, $C_1$-$C_4$ alkylsulfinyl, $C_1$-$C_4$ haloalkylsulfinyl, $C_1$-$C_4$ alkylsulfonyl and $C_1$-$C_4$ haloalkylsulfonyl.

More preferably, $Y_2$ and $Y_3$ are independently selected from hydrogen, halogen, CN, methyl, ethyl, ethynyl, halomethyl, haloethyl, methoxy, halomethoxy, amino, methylamino, dimethylamino, pyrrolidino, piperidino, morpholino, methylthio, halomethylthio, methylsulfinyl and methylsulfonyl.

Even more preferably, the groups $Y_2$ and $Y_3$ are hydrogen.

In one group of compounds, $Y_2$ and $Y_3$ are independently selected from hydrogen and halogen. In this group of compounds, $Y_2$ and $Y_3$ are preferably independently selected from hydrogen and bromine.

Alternately exactly one of the groups $Y_2$ or $Y_3$ represents hydrogen, halogen, CN, $NH_2$, OH, SH, methylthio, methylsulfonyl, methylsulfonyloxy, trifluoromethylsulfonyloxy, nonafluoro-butylsulfonyloxy, phenylsulfonyloxy, para-methyl-phenylsulfonyloxy.

In another group of compounds, $Y_2$ and $Y_3$ are independently selected from hydrogen, $NO_2$, a 5- or 6-membered heterocycle containing one to three heteroatoms independently selected from O, S, N and $N(R^3)$, providing that the heterocycle does not contain adjacent oxygen atoms, adjacent sulphur atoms, or adjacent sulphur and oxygen atoms, $CO_2R^1$, $O(CO)R^2$, $CON(R^3)_2$, $NR^3COR^2$ and $C(R^2)=N-OR^1$, wherein the heterocycle is optionally substituted by one or more groups independently selected from halogen, CN, $NH_2$, SH, $NO_2$, $OR^1$, $C_1$-$C_4$ alkyl, $C_1$-$C_4$ haloalkyl, $C_1$-$C_4$ alkoxy, $C_1$-$C_4$ haloalkoxy, $C_1$-$C_4$ alkylthio, $C_1$-$C_4$ haloalkylthio, $C_1$-$C_4$ alkylsulfinyl, $C_1$-$C_4$ haloalkylsulfinyl, $C_1$-$C_4$ alkylsulfonyl and $C_1$-$C_4$ haloalkylsulfonyl.

$Y_1$ and $Y_2$ may together with the fragment of the compound to which they are attached form a partially or fully unsaturated 5- to 7-membered carbocyclic ring or a partially or fully unsaturated 5- to 7-membered heterocyclic ring containing one to three heteroatoms independently selected from O, S, N and $N(R^3)$, providing that the heterocycle does not contain adjacent oxygen atoms, adjacent sulphur atoms, or adjacent sulphur and oxygen atoms, and wherein the ring formed by $Y_1$ and $Y_2$ is optionally substituted by one or more groups independently selected from halogen, CN, $NH_2$, $NO_2$, OH, SH, $C_1$-$C_4$ alkyl, $C_1$-$C_4$ haloalkyl, $C_1$-$C_4$ alkoxy and $C_1$-$C_4$ haloalkoxy.

G represents a direct bond, O, S, S(O), $SO_2$, C(O), $CO_2$, $C(R^4)(R^5)$, $C(R^4)(R^5)-C(R^6)(R^7)$, $C(R^4)=C(R^5)$, C≡C, $O-C(R^4)(R^5)$, $S-C(R^4)(R^5)$, $C(R^4)(R^5)-O$, $C(R^4)(R^5)-S$ or phenyl.

Preferably, G represents a direct bond, O, S, C(O), $C(R^4)(R^5)$, $C(R^4)(R^5)-C(R^6)(R^7)$ or $C(R^4)=C(R^5)$.

More preferably, G represents a direct bond, C(O), S, $C(R^4)(R^5)$, $C(R^4)(R^5)-C(R^6)(R^7)$ or $C(R^4)=C(R^5)$.

Even more preferably, G represents a direct bond, C(O), $C(R^4)(R^5)$, $C(R^4)(R^5)-C(R^6)(R^7)$ or $C(R^4)=C(R^5)$.

Even more preferably, G represents a direct bond, $C(R^4)(R^5)$, $C(R^4)(R^5)-C(R^6)(R^7)$ or $C(R^4)=C(R^5)$.

Each $R^1$ is independently selected from hydrogen, $C_1$-$C_8$ alkyl, $C_3$-$C_8$ cycloalkyl, $C_3$-$C_8$ cycloalkyl-$C_1$-$C_2$ alkyl, $C_3$-$C_8$ cycloalkenyl, $C_3$-$C_8$ alkenyl, $C_3$-$C_8$ alkynyl, phenyl, benzyl or a 5- or 6-membered heterocycle containing one to three heteroatoms independently selected from O, S, N and $N(R^3)$, providing that the heterocycle does not contain adjacent oxygen atoms, adjacent sulphur atoms, or adjacent sulphur and oxygen atoms, wherein the alkyl, cycloalkyl, cycloalkenyl, alkenyl, alkynyl, phenyl, benzyl and heterocycle are optionally substituted by one or more groups independently selected from halogen, CN, OH, $NH_2$, $NO_2$, SH, $C_1$-$C_4$ alkyl, $C_1$-$C_4$ haloalkyl, $C_1$-$C_4$ alkoxy, $C_1$-$C_4$ haloalkoxy, $C_1$-$C_4$-alkoxy-$C_1$-$C_4$-alkyl and $C_1$-$C_4$ alkoxycarbonyl, and wherein the heterocycle may be attached to the rest of the molecule via a $C_1$-$C_2$ alkylene moiety.

Preferably, each $R^1$ is independently selected from hydrogen, $C_1$-$C_8$ alkyl, $C_3$-$C_8$ cycloalkyl, $C_3$-$C_8$ cycloalkyl-$C_1$-$C_2$ alkyl, $C_3$-$C_8$ cycloalkenyl, $C_3$-$C_8$ alkenyl, $C_3$-$C_8$ alkynyl, phenyl, benzyl or a 5- or 6-membered heterocycle containing one to two heteroatoms independently selected from O, S and N, providing that the heterocycle does not contain adjacent oxygen atoms, adjacent sulphur atoms, or adjacent sulphur and oxygen atoms, wherein the alkyl, cycloalkyl, cycloalkenyl, alkenyl, alkynyl, phenyl, benzyl and heterocycle are optionally substituted by one or more groups independently selected from halogen, CN, OH, $NH_2$, $NO_2$, SH, $C_1$-$C_4$ alkyl, $C_1$-$C_4$ haloalkyl, $C_1$-$C_4$ alkoxy, $C_1$-$C_4$ haloalkoxy and $C_1$-$C_4$ alkoxycarbonyl, and wherein the heterocycle may be attached to the rest of the molecule via a $C_1$-$C_2$ alkylene moeity.

More preferably, each $R^1$ is independently selected from hydrogen, $C_1$-$C_8$ alkyl, $C_3$-$C_6$ cycloalkyl-$C_1$-$C_2$ alkyl, $C_3$-$C_6$ alkenyl, phenyl, benzyl, pyridyl or pyridyl-$C_1$-$C_2$ alkyl wherein the alkyl, cycloalkyl, alkenyl, phenyl, benzyl and pyridyl are optionally substituted by one or more groups independently selected from halogen, CN, OH, $NH_2$, $NO_2$, SH, $C_1$-$C_4$ alkyl, $C_1$-$C_4$ haloalkyl, $C_1$-$C_4$ alkoxy, $C_1$-$C_4$ haloalkoxy and $C_1$-$C_4$ alkoxycarbonyl.

In another group of compounds, each $R^1$ is independently selected from hydrogen, $C_1$-$C_8$ alkyl, $C_3$-$C_8$ cycloalkyl, $C_3$-$C_8$ cycloalkenyl, $C_3$-$C_8$ alkenyl, $C_3$-$C_8$ alkynyl, phenyl, benzyl or a 5- or 6-membered heterocycle containing one to three heteroatoms independently selected from O, S, N and $N(R^3)$, providing that the heterocycle does not contain adjacent oxygen atoms, adjacent sulphur atoms, or adjacent sulphur and oxygen atoms, wherein the alkyl, cycloalkyl, cycloalkenyl, alkenyl, alkynyl, phenyl, benzyl and heterocycle are optionally substituted by one or more groups independently selected from halogen, CN, OH, $NH_2$, $NO_2$, SH, $C_1$-$C_4$ alkyl, $C_1$-$C_4$ haloalkyl, $C_1$-$C_4$ alkoxy, $C_1$-$C_4$ haloalkoxy and $C_1$-$C_4$-alkoxy-$C_1$-$C_4$-alkyl.

Preferably in this group of compounds, each $R^1$ is independently selected from hydrogen, $C_1$-$C_8$ alkyl, $C_3$-$C_8$ cycloalkyl, $C_3$-$C_8$ cycloalkenyl, $C_3$-$C_8$ alkenyl, $C_3$-$C_8$ alkynyl, phenyl and benzyl, wherein the alkyl, cycloalkyl, cycloalkenyl, alkenyl, alkynyl, phenyl and benzyl are optionally substituted by one or more groups independently selected from halogen, CN, $NH_2$, $NO_2$, OH, SH, $C_1$-$C_4$ alkyl, $C_1$-$C_4$-haloalkyl, $C_1$-$C_4$ alkoxy and $C_1$-$C_4$ haloalkoxy.

Even more preferably in this group of compounds, each $R^1$ independently of one another represents hydrogen, $C_1$-$C_8$ alkyl, $C_1$-$C_8$ haloalkyl, $C_3$-$C_8$ alkenyl, $C_3$-$C_8$ alkynyl, $C_3$-$C_8$ haloalkenyl, $C_3$-$C_8$ haloalkynyl, $C_1$-$C_4$ alkylsulphonyl, $C_1$-$C_4$ haloalkylsulphonyl, phenyl or benzyl wherein the phenyl and benzyl are optionally substituted by one or more groups, e.g. one to five groups, independently selected from halogen, CN, $NH_2$, $NO_2$, OH, $C_1$-$C_4$ alkyl, $C_1$-$C_4$-haloalkyl, $C_1$-$C_4$ alkoxy and $C_1$-$C_4$ haloalkoxy.

Yet more preferably in this group of compounds, each $R^1$ independently of one another represents hydrogen, $C_1$-$C_8$ alkyl, $C_1$-$C_8$ haloalkyl, $C_3$-$C_8$ alkenyl, $C_3$-$C_8$ haloalkenyl, $C_3$-$C_8$ alkynyl, $C_3$-$C_8$ haloalkynyl, $C_1$-$C_4$ alkylsulphonyl, $C_1$-$C_4$ haloalkylsulphonyl, phenyl or benzyl wherein the phenyl and benzyl are optionally substituted by one or more groups, e.g. one to five groups, independently selected from halogen, CN, $C_1$-$C_4$ alkyl, $C_1$-$C_4$-haloalkyl, $C_1$-$C_4$ alkoxy and $C_1$-$C_4$ haloalkoxy.

It is particularly preferred in this group of compounds that each $R^1$ independently of one another represents hydrogen, $C_1$-$C_4$ alkyl or $C_1$-$C_4$ haloalkyl.

In another group of compounds, each $R^1$ is independently selected from the group of hydrogen, phenyl and a 5- or 6-membered heterocycle containing one to three heteroatoms independently selected from O, S, N and $N(R^3)$, providing that the heterocycle does not contain adjacent oxygen atoms, adjacent sulphur atoms, or adjacent sulphur and oxygen atoms, wherein the phenyl and heterocycle are optionally substituted by one or more groups independently selected from halogen, CN, $NH_2$, $NO_2$, OH, SH, $C_1$-$C_4$ alkyl, $C_1$-$C_4$-haloalkyl, $C_1$-$C_4$ alkoxy, $C_1$-$C_4$ haloalkoxy and $C_1$-$C_4$-alkoxy-$C_1$-$C_4$-alkyl.

In a further group of compounds, each $R^1$ independently of one another represents hydrogen, $C_1$-$C_8$ alkyl, $C_1$-$C_8$ haloalkyl, $C_3$-$C_8$ alkenyl, $C_3$-$C_8$ alkynyl, $C_3$-$C_8$ haloalkenyl, $C_3$-$C_8$ haloalkynyl, $C_1$-$C_4$ alkylsulphonyl, $C_1$-$C_4$ haloalkylsulphonyl, phenyl, benzyl or pyridyl, wherein the phenyl, benzyl and pyridyl are optionally substituted by one or more groups, e.g. one to five groups, independently selected from halogen, CN, $NH_2$, $NO_2$, OH, $C_1$-$C_4$ alkyl, $C_1$-$C_4$-haloalkyl, $C_1$-$C_4$ alkoxy and $C_1$-$C_4$ haloalkoxy.

Yet more preferably in this group of compounds, each $R^1$ independently of one another represents hydrogen, $C_1$-$C_8$ alkyl, $C_1$-$C_8$ haloalkyl, $C_3$-$C_8$ alkenyl, $C_3$-$C_8$ haloalkenyl, $C_3$-$C_8$ alkynyl, $C_3$-$C_8$ haloalkynyl, $C_1$-$C_4$ alkylsulphonyl, $C_1$-$C_4$ haloalkylsulphonyl, phenyl, benzyl, or pyridyl, wherein the phenyl, benzyl and pyridyl are optionally substituted by one or more groups, e.g. one to five groups, independently selected from halogen, CN, $C_1$-$C_4$ alkyl, $C_1$-$C_4$-haloalkyl, $C_1$-$C_4$ alkoxy and $C_1$-$C_4$ haloalkoxy.

Each $R^2$ is independently selected from hydrogen, $C_1$-$C_8$ alkyl, $C_3$-$C_8$ cycloalkyl, $C_3$-$C_8$ cycloalkenyl, $C_2$-$C_8$ alkenyl, $C_2$-$C_8$ alkynyl, phenyl, benzyl and pyridyl, wherein the alkyl, cycloalkyl, cycloalkenyl, alkenyl, alkynyl, phenyl, benzyl and pyridyl groups are optionally substituted by one or more groups independently selected from halogen, CN, $NH_2$, $NO_2$, OH, $C_1$-$C_4$ alkyl, $C_1$-$C_4$ haloalkyl, $C_1$-$C_4$ alkoxy, $C_1$-$C_4$ alkylthio and $C_1$-$C_4$ haloalkoxy.

Preferably, each $R^2$ is independently selected from the group of hydrogen, $C_1$-$C_8$ alkyl, $C_3$-$C_8$ cycloalkyl, $C_3$-$C_8$ cycloalkenyl, $C_2$-$C_8$ alkenyl, $C_2$-$C_8$ alkynyl and benzyl wherein the alkyl, cycloalkyl, cycloalkenyl, alkenyl, alkynyl and benzyl are optionally substituted by one or more groups independently selected from halogen, CN, $NH_2$, $NO_2$, OH, $C_1$-$C_4$ alkyl, $C_1$-$C_4$ haloalkyl, $C_1$-$C_4$ alkoxy and $C_1$-$C_4$ haloalkoxy.

More preferably, each $R^2$ independently of one another represents hydrogen, $C_1$-$C_8$ alkyl or $C_1$-$C_8$ haloalkyl.

Even more preferably, each $R^2$ independently of one another represents hydrogen, $C_1$-$C_4$ alkyl or $C_1$-$C_4$ haloalkyl.

Most preferably, $R^2$ represents methyl.

Each $R^3$ is independently selected from hydrogen, $C_1$-$C_8$ alkyl, $C_3$-$C_8$ alkenyl, $C_3$-$C_8$ cycloalkyl, $C_3$-$C_8$ cycloalkenyl, $C_3$-$C_8$ alkynyl, phenyl, benzyl, CN, $OR^1$, $COR^2$, $C_1$-$C_8$ alkylsulphonyl, and a 5- or 6-membered heterocycle containing one to three heteroatoms independently selected from O, S, N and $N(R^8)$, providing that the heterocycle does not contain adjacent oxygen atoms, adjacent sulphur atoms, or adjacent sulphur and oxygen atoms, wherein the alkyl, cycloalkyl, cycloalkenyl, alkenyl, alkynyl, phenyl, benzyl and heterocycle are optionally substituted by one or more groups independently selected from halogen, CN, $NH_2$, $NO_2$, OH, $C_1$-$C_4$ alkyl, $C_1$-$C_4$-haloalkyl, $C_1$-$C_4$ alkoxy, $C_1$-$C_4$ haloalkoxy and $C_1$-$C_4$-alkoxy-$C_1$-$C_4$-alkyl;

wherein when two radicals $R^3$ are attached to the same nitrogen atom, these radicals can be identical or different;

wherein when two radicals $R^3$ are attached to the same nitrogen atom, both of these radicals cannot be $OR^1$;

and wherein when two radicals $R^3$ are attached to the same nitrogen atom, these two radicals together with the nitrogen atom to which they are attached may form a cycle selected from B-1, B-2, B-3, B-4, B-5, B-6, B-7 and B-8:

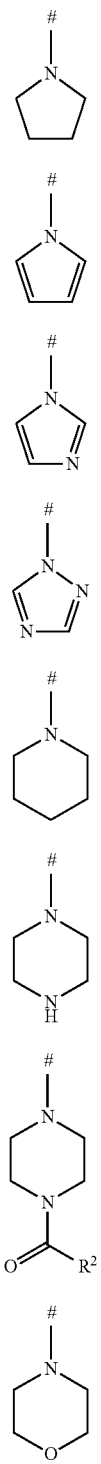

B-1
B-2
B-3
B-4
B-5
B-6
B-7
B-8 wherein the cycle formed is optionally substituted by one or more groups independently selected from halogen, CN, $NH_2$, $NO_2$, OH, $C_1$-$C_4$ alkyl, $C_1$-$C_4$ haloalkyl, $C_1$-$C_4$ alkoxy and $C_1$-$C_4$ haloalkoxy.

Preferably, each $R^3$ is independently selected from the group of hydrogen, $C_1$-$C_8$ alkyl, $C_2$-$C_8$ alkenyl, $C_3$-$C_8$ cycloalkyl, $C_3$-$C_8$ cycloalkenyl, $C_2$-$C_8$ alkynyl, phenyl, benzyl, CN, $OR^1$, $COR^2$ and $C_1$-$C_8$ alkylsulphonyl, wherein the alkyl, cycloalkyl, cycloalkenyl, alkenyl, alkynyl, phenyl and benzyl are optionally substituted by one or more groups independently selected from halogen, CN, $NH_2$, $NO_2$, OH, $C_1$-$C_4$ alkyl, $C_1$-$C_4$-haloalkyl, $C_1$-$C_4$ alkoxy, $C_1$-$C_4$ haloalkoxy and $C_1$-$C_4$-alkoxy-$C_1$-$C_4$-alkyl;

wherein when two radicals $R^3$ are attached to the same nitrogen atom, these radicals can be identical or different;

wherein when two radicals $R^3$ are attached to the same nitrogen atom, both of these radicals cannot be $OR^1$;

and wherein when two radicals $R^3$ are attached to the same nitrogen atom, these two radicals together with the nitrogen atom to which they are attached may form a cycle B-1, B-2, B-5, or B-8;

wherein the cycle formed is optionally substituted by one or more groups independently selected from halogen, CN, $NH_2$, $NO_2$, OH, $C_1$-$C_4$ alkyl, $C_1$-$C_4$ haloalkyl, $C_1$-$C_4$ alkoxy and $C_1$-$C_4$ haloalkoxy.

Even more preferably, each $R^3$ independently of one another represents hydrogen, $C_1$-$C_8$ alkyl, $C_3$-$C_8$ cycloalkyl, $C_3$-$C_8$ alkenyl, $C_3$-$C_8$ alkynyl or $COR^2$; wherein when two radicals $R^3$ are attached to the same nitrogen atom, these radicals can be identical or different; and wherein when two radicals $R^3$ are attached to the same nitrogen atom, these two radicals together with the nitrogen atom to which they are attached may form a cycle B-1, B-2, B-5, or B-8; wherein the cycle formed is optionally substituted by one or more groups, e.g. one to five groups, independently selected from halogen, methyl and halomethyl.

More preferably still, each $R^3$ independently of one another represents hydrogen, $C_1$-$C_4$ alkyl, $C_3$-$C_4$ alkenyl, $C_3$-$C_4$ alkynyl or $COR^2$; wherein when two radicals $R^3$ are attached to the same nitrogen atom, these radicals can be identical or different; and wherein when two radicals $R^3$ are attached to the same nitrogen atom, these two radicals together with the nitrogen atom to which they are attached may form a cycle B-1, B-2, B-5, or B-8, wherein the cycle formed is optionally substituted by one or more groups, e.g. one to five groups, independently selected from halogen, methyl and halomethyl.

Yet more preferably, each $R^3$ independently of one another represents hydrogen, $C_1$-$C_8$ alkyl or $COR^2$.

It is particularly preferred that each $R^3$ independently of one another represents hydrogen or $C_1$-$C_4$ alkyl.

In another group of compounds, each $R^3$ is selected from the group of hydrogen, phenyl and a 5- or 6-membered heterocycle containing one to three heteroatoms independently selected from O, S, N and $N(R^8)$, providing that the heterocycle does not contain adjacent oxygen atoms, adjacent sulphur atoms, or adjacent sulphur and oxygen atoms, wherein the phenyl and heterocycle are optionally substituted by one or more groups independently selected from halogen, CN, $NH_2$, $NO_2$, OH, $C_1$-$C_4$ alkyl, $C_1$-$C_4$-haloalkyl, $C_1$-$C_4$ alkoxy, $C_1$-$C_4$ haloalkoxy and $C_1$-$C_4$-alkoxy-$C_1$-$C_4$-alkyl;

wherein when two radicals $R^3$ are attached to the same nitrogen atom, these radicals can be identical or different;

wherein $R^8$ represents hydrogen, $C_1$-$C_8$ alkyl, $C_1$-$C_8$ haloalkyl, $C_3$-$C_8$ cycloalkyl, $C_3$-$C_8$, $C_3$-$C_8$ alkenyl, $C_3$-$C_8$ alkynyl or $C_1$-$C_8$ alkoxy-$C_1$-$C_8$ alkyl.

$R^4$, $R^5$, $R^6$ and $R^7$ independently of one another represent hydrogen, halogen, cyano, $C_1$-$C_4$ alkyl, $C_1$-$C_4$ alkoxy, $C_3$-$C_5$ cycloalkyl, $C_1$-$C_4$ haloalkyl, or $C_1$-$C_4$ alkylthio;

wherein two radicals $R^4$ and $R^5$ or $R^6$ and $R^7$ or $R^4$ and $R^6$ together with the carbon atom to which they are attached may form a 3- to 6-membered carbocycle or heterocycle containing one to three heteroatoms independently selected from O, S, N and $N(R^8)$, providing that the heterocycle does not contain adjacent oxygen atoms, adjacent sulphur atoms, or adjacent sulphur and oxygen atoms, wherein carbocycle and heterocycle are optionally substituted by one or more groups independently selected from halogen, CN, $NH_2$, $NO_2$, OH, $C_1$-$C_4$ alkyl, $C_1$-$C_4$-haloalkyl, $C_1$-$C_4$ alkoxy, $C_1$-$C_4$ haloalkoxy and $C_1$-$C_4$-alkoxy-$C_1$-$C_4$-alkyl.

Preferably, $R^4$, $R^5$, $R^6$ and $R^7$ independently of one another represent hydrogen, halogen, cyano, $C_1$-$C_4$ alkyl, $C_1$-$C_4$ alkoxy, $C_3$-$C_5$ cycloalkyl, $C_1$-$C_4$ haloalkyl, or $C_1$-$C_4$ alkylthio.

Most preferably, $R^4$, $R^5$, $R^6$ and $R^7$ each represent hydrogen.

$R^8$ represents hydrogen, $C_1$-$C_8$ alkyl, $C_1$-$C_8$ haloalkyl, $C_3$-$C_8$ cycloalkyl, $C_3$-$C_8$ alkenyl, $C_3$-$C_8$ alkynyl or $C_1$-$C_8$ alkoxy-$C_1$-$C_8$ alkyl.

$V_1$ and $V_2$ independently of one another represent hydrogen, $C_1$-$C_8$ alkyl, $C_3$-$C_8$ alkenyl, $C_3$-$C_8$ cycloalkyl, $C_3$-$C_8$ cycloalkenyl, $C_3$-$C_8$ alkynyl, benzyl, $C_2$-$C_9$ alkoxycarbonyl, $C_4$-$C_9$ alkenyloxycarbonyl, benzyloxycarbonyl or $COR^2$, wherein the alkyl, alkenyl, alkynyl, cycloalkyl, cycloalkenyl and benzyl are optionally substituted by one or more groups independently selected from halogen, CN, OH, $C_1$-$C_4$ alkyl, $C_1$-$C_4$ haloalkyl, $C_1$-$C_4$ alkoxy or $C_1$-$C_4$ haloalkoxy;

and wherein $V_1$ and $V_2$ together with the nitrogen atom to which they are attached may form a cycle selected from B-9, B-10, B-11, B-12 and B-13:

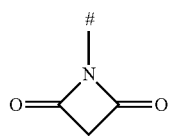

B-9

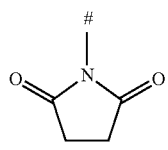

B-10

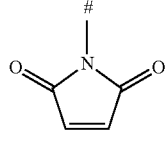

B-11

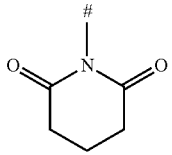

B-12

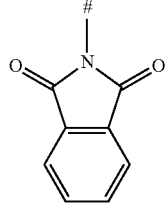

B-13 wherein the cycle so formed is optionally substituted by one or more groups independently selected from halogen, CN, $NH_2$, OH, $C_1$-$C_4$ alkyl, $C_1$-$C_4$ haloalkyl, $C_1$-$C_4$ alkoxy and $C_1$-$C_4$ haloalkoxy.

Preferably, $V_1$ and $V_2$ are independently selected from hydrogen, $C_1$-$C_8$ alkyl, $C_3$-$C_8$ alkenyl, $C_3$-$C_8$ cycloalkyl, $C_3$-$C_8$ cycloalkenyl, $C_3$-$C_8$ alkynyl, benzyl, and $COR^2$, wherein the alkyl, alkenyl, alkynyl, cycloalkyl, cycloalkenyl and benzyl are optionally substituted by one or more halogen, CN, OH, $C_1$-$C_4$ alkyl, $C_1$-$C_4$ haloalkyl, $C_1$-$C_4$ alkoxy and $C_1$-$C_4$ haloalkoxy, or $V_1$ and $V_2$ together with the nitrogen atom to which they are attached may form the cycle B-10.

More preferably, $V_1$ and $V_2$ are independently selected from hydrogen, $C_1$-$C_8$ alkyl, $C_3$-$C_8$ alkenyl, $C_3$-$C_8$ cycloalkyl, $C_3$-$C_8$ cycloalkenyl, $C_3$-$C_8$ alkynyl, benzyl, and $COR^2$, or $V_1$ and $V_2$ together with the nitrogen atom to which they are attached may form the cycle B-10.

Even more preferably, $V_1$ and $V_2$ are independently selected from hydrogen and $C_1$-$C_4$-alkylcarbonyl, or $V_1$ and $V_2$ together with the nitrogen atom to which they are attached may form the cycle B-10.

In one group of compounds, $V_1$ is hydrogen and $V_2$ is as described above.

Most preferably, both $V_1$ and $V_2$ are hydrogen.

In another group of compounds, $V_1$ and $V_2$ are independently selected from the group consisting of $C_2$-$C_9$-alkoxycarbonyl, $C_4$-$C_9$-alkenyloxycarbonyl, benzyloxycarbonyl or $COR^2$.

In a further group of compounds, $V_1$ and $V_2$ are independently selected from hydrogen, $C_1$-$C_8$ alkyl, $C_3$-$C_8$ alkenyl, $C_3$-$C_8$ cycloalkyl, $C_3$-$C_8$ cycloalkenyl, $C_3$-$C_8$ alkynyl, benzyl, and $COR^2$, wherein the alkyl, alkenyl, alkynyl, cycloalkyl, cycloalkenyl and benzyl are optionally substituted by one or more halogen, CN, OH, $C_1$-$C_4$ alkyl, $C_1$-$C_4$ haloalkyl, $C_1$-$C_4$ alkoxy and $C_1$-$C_4$ haloalkoxy.

More preferably, in this group of compounds, $V_1$ and $V_2$ are independently selected from hydrogen, $C_1$-$C_8$ alkyl, $C_3$-$C_8$ alkenyl, $C_3$-$C_8$ cycloalkyl, $C_3$-$C_8$ cycloalkenyl, $C_3$-$C_8$ alkynyl, benzyl, and $COR^2$.

Even more preferably, in this group of compounds, $V_1$ and $V_2$ are independently selected from hydrogen and $C_1$-$C_4$-alkylcarbonyl.

$V_3$ is selected from hydrogen, halogen, CN, $NO_2$, $NH_2$, $C_1$-$C_8$ alkyl, $C_3$-$C_8$ cycloalkyl, $C_3$-$C_8$ cycloalkenyl, $C_2$-$C_8$ alkenyl, $C_2$-$C_8$ alkynyl, phenyl, benzyl, a 5- or 6-membered heterocycle containing one to three heteroatoms independently selected from O, S, N and $N(R^3)$, providing that the heterocycle does not contain adjacent oxygen atoms, adjacent sulphur atoms, or adjacent sulphur and oxygen atoms, $OR^1$, $COR^2$, SH, $C_1$-$C_8$ alkylthio, $C_1$-$C_8$ alkylsulphinyl, $C_1$-$C_8$ alkylsulphonyl, phenylthio, phenylsulphinyl, phenylsulphonyl, $N(R^3)_2$, $CO_2R^1$, $O(CO)R^2$, $CON(R^3)_2$, $NR^3COR^2$ and $C(R^2)=N-OR^1$, wherein the alkyl, cycloalkyl, cycloalkenyl, alkenyl, alkynyl, phenyl, benzyl, and heterocycle are optionally substituted by one or more groups independently selected from halogen, CN, $NH_2$, SH, $NO_2$, $OR^1$, $C_1$-$C_4$ alkyl and $C_1$-$C_4$ haloalkyl.

Preferably, $V_3$ is selected from hydrogen, halogen, $NH_2$, $C_1$-$C_8$ alkyl, $C_3$-$C_8$ cycloalkyl, $C_3$-$C_8$ cycloalkenyl, $C_2$-$C_8$ alkenyl, $C_2$-$C_8$ alkynyl, phenyl and benzyl wherein the alkyl, cycloalkyl, cycloalkenyl, alkenyl, alkynyl, phenyl and benzyl, are optionally substituted by one or more groups independently selected from halogen, CN, $NH_2$, $NO_2$, $OR^1$, $C_1$-$C_4$ alkyl and $C_1$-$C_4$ haloalkyl.

More preferably, $V_3$ is selected from hydrogen, halogen, $C_1$-$C_6$ alkyl, $C_1$-$C_4$ haloalkyl, phenyl, benzyl, $C_3$-$C_8$ cycloalkyl, or amino.

Even more preferably, $V_3$ is selected from hydrogen, halogen, $C_1$-$C_6$ alkyl, $C_1$-$C_4$ haloalkyl, phenyl, benzyl, cyclopropyl or amino.

More preferably again, $V_3$ is selected from hydrogen, halogen, $C_1$-$C_6$ alkyl, $C_1$-$C_4$ haloalkyl or cyclopropyl.

It is particularly preferred that $V_3$ is hydrogen.

In one group of compounds, $V_3$ is selected from hydrogen, halogen, $NH_2$, $C_1$-$C_8$ alkyl, $C_3$-$C_8$ cycloalkyl, $C_3$-$C_8$ cycloalkenyl, $C_2$-$C_8$ alkenyl, $C_2$-$C_8$ alkynyl, phenyl and benzyl wherein the alkyl, cycloalkyl, cycloalkenyl, alkenyl, alkynyl, phenyl and benzyl, are optionally substituted by one or more groups independently selected from halogen, CN, $NH_2$, $NO_2$, $OR^1$, $C_1$-$C_4$ alkyl and $C_1$-$C_4$ haloalkyl.

More preferably in this group of compounds, $V_3$ is selected from hydrogen, halogen, $C_1$-$C_6$ alkyl, $C_1$-$C_4$ haloalkyl, phenyl, benzyl or amino.

More preferably again in this group of compounds, $V_3$ is selected from hydrogen, halogen, $C_1$-$C_6$ alkyl, $C_1$-$C_4$ haloalkyl or amino.

In another group of compounds, $V_3$ is selected from hydrogen, halogen, CN, methyl, halomethyl, methoxy, halomethoxy, methylthio, halomethylthio, methylsulfinyl, halomethylsulfinyl, methylsulfonyl, halomethylsulfonyl, amino, methylamino, dimethylamino, OH, SH, methylsulfonyloxy, trifluoromethylsulfonyloxy, nonafluoro-butylsulfonyloxy, phenylsulfonyloxy, para-methyl-phenylsulfonyloxy.

$V_4$ is selected from hydrogen, OH, $C_1$-$C_8$ alkyl, $C_1$-$C_8$ alkoxy, $C_3$-$C_8$ alkenyl, $C_3$-$C_8$ alkenyloxy, $C_3$-$C_8$ cycloalkyl, $C_3$-$C_8$ cycloalkenyl, $C_3$-$C_8$ cycloalkoxy, $C_3$-$C_8$ alkynyl, $C_3$-$C_8$ alkynyloxy, phenyl, phenyl-$C_1$-$C_6$-alkyl, benzyloxy, pyridyl, pyridyl-$C_1$-$C_6$-alkyl, $COR^2$, $CO_2R^2$, $CON(R^3)_2$ and $SO_2$—$C_1$-$C_8$-alkyl, wherein the alkyl, alkenyl, alkynyl, cycloalkyl, cycloalkenyl, phenyl, benzyl and pyridyl are optionally substituted by one or more groups independently selected from halogen, CN, $NH_2$, $NO_2$, OH, $C_1$-$C_4$ alkyl, $C_1$-$C_4$ haloalkyl, $C_1$-$C_4$ alkoxy and $C_1$-$C_4$ haloalkoxy.

Preferably, $V_4$ is selected from hydrogen, $C_1$-$C_8$ alkyl, $C_3$-$C_8$ alkenyl, $C_3$-$C_8$ cycloalkyl, $C_3$-$C_8$ cycloalkenyl, $C_3$-$C_8$ alkynyl, phenyl, phenyl-$C_1$-$C_6$-alkyl, pyridyl, pyridyl-$C_1$-$C_6$-alkyl, $COR^2$, $CO_2R^2$, $CON(R^3)_2$ and $SO_2$—$C_1$-$C_8$-alkyl, wherein the alkyl, alkenyl, alkynyl, cycloalkyl, cycloalkenyl, phenyl and pyridyl are optionally substituted by one or more groups independently selected from halogen, CN, $NH_2$, $NO_2$, OH, $C_1$-$C_4$ alkyl, $C_1$-$C_4$ haloalkyl, $C_1$-$C_4$ alkoxy and $C_1$-$C_4$ haloalkoxy.

More preferably, $V_4$ is hydrogen, $C_3$-$C_6$ cycloalkyl, $C_3$-$C_6$ alkenyl, $C_3$-$C_6$ alkynyl, phenyl-$C_1$-$C_4$-alkyl or $C_1$-$C_6$-alkyl, wherein alkyl, alkenyl or alkylnyl groups are optionally substituted by one or more groups independently selected from halogen, CN, OH, $C_1$-$C_4$ alkyl, $C_1$-$C_4$ haloalkyl, $C_1$-$C_4$ alkoxy and $C_1$-$C_4$ haloalkoxy More preferably still, $V_4$ is selected from hydrogen, $C_1$-$C_4$ alkyl, $C_1$-$C_4$ haloalkyl, $C_3$-$C_4$ alkenyl, phenyl-$C_1$-$C_2$-alkyl or $C_3$-$C_8$ cycloalkyl.

Most preferably, $V_4$ is selected from hydrogen, $C_1$-$C_4$ alkyl, $C_1$-$C_4$ haloalkyl, $C_3$-$C_4$ alkenyl, phenyl-$C_1$-$C_2$-alkyl, cyclopropyl, cyclopentyl or cyclohexyl.

In another group of compounds, $V_4$ is selected from hydrogen, $C_1$-$C_8$ alkyl, $C_3$-$C_8$ alkenyl, $C_3$-$C_8$ cycloalkyl, $C_3$-$C_8$ cycloalkenyl, $C_3$-$C_8$ alkynyl, phenyl, phenyl-$C_1$-$C_6$-alkyl, pyridyl, pyridyl-$C_1$-$C_6$-alkyl, $COR^2$, $CO_2R^2$, $CON(R^3)_2$ and $SO_2$—$C_1$-$C_8$-alkyl, wherein the alkyl, alkenyl, alkynyl, cycloalkyl, cycloalkenyl, phenyl and pyridyl are optionally substituted by one or more groups independently selected from halogen, CN, $NH_2$, $NO_2$, OH, $C_1$-$C_4$ alkyl, $C_1$-$C_4$ haloalkyl, $C_1$-$C_4$ alkoxy and $C_1$-$C_4$ haloalkoxy.

More preferably in this group of compounds, $V_4$ is hydrogen, $C_3$-$C_6$ cycloalkyl, $C_3$-$C_6$ alkenyl, $C_3$-$C_6$ alkynyl, phenyl-$C_1$-$C_4$-alkyl or $C_1$-$C_6$-alkyl, wherein alkyl, alkenyl or alkylnyl groups are optionally substituted by one or more groups independently selected from halogen, CN, OH, $C_1$-$C_4$ alkyl, $C_1$-$C_4$ haloalkyl, $C_1$-$C_4$ alkoxy and $C_1$-$C_4$ haloalkoxy More preferably still in this group of compounds, $V_4$ is selected from hydrogen, $C_1$-$C_4$ alkyl, $C_3$-$C_4$ alkenyl, phenyl-$C_1$-$C_2$-alkyl or $C_3$-$C_8$ cycloalkyl.

Even more preferably in this group of compounds, $V_4$ is selected from hydrogen, $C_1$-$C_4$ alkyl, $C_3$-$C_4$ alkenyl, phenyl-$C_1$-$C_2$-alkyl, cyclopropyl, cyclopentyl or cyclohexyl.

Most preferably in this group of compounds, $V_4$ is selected from hydrogen, $C_1$-$C_4$ alkyl, $C_3$-$C_4$ alkenyl, cyclopropyl, cyclopentyl or cyclohexyl.

In one group of compounds, $V_4$ is selected from phenyl, phenyl-$C_1$-$C_6$-alkyl, pyridyl and pyridyl-$C_1$-$C_6$-alkyl wherein the alkyl, phenyl and pyridyl are optionally substituted by one or more groups independently selected from halogen, CN, $NH_2$, $NO_2$, OH, $C_1$-$C_4$ alkyl, $C_1$-$C_4$ haloalkyl, $C_1$-$C_4$ alkoxy and $C_1$-$C_4$ haloalkoxy.

Even more preferably in this group, $V_4$ is phenyl-$C_1$-$C_6$-alkyl, wherein the phenyl is optionally substituted by one or more groups independently selected from halogen, CN, $NH_2$, $NO_2$, OH, $C_1$-$C_4$ alkyl, $C_1$-$C_4$ haloalkyl, $C_1$-$C_4$ alkoxy and $C_1$-$C_4$ haloalkoxy;

or $V_4$ is $C_3$-$C_6$ cycloalkyl, $C_3$-$C_6$ alkenyl, $C_3$-$C_6$ alkynyl or $C_1$-$C_6$-alkyl, wherein alkyl, alkenyl or alkylnyl groups are optionally substituted by one or more groups independently selected from halogen, CN, OH, $C_1$-$C_4$ alkyl, $C_1$-$C_4$ haloalkyl, $C_1$-$C_4$ alkoxy and $C_1$-$C_4$ haloalkoxy.

More preferably still in this group of compounds, $V_4$ is a cycloalkyl group selected from cyclopropyl, cyclobutyl, cyclopentyl, cyclohexyl, cycloheptyl and cyclooctyl;

or $V_4$ is selected from $C_1$-$C_6$ alkyl, $C_3$-$C_6$ alkenyl and $C_3$-$C_6$ alkynyl.

More preferably still in this group of compounds, $V_4$ is an alkyl group selected from methyl, ethyl, propyl, butyl, pentyl, hexyl, iso-propyl, iso-butyl, sec-butyl, 1-(1-methylbutyl), 1-(2-methylbutyl) and 1-(3-methylbutyl).

In one group of compounds, $V_4$ is selected from phenyl, phenyl-$C_1$-$C_6$-alkyl, pyridyl and pyridyl-$C_1$-$C_6$-alkyl wherein the alkyl, phenyl and pyridyl are optionally substituted by one or more groups independently selected from halogen, CN, $NH_2$, $NO_2$, OH, $C_1$-$C_4$ alkyl, $C_1$-$C_4$ haloalkyl, $C_1$-$C_4$ alkoxy and $C_1$-$C_4$ haloalkoxy.

Even more preferably in this group, $V_4$ is phenyl-$C_1$-$C_6$-alkyl, wherein the phenyl is optionally substituted by one or more groups independently selected from halogen, CN, $NH_2$, $NO_2$, OH, $C_1$-$C_4$ alkyl, $C_1$-$C_4$ haloalkyl, $C_1$-$C_4$ alkoxy and $C_1$-$C_4$ haloalkoxy.

In another group of compounds, $V_4$ is $C_3$-$C_6$ cycloalkyl, $C_3$-$C_6$ alkenyl, $C_3$-$C_6$ alkynyl or $C_1$-$C_6$-alkyl, wherein alkyl, alkenyl or alkylnyl groups are optionally substituted by one or more groups independently selected from halogen, CN, OH, $C_1$-$C_4$ alkyl, $C_1$-$C_4$ haloalkyl, $C_1$-$C_4$ alkoxy and $C_1$-$C_4$ haloalkoxy.

More preferably still in this group of compounds, $V_4$ is a cycloalkyl group selected from cyclopropyl, cyclobutyl, cyclopentyl, cyclohexyl, cycloheptyl and cyclooctyl.

or $V_4$ is selected from $C_1$-$C_6$ alkyl, $C_3$-$C_6$ alkenyl and $C_3$-$C_6$ alkynyl.

In another group of compounds, $V_4$ is an alkyl group selected from methyl, ethyl, propyl, butyl, pentyl, hexyl, iso-propyl, iso-butyl, sec-butyl, 1-(1-methylbutyl), 1-(2-methylbutyl) and 1-(3-methylbutyl).

In one preferred group of compounds:

$Y_1$ and $Y_2$, together with the fragment of the compound to which they are attached may form a partially or fully unsaturated 5- to 7-membered carbocyclic ring or a partially or fully unsaturated 5- to 7-membered heterocyclic ring containing one to three heteroatoms independently selected from O, S, N and $N(R^3)$, providing that the heterocycle does not contain adjacent oxygen atoms, adjacent sulphur atoms, or adjacent sulphur and oxygen atoms, and wherein the ring formed by $Y_1$ and $Y_2$ is optionally substituted by one or more groups independently selected from halogen, CN, $NH_2$, $NO_2$, OH, SH, $C_1$-$C_4$ alkyl, $C_1$-$C_4$ haloalkyl, $C_1$-$C_4$ alkoxy, $C_1$-$C_4$ haloalkoxy, $C_1$-$C_4$ alkylthio, $C_1$-$C_4$ haloalkylthio, $C_1$-$C_4$ alkylsulfinyl, $C_1$-$C_4$ haloalkylsulfinyl, $C_1$-$C_4$ alkylsulfonyl and $C_1$-$C_4$ haloalkylsulfonyl.

In one preferred group of compounds:

$V_1$ is hydrogen and $V_2$ is selected from $C_2$-$C_9$-alkoxycarbonyl, $C_4$-$C_9$-alkenyloxycarbonyl, benzyloxycarbonyl and $COR^2$.

In another preferred group of compounds:

$V_1$, $V_2$ and $V_3$ are hydrogen and $V_4$ is a cycloalkyl group selected from cyclopropyl, cyclobutyl, cyclopentyl, cyclohexyl, cycloheptyl and cyclooctyl.

In another preferred group of compounds:

$V_1$, $V_2$ and $V_3$ are hydrogen and $V_4$ is selected from $C_1$-$C_6$ alkyl, $C_3$-$C_6$ alkenyl and $C_3$-$C_6$ alkynyl.

In another preferred group of compounds:

$V_1$, $V_2$ and $V_3$ are hydrogen and $V_4$ is phenyl-$C_1$-$C_6$-alkyl, wherein the phenyl is optionally substituted by one or more groups independently selected from halogen, CN, $NH_2$, $NO_2$, OH, $C_1$-$C_4$ alkyl, $C_1$-$C_4$ haloalkyl, $C_1$-$C_4$ alkoxy and $C_1$-$C_4$ haloalkoxy.

In another preferred group of compounds:

$V_1$, $V_2$ and $V_3$ are hydrogen and $V_4$ is an alkyl group selected from methyl, ethyl, propyl, butyl, pentyl, hexyl, iso-propyl, iso-butyl, sec-butyl, 1-(1-methylbutyl), 1-(2-methylbutyl) and 1-(3-methylbutyl).

In a further preferred group of compounds:

$Y_1$ represents hydrogen, halogen, CN, $NO_2$, $C_1$-$C_6$ alkyl, $C_3$-$C_8$ cycloalkyl, $C_2$-$C_6$ alkenyl, phenyl, naphthyl, a 5- to 10-membered mono- or bicyclic heterocycle containing one to three heteroatoms independently selected from O, S and N, providing that the heterocycle does not contain adjacent oxygen atoms, adjacent sulphur atoms, or adjacent sulphur and oxygen atoms, wherein the heterocycle can be aromatic, or fully or partially saturated, $CO_2R^1$, $COR^2$, $N(R^3)_2 C(R^2)=N-OR^1$, wherein the alkyl, cycloalkyl, alkenyl, phenyl, naphthyl and heterocycle are optionally substituted by one or more groups independently selected from halogen, CN, OH, $NH_2$, SH, $NO_2$, $OR^1$, $C_1$-$C_4$ alkyl, $C_1$-$C_4$ haloalkyl, $C_1$-$C_4$ alkylthio, $C_1$-$C_4$ alkylsulphinyl and $C_1$-$C_4$ alkylsulphonyl;

$Y_2$ and $Y_3$ are independently selected from hydrogen, halogen, CN, methyl, ethyl, ethynyl, halomethyl, haloethyl, methoxy, halomethoxy, amino, methylamino, dimethylamino, pyrrolidino, piperidino, morpholino, methylthio, halomethylthio, methylsulfinyl and methylsulfonyl;

or $Y_3$ is as defined above and $Y_1$ and $Y_2$ together with the fragment of the compound to which they are attached form a partially or fully unsaturated 5- to 7-membered carbocyclic ring or a partially or fully unsaturated 5- to 7-membered heterocyclic ring containing one to three heteroatoms independently selected from O, S, N and $N(R^3)$, providing that the heterocycle does not contain adjacent oxygen atoms, adjacent sulphur atoms, or adjacent sulphur and oxygen atoms, and wherein the ring formed by $Y_1$ and $Y_2$ is optionally substituted by one or more groups independently selected from halogen, CN, $NH_2$, OH, SH, $C_1$-$C_4$ alkyl, $C_1$-$C_4$ haloalkyl, $C_1$-$C_4$ alkoxy and $C_1$-$C_4$ haloalkoxy;

G represents a direct bond, O, S, C(O), $C(R^4)(R^5)$, $C(R^4)(R^5)$—$C(R^6)(R^7)$, or $C(R^4)=C(R^5)$;

each $R^1$ independently of one another represents hydrogen, $C_1$-$C_4$ alkyl or $C_1$-$C_4$ haloalkyl;

each $R^2$ is independently selected from the group of hydrogen, $C_1$-$C_8$ alkyl, $C_3$-$C_8$ cycloalkyl, $C_3$-$C_8$ cycloalkenyl, $C_2$-$C_8$ alkenyl, $C_2$-$C_8$ alkynyl and benzyl wherein the alkyl, cycloalkyl, cycloalkenyl, alkenyl, alkynyl and benzyl are optionally substituted by one or more groups independently selected from halogen, CN, $NH_2$, $NO_2$, OH, $C_1$-$C_4$ alkyl, $C_1$-$C_4$ haloalkyl, $C_1$-$C_4$ alkoxy and $C_1$-$C_4$ haloalkoxy;

each $R^3$ independently of one another represents hydrogen, $C_1$-$C_4$ alkyl, $C_3$-$C_4$ alkenyl, $C_3$-$C_4$ alkynyl or $COR^2$; wherein when two radicals $R^3$ are attached to the same nitrogen atom, these radicals can be identical or different; and wherein when two radicals $R^3$ are attached to the same nitrogen atom, these two radicals together with the nitrogen atom to which they are attached may form a cycle B-1, B-2, B-5, or B-8, wherein the cycle formed is optionally substituted by one or more groups independently selected from halogen, methyl and halomethyl;

$R^4$, $R^5$, $R^6$ and $R^7$ independently of one another represent hydrogen, halogen, cyano, $C_1$-$C_4$ alkyl, $C_1$-$C_4$ alkoxy, $C_3$-$C_5$ cycloalkyl, $C_1$-$C_4$ haloalkyl or $C_1$-$C_4$ alkylthio;

$R^8$ represents hydrogen, $C_1$-$C_8$ alkyl, $C_1$-$C_8$ haloalkyl, $C_3$-$C_8$ cycloalkyl, $C_3$-$C_8$ alkenyl, $C_3$-$C_8$ alkynyl or $C_1$-$C_8$ alkoxy-$C_1$-$C_8$ alkyl;

$V_1$ is hydrogen and $V_2$ is selected from hydrogen and $C_1$-$C_4$-alkylcarbonyl;

$V_3$ is selected from hydrogen, halogen, $C_1$-$C_6$ alkyl, $C_1$-$C_4$ haloalkyl, phenyl, benzyl or amino;

$V_4$ is selected from hydrogen, $C_1$-$C_4$ alkyl, $C_2$-$C_4$ alkenyl, phenyl-$C_1$-$C_2$-alkyl or $C_3$-$C_8$ cycloalkyl.

Preferably in this group of compounds, $Y_1$ represents hydrogen, halogen, CN, $NO_2$, $C_1$-$C_6$ alkyl, $C_3$-$C_8$ cycloalkyl, $C_2$-$C_6$ alkenyl, phenyl, naphthyl, a 5- to 10-membered mono- or bicyclic heterocycle containing one to three heteroatoms independently selected from O, S and N, providing that the heterocycle does not contain adjacent oxygen atoms, adjacent sulphur atoms, or adjacent sulphur and oxygen atoms, wherein the heterocycle can be aromatic, or fully or partially saturated, $CO_2R^1$, $COR^2$, $N(R^3)_2$ and $C(R^2)=N-OR^1$, wherein the alkyl, cycloalkyl, alkenyl, phenyl, naphthyl and heterocycle are optionally substituted by one or more groups independently selected from halogen, CN, OH, $NH_2$, SH, $NO_2$, $OR^1$, $C_1$-$C_4$ alkyl, $C_1$-$C_4$ haloalkyl, $C_1$-$C_4$ alkylthio, $C_1$-$C_4$ alkylsulphinyl and $C_1$-$C_4$ alkylsulphonyl;

$Y_2$ and $Y_3$ are independently selected from hydrogen, halogen, CN, methyl, ethyl, ethynyl, halomethyl, haloethyl, methoxy, halomethoxy, amino, methylamino, dimethylamino, pyrrolidino, piperidino, morpholino, methylthio, halomethylthio, methylsulfinyl and methylsulfonyl;

G represents a direct bond, C(O), $C(R^4)(R^5)$, $C(R^4)(R^5)$—$C(R^6)(R^7)$ or $C(R^4)=C(R^5)$;

each $R^1$ independently of one another represents hydrogen, $C_1$-$C_4$ alkyl or $C_1$-$C_4$ haloalkyl;

each $R^2$ is independently selected from the group of hydrogen, $C_1$-$C_8$ alkyl, $C_3$-$C_8$ cycloalkyl, $C_3$-$C_8$ cycloalkenyl, $C_2$-$C_8$ alkenyl, $C_2$-$C_8$ alkynyl and benzyl wherein the alkyl, cycloalkyl, cycloalkenyl, alkenyl, alkynyl and benzyl are optionally substituted by one or more groups independently selected from halogen, CN, $NH_2$, $NO_2$, OH, $C_1$-$C_4$ alkyl, $C_1$-$C_4$ haloalkyl, $C_1$-$C_4$ alkoxy and $C_1$-$C_4$ haloalkoxy;

each $R^3$ independently of one another represents hydrogen, $C_1$-$C_4$ alkyl, $C_3$-$C_4$ alkenyl, $C_3$-$C_4$ alkynyl or $COR^2$; wherein when two radicals $R^3$ are attached to the same nitrogen atom, these radicals can be identical or different; and wherein when two radicals $R^3$ are attached to the same nitrogen atom, these two radicals together with the nitrogen atom to which they are attached may form a cycle B-1, B-2, B-5, or B-8, wherein the cycle formed is optionally substituted by one or more groups independently selected from halogen, methyl and halomethyl;

$R^4$, $R^5$, $R^6$ and $R^7$ independently of one another represent hydrogen, halogen, cyano, $C_1$-$C_4$ alkyl, $C_1$-$C_4$ alkoxy, $C_3$-$C_5$ cycloalkyl, $C_1$-$C_4$ haloalkyl, or $C_1$-$C_4$ alkylthio;

$R^8$ represents hydrogen, $C_1$-$C_8$ alkyl, $C_1$-$C_8$ haloalkyl, $C_3$-$C_8$ cycloalkyl, $C_3$-$C_8$ alkenyl, $C_3$-$C_8$ alkynyl or $C_1$-$C_8$ alkoxy-$C_1$-$C_8$ alkyl;

$V_1$ is hydrogen and $V_2$ is selected from hydrogen and $C_1$-$C_4$-alkylcarbonyl;

$V_3$ is selected from hydrogen, halogen, $C_1$-$C_6$ alkyl, $C_1$-$C_4$ haloalkyl, phenyl, benzyl or amino;

$V_4$ is selected from hydrogen, $C_1$-$C_4$ alkyl, $C_2$-$C_4$ alkenyl, phenyl-$C_1$-$C_2$-alkyl, cyclopropyl, cyclopentyl or cyclohexyl.

Even more preferably in this group of compounds, $Y_1$ represents hydrogen, halogen, CN, $NO_2$, $C_1$-$C_4$ alkyl, $C_3$-$C_8$ cycloalkyl, $C_2$-$C_6$ alkenyl, phenyl, naphthyl, a 5- to 10-membered mono- or bicyclic heterocycle containing one to three heteroatoms independently selected from O, S and N, providing that the heterocycle does not contain adjacent oxygen atoms, adjacent sulphur atoms, or adjacent sulphur and oxygen atoms, wherein the heterocycle can be aromatic, or fully or partially saturated, $CO_2H$, $C_1$-$C_4$ alkoxycarbonyl, $C_1$-$C_4$ alkylcarbonyl, $NH_2$, $NH(C_1$-$C_4$ alkyl) and $N(C_1$-$C_4$ alkyl$)_2$, wherein the alkyl, cycloalkyl, alkenyl, phenyl, naphthyl and heterocycle are optionally substituted by one or more groups independently selected from halogen, CN, OH, $NH_2$, SH, $NO_2$, $C_1$-$C_4$ alkoxy, $C_1$-$C_4$ alkyl and $C_1$-$C_4$ haloalkyl;

$Y_2$ and $Y_3$ are hydrogen;

G represents a direct bond, C(O), $C(R^4)(R^5)$, $C(R^4)(R^5)$—$C(R^6)(R^7)$, or $C(R^4)$=$C(R^5)$;

$R^4$, $R^5$, $R^6$ and $R^7$ each represent hydrogen;

$V_1$ and $V_2$ are hydrogen;

$V_3$ is selected from hydrogen, halogen, $C_1$-$C_6$ alkyl, $C_1$-$C_4$ haloalkyl or amino;

$V_4$ is selected from hydrogen, $C_1$-$C_4$ alkyl, $C_2$-$C_4$ alkenyl, cyclopropyl, cyclopentyl or cyclohexyl.

In another preferred group of compounds, $Y_1$ represents hydrogen, halogen, CN, $C_1$-$C_6$ alkyl, $C_3$-$C_8$ cycloalkenyl, $C_2$-$C_6$ alkenyl, $C_2$-$C_6$ alkynyl, phenyl, a 5- to 10-membered mono- or bicyclic heterocycle containing one or two heteroatoms independently selected from O, S and N, providing that the heterocycle does not contain adjacent oxygen atoms, adjacent sulphur atoms, or adjacent sulphur and oxygen atoms, wherein the heterocycle can be aromatic, or fully or partially saturated, $C_1$-$C_4$ alkoxy, $C_1$-$C_4$ alkoxycarbonyl, $C_1$-$C_4$ alkylcarbonyl, $C_1$-$C_4$ alkenylcarbonyl and $C(R^2)$=N—$OR^1$, wherein the alkyl, cycloalkenyl, alkenyl, alkynyl, phenyl, benzyl and heterocycle are optionally substituted by one or more groups independently selected from halogen, $NH_2$, $NHCO(C_1$-$C_4$ alkyl), $C_1$-$C_4$ alkoxy, $C_1$-$C_4$ alkyl, $C_1$-$C_4$ haloalkyl, phenyl, halophenyl, $C_1$-$C_4$ alkylphenyl and $C_3$-$C_6$ cycloalkyl;

$Y_2$ and $Y_3$ are independently selected from hydrogen and halogen;

each $R^1$ is independently selected from hydrogen, $C_1$-$C_8$ alkyl, $C_3$-$C_8$ cycloalkyl, $C_3$-$C_8$ cycloalkyl-$C_1$-$C_2$ alkyl, $C_3$-$C_8$ cycloalkenyl, $C_3$-$C_8$ alkenyl, $C_3$-$C_8$ alkynyl, phenyl, benzyl or a 5- or 6-membered heterocycle containing one to two heteroatoms independently selected from O, S and N, providing that the heterocycle does not contain adjacent oxygen atoms, adjacent sulphur atoms, or adjacent sulphur and oxygen atoms, wherein the alkyl, cycloalkyl, cycloalkenyl, alkenyl, alkynyl, phenyl, benzyl and heterocycle are optionally substituted by one or more groups independently selected from halogen, CN, OH, $NH_2$, $NO_2$, SH, $C_1$-$C_4$ alkyl, $C_1$-$C_4$ haloalkyl, $C_1$-$C_4$ alkoxy, $C_1$-$C_4$ haloalkoxy and $C_1$-$C_4$ alkoxycarbonyl, and wherein the heterocycle may be attached to the rest of the molecule via a $C_1$-$C_2$ alkylene moiety;

$R^2$ independently of one another represents hydrogen, $C_1$-$C_4$ alkyl or $C_1$-$C_4$ haloalkyl;

$V_1$ and $V_2$ are independently selected from hydrogen and $C_1$-$C_4$-alkylcarbonyl, or $V_1$ and $V_2$ together with the nitrogen atom to which they are attached may form the cycle B-10;

$V_3$ is selected from hydrogen, halogen, $C_1$-$C_6$ alkyl, $C_1$-$C_4$ haloalkyl, phenyl, benzyl, $C_3$-$C_8$ cycloalkyl, or amino;

$V_4$ is selected from hydrogen, $C_1$-$C_4$ alkyl, $C_1$-$C_4$ haloalkyl, $C_3$-$C_4$ alkenyl, phenyl-$C_1$-$C_2$-alkyl or $C_3$-$C_8$ cycloalkyl;

G represents a direct bond, C(O), $C(R^4)(R^5)$, $C(R^4)(R^5)$—$C(R^6)(R^7)$ or $C(R^4)$=$C(R^5)$.

In another group of compounds, $Y_1$ represents hydrogen, halogen, CN, $C_1$-$C_6$ alkyl, $C_3$-$C_8$ cycloalkenyl, $C_2$-$C_6$ alkenyl, $C_2$-$C_6$ alkynyl, phenyl, a 5- to 10-membered mono- or bicyclic heterocycle containing one or two heteroatoms independently selected from O, S and N, providing that the heterocycle does not contain adjacent oxygen atoms, adjacent sulphur atoms, or adjacent sulphur and oxygen atoms, wherein the heterocycle can be aromatic, or fully or partially saturated, $C_1$-$C_4$ alkoxy, $C_1$-$C_4$ alkoxycarbonyl, $C_1$-$C_4$ alkenylcarbonyl and $C(R^2)$=N—$OR^1$, wherein the alkyl, cycloalkenyl, alkenyl, alkynyl, phenyl, benzyl and heterocycle are optionally substituted by one or more groups independently selected from halogen, $NH_2$, $NHCO(C_1$-$C_4$ alkyl), $C_1$-$C_4$ alkoxy, $C_1$-$C_4$ alkyl, $C_1$-$C_4$ haloalkyl, phenyl, halophenyl, $C_1$-$C_4$ alkylphenyl and $C_3$-$C_6$ cycloalkyl;

$Y_2$ and $Y_3$ are preferably independently selected from hydrogen and bromine;

G represents a direct bond, $C(R^4)(R^5)$, $C(R^4)(R^5)$—$C(R^6)(R^7)$ or $C(R^4)$=$C(R^5)$;

each $R^1$ is independently selected from hydrogen, $C_1$-$C_8$ alkyl, $C_3$-$C_6$ cycloalkyl-$C_1$-$C_2$ alkyl, $C_3$-$C_6$ alkenyl, phenyl, benzyl, pyridyl or pyridyl-$C_1$-$C_2$ alkyl wherein the alkyl, cycloalkyl, alkenyl, phenyl, benzyl and pyridyl are optionally substituted by one or more groups independently selected from halogen, CN, OH, $NH_2$, $NO_2$, SH, $C_1$-$C_4$ alkyl, $C_1$-$C_4$ haloalkyl, $C_1$-$C_4$ alkoxy, $C_1$-$C_4$ haloalkoxy and $C_1$-$C_4$ alkoxycarbonyl;

each $R^2$ independently of one another represents hydrogen, $C_1$-$C_4$ alkyl or $C_1$-$C_4$ haloalkyl;

$V_1$ is hydrogen;

$V_2$ is selected from hydrogen and $C_1$-$C_4$-alkylcarbonyl;

or $V_1$ and $V_2$ together with the nitrogen atom to which they are attached may form the cycle B-10;

$V_3$ is selected from hydrogen, halogen, $C_1$-$C_6$ alkyl, $C_1$-$C_4$ haloalkyl or cyclopropyl;

$V_4$ is selected from hydrogen, $C_1$-$C_4$ alkyl, $C_1$-$C_4$ haloalkyl, $C_3$-$C_4$ alkenyl, phenyl-$C_1$-$C_2$-alkyl, cyclopropyl, cyclopentyl or cyclohexyl.

In one group of compounds, $Y^1$ is $C(R^2)$=N—$OR^1$ wherein $R^1$ and $R^2$ are as defined herein.

Intermediates that can be used to prepare compounds of formula (I) also form part of the present invention.

Accordingly, in a further aspect, the invention provides novels compound of formula (L-V)

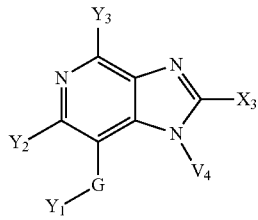

(L-V)

wherein $Y_1$ represents halogen, CN, $NO_2$, $C_1$-$C_6$ alkyl, $C_3$-$C_8$ cycloalkyl, $C_3$-$C_8$ cycloalkenyl, $C_2$-$C_6$ alkenyl, $C_2$-$C_6$ alkynyl, phenyl, naphthyl, a 5- to 10-membered mono- or bicyclic heterocycle containing one to three heteroatoms independently selected from O, S and N, providing that the heterocycle does not contain adjacent oxygen atoms, adjacent sulphur atoms, or adjacent sulphur and oxygen atoms, wherein the heterocycle can be aromatic, or fully or partially saturated, $OR^1$, $CO_2R^1$, $COR^2$, $CON(R^3)_2$, $N(R^3)_2$, $NR^3COR^2$ and $C(R^2)=N-OR^1$, wherein the alkyl, cycloalkyl, cycloalkenyl, alkenyl, alkynyl, phenyl, naphthyl, and heterocycle are optionally substituted by one or more groups independently selected from halogen, CN, OH, $NH_2$, $NR^3COR^2$, SH, $NO_2$, $OR^1$, $C_1$-$C_4$ alkyl, $C_1$-$C_4$ haloalkyl, phenyl, halophenyl, $C_1$-$C_4$ alkylphenyl, $C_3$-$C_8$ cycloalkyl, $C_3$-$C_8$ cycloalkenyl, $C_1$-$C_4$ alkylthio, $C_1$-$C_4$ alkylsulphinyl and $C_1$-$C_4$ alkylsulphonyl;

$Y_2$ and $Y_3$ are independently selected from hydrogen, halogen, CN, $NO_2$, $C_1$-$C_8$ alkyl, $C_3$-$C_8$ cycloalkyl, $C_3$-$C_8$ cycloalkenyl, $C_2$-$C_8$ alkenyl, $C_2$-$C_8$ alkynyl, phenyl, phenyl-$C_1$-$C_6$-alkyl, a 5- or 6-membered heterocycle containing one to three heteroatoms independently selected from O, S and N, providing that the heterocycle does not contain adjacent oxygen atoms, adjacent sulphur atoms, or adjacent sulphur and oxygen atoms, $OR^1$, $COR^2$, SH, $C_1$-$C_8$ alkylthio, $C_1$-$C_8$ alkylsulphinyl, $C_1$-$C_8$ alkylsulphonyl, phenylthio, phenylsulphinyl, phenylsulphonyl, $N(R^3)_2$, $CO_2R^1$, $O(CO)R^2$, $CON(R^3)_2$, $NR^3COR^2$ and $C(R^2)=N-OR^1$, wherein the alkyl, cycloalkyl, cycloalkenyl, alkenyl, alkynyl, phenyl, benzyl, and heterocycle are optionally substituted by one or more groups independently selected from halogen, CN, OH, $NH_2$, SH, $NO_2$, $OR^1$, $C_1$-$C_4$ alkyl, $C_1$-$C_4$ haloalkyl, $C_1$-$C_4$ alkylthio, $C_1$-$C_4$ alkylsulphinyl and $C_1$-$C_4$ alkylsulphonyl;

$V_4$ is selected from OH, $C_1$-$C_8$ alkyl, $C_1$-$C_8$ alkoxy, $C_3$-$C_8$ alkenyl, $C_3$-$C_8$ alkenyloxy, $C_3$-$C_8$ cycloalkyl, $C_3$-$C_8$ cycloalkenyl, $C_3$-$C_8$ cycloalkoxy, $C_3$-$C_8$ alkynyl, $C_3$-$C_8$ alkynyloxy, phenyl, phenyl-$C_1$-$C_6$-alkyl, benzyloxy, pyridyl, pyridyl-$C_1$-$C_6$-alkyl, $COR^2$, $CO_2R^2$, $CON(R^3)_2$ and $SO_2$—$C_1$-$C_8$-alkyl, wherein the alkyl, alkenyl, alkynyl, cycloalkyl, cycloalkenyl, phenyl, benzyl and pyridyl are optionally substituted by one or more groups independently selected from halogen, CN, $NH_2$, $NO_2$, OH, $C_1$-$C_4$ alkyl, $C_1$-$C_4$ haloalkyl, $C_1$-$C_4$ alkoxy and $C_1$-$C_4$ haloalkoxy;

$X_3$ is selected from Cl, Br, I, methylsulfonyl, ethylsulfonyl, n-propylsulfonyl, isopropylsulfonyl, ethylthio, n-propylthio and isopropylthio;

G, $R^1$, $R^2$, $R^3$, $R^4$, $R^5$, $R^6$, $R^7$, $R^8$, $V_1$, $V_2$ and $V_3$ are as defined for a compound of formula (I);

wherein when G is a direct bond, $Y_1$ cannot be hydrogen;

or a compound of formula (L-V) wherein $Y_1$, $Y_2$ and $Y_3$ each represent hydrogen;

$V_4$ is selected from OH, $C_1$-$C_8$ alkyl, $C_1$-$C_8$ alkoxy, $C_3$-$C_8$ alkenyl, $C_3$-$C_8$ alkenyloxy, $C_3$-$C_8$ cycloalkyl, $C_3$-$C_8$ cycloalkenyl, $C_3$-$C_8$ cycloalkoxy, $C_3$-$C_8$ alkynyl, $C_3$-$C_8$ alkynyloxy, phenyl, phenyl-$C_1$-$C_6$-alkyl, benzyloxy, pyridyl, pyridyl-$C_1$-$C_6$-alkyl, $COR^2$, $CO_2R^2$, $CON(R^3)_2$ and $SO_2$—$C_1$-$C_8$-alkyl, wherein the alkyl, alkenyl, alkynyl, cycloalkyl, cycloalkenyl, phenyl, benzyl and pyridyl are optionally substituted by one or more groups independently selected from halogen, CN, $NH_2$, $NO_2$, OH, $C_1$-$C_4$ alkyl, $C_1$-$C_4$ haloalkyl, $C_1$-$C_4$ alkoxy and $C_1$-$C_4$ haloalkoxy;

X is selected from Cl, Br, I, methylsulfonyl, ethylsulfonyl, n-propylsulfonyl, isopropylsulfonyl, ethylthio, n-propylthio and isopropylthio, provided that the compound is not one of the following compounds:

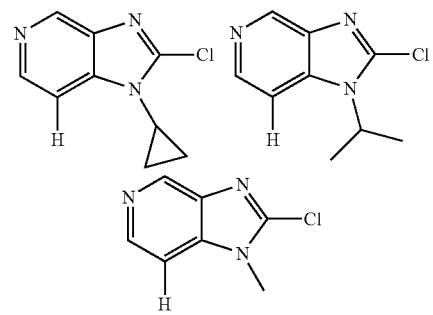

or agriculturally acceptable tautomers, salts or N-oxides thereof.

In a further aspect, the invention provides a compound of the formula (L-VIII):

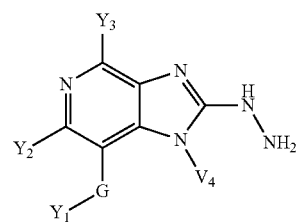

(L-VIII)

wherein G, $Y_1$, $Y_2$, $Y_3$ and $V_4$ are defined as in claim 1 or agriculturally acceptable tautomers, salts or N-oxides thereof, and provided that the compound is not

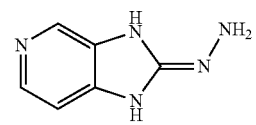 [SMILES: N/N=c1/[nH]c2ccncc2[nH]1]

The compounds of formula (I) may exist as different geometric or optical isomers or in different tautomeric forms. These may be separated and isolated by well-known (usually chromatographic) techniques, and all such isomers and tautomers and mixtures thereof in all proportions as well as isotopic forms, such as deuterated compounds, are part of the present invention.

The compounds of the invention can be used in their free form or as a salt thereof. Acids that can be used for the preparation of salts are as follows: hydrofluoric, hydrochloric, hydrobromic, hydroiodic, sulfuric, phosphoric, nitric, acetic, trifluoroacetic, trichloroacetic, prioprionic, glycolic, thiocyanic, lactic, succinic, citric, benzoic, cinnamic, oxalic, formic, benzenesulfonic, p-toluenesulfonic, methanesulfonic, salicylic, p-aminosalicylic, 2-phenoxybenzoic, 2-acetoxybenzoic and 1,2-naphthalene-disulfonic acid The compounds in Tables 1 to 12 illustrate compounds of formula (I).

Table X represents Table 1 (when X is 1), Table 2 (when X is 2), Table 3 (when X is 3), Table 4 (when X is 4), Table 5 (when X is 5), Table 6 (when X is 6), Table 7 (when X is 7), Table 8 (when X is 8), Table 9 (when X is 9), Table 10 (when X is 10), Table 11 (when X is 11), Table 12 (when X is 12), Table 13 (when X is 13), Table 14 (when X is 14), Table 15 (when X is 15), Table 16 (when X is 16)

TABLE X

|  | $Y_1$ | $Y_2$ | $Y_3$ | $V_3$ | $V_4$ |
|---|---|---|---|---|---|
| X.001 | H | H | H | H | H |
| X.002 | H | H | H | H | $CH_3$ |
| X.003 | H | H | H | H | $CH_2CH_3$ |
| X.004 | H | H | H | H | $CH_2CH_2CH_3$ |
| X.005 | H | H | H | H | $CH_2CH_2CH_2CH_3$ |
| X.006 | H | H | H | H | $CH(CH_3)_2$ |
| X.007 | H | H | H | H | $CH_2CH(CH_3)_2$ |
| X.008 | H | H | H | H | $CH(CH_3)CH_2CH_3$ |
| X.009 | H | H | H | H | cyclopropyl |
| X.010 | H | H | H | H | —$CH_2$-cyclopropyl |
| X.011 | H | H | H | H | cyclobutyl |
| X.012 | H | H | H | H | cyclopentyl |
| X.013 | H | H | H | H | cyclopent-3-enyl |
| X.014 | H | H | H | H | 3-methylcyclohexyl |
| X.015 | H | H | H | H | 4-methylcyclohexyl |
| X.016 | H | H | H | H | 1-methylcyclohexyl |
| X.017 | H | H | H | H | cyclohexyl |
| X.018 | H | H | H | H | cyclohex-3-enyl |
| X.019 | H | H | H | H | 4-methylcyclohex-3-enyl |
| X.020 | H | H | H | H | $CH_2CH{=}CH_2$ |
| X.021 | H | H | H | H | $CH(CH_3)CH{=}CH_2$ |
| X.022 | H | H | H | H | $CH_2CH{=}CH(CH_3)$ |
| X.023 | H | H | H | H | $CH_2CH{=}CH(CH_3)$ E |
| X.024 | H | H | H | H | $CH_2CH{=}CH(CH_3)$ Z |
| X.025 | H | H | H | H | $CH_2CH{=}C(CH_3)_2$ |
| X.026 | H | H | H | H | $CH_2C{\equiv}CH$ |
| X.027 |  |  |  |  | $CH(CH_3)C{\equiv}CH$ |
| X.028 | H | H | H | H | $CH_2C{\equiv}CCH_3$ |
| X.029 | H | H | H | H | $CH_2C{\equiv}CC(CH_3)_3$ |
| X.030 | H | H | H | H | $CH_2C{\equiv}CC(CH_3)_3$ |
| X.031 | H | H | H | H | $CH_2$phenyl |
| X.032 | H | H | H | H | $CH_2$-4-$CH_3$-phenyl |
| X.033 | H | H | H | H | $CH_2$-2-$CH_3$-phenyl |
| X.034 | H | H | H | H | $CH_2OCH_3$ |
| X.035 | H | H | H | H | $CH_2CH_2OCH_3$ |
| X.036 | H | H | H | H | $CH_2CH_2OCH_2CH_3$ |
| X.037 | H | H | H | H | oxan-2-yl |
| X.038 | H | H | H | H | oxetan-2-yl |
| X.039 | H | H | H | H | OH |
| X.040 | H | H | H | H | $OCH_3$ |
| X.041 | H | H | H | H | $OCH_2CH_3$ |
| X.042 | H | H | H | H | $OCH_2$-phenyl |
| X.043 | H | H | H | H | $OCH_2CH{=}CH_2$ |
| X.044 | H | H | H | H | $OCH_2C{\equiv}CH$ |
| X.045 | H | H | H | H | $CH_2$phenyl |
| X.046 | H | H | H | H | $CH_2CH_2$phenyl |
| X.047 | H | H | H | H | $CH_2CH_2$-2-$CH_3$-phenyl |
| X.048 | H | H | H | H | $CH_2CH_2$-3-$CH_3$-phenyl |
| X.049 | H | H | H | H | $CH_2CH_2$-4-$CH_3$-phenyl |
| X.050 | H | H | H | H | $CH_2CH_2$-2-F-phenyl |
| X.051 | H | H | H | H | $CH_2CH_2$-3,5-di-Cl-phenyl |
| X.052 | H | H | H | H | $CH_2$-4-$CH_3$-phenyl |
| X.053 | H | H | H | H | $CH_2$-2-$CH_3$-phenyl |
| X.054 | H | H | H | H | $CH_2$-3-$CH_3$-phenyl |
| X.055 | H | H | H | H | $CH_2$-4-Cl-phenyl |
| X.056 | H | H | H | H | $CH_2$-2-Cl-phenyl |
| X.057 | H | H | H | H | $CH_2$-3-Cl-phenyl |
| X.058 | H | H | H | H | $CH_2CH_2$-2-Cl-phenyl |
| X.059 | H | H | H | H | $CH_2CH_2$-3-Cl-phenyl |
| X.060 | H | H | H | H | $CH_2CH_2$-4-Cl-phenyl |
| X.061 | H | H | H | H | $CH_2CH_2$-3,5-di-Cl-phenyl |
| X.062 | H | H | H | $CH_3$ | $CH_2CH_3$ |
| X.063 | H | H | H | $CH_2CH_3$ | $CH_2CH_3$ |
| X.064 | H | H | H | $CH_2CH_2CH_3$ | $CH_2CH_3$ |
| X.065 |  |  | H | $CH_2CH_2CH_2CH_3$ | $CH_2CH_3$ |
| X.066 | H | H | H | $CH(CH_3)_2$ | $CH_2CH_3$ |
| X.067 |  |  | H | $C(CH_3)_3$ | $CH_2CH_3$ |

TABLE X-continued

| | $Y_1$ | $Y_2$ | $Y_3$ | $V_3$ | $V_4$ |
|---|---|---|---|---|---|
| X.068 | H | H | H | cyclopropyl | $CH_2CH_3$ |
| X.069 | H | H | H | $(CH_2)_4CH_3$ | $CH_2CH_3$ |
| X.070 | H | H | H | cyclohexyl | $CH_2CH_3$ |
| X.071 | H | H | H | $CF_3$ | $CH_2CH_3$ |
| X.072 | H | H | H | $CHF_2$ | $CH_2CH_3$ |
| X.073 | H | H | H | benzyl | $CH_2CH_3$ |
| X.074 | H | H | H | Cl | $CH_2CH_3$ |
| X.075 | | | | Br | $CH_2CH_3$ |
| X.076 | H | H | H | CN | $CH_2CH_3$ |
| X.077 | H | H | H | $CH_2CH_2CN$ | $CH_2CH_3$ |
| X.078 | H | H | H | $C_6H_5$ | $CH_2CH_3$ |
| X.079 | H | H | H | 4-Cl—$C_6H_4$ | $CH_2CH_3$ |
| X.080 | H | H | H | 3-F—$C_6H_4$ | $CH_2CH_3$ |
| X.081 | H | H | H | 2-$CH_3$—$C_6H_4$ | $CH_2CH_3$ |
| X.082 | H | H | H | 3,5-di-F—$C_6H_3$ | $CH_2CH_3$ |
| X.083 | H | H | H | $NH_2$ | $CH_2CH_3$ |
| X.084 | H | H | H | $NMe_2$ | $CH_2CH_3$ |
| X.085 | H | H | H | $CH_3$ | cyclohexyl |
| X.086 | H | H | H | $CH_2CH_3$ | cyclohexyl |
| X.087 | H | H | H | $CH_2CH_2CH_3$ | cyclohexyl |
| X.088 | | | | $CH_2CH_2CH_2CH_3$ | cyclohexyl |
| X.089 | H | H | H | $CH(CH_3)_2$ | cyclohexyl |
| X.090 | H | H | H | $C(CH_3)_3$ | cyclohexyl |
| X.100 | H | H | H | cyclopropyl | cyclohexyl |
| X.101 | H | H | H | $(CH_2)_4CH_3$ | cyclohexyl |
| X.102 | H | H | H | cyclohexyl | cyclohexyl |
| X.103 | H | H | H | $CF_3$ | cyclohexyl |
| X.104 | H | H | H | $CHF_2$ | cyclohexyl |
| X.105 | H | H | H | benzyl | cyclohexyl |
| X.106 | H | H | H | Cl | cyclohexyl |
| X.107 | H | H | H | Br | cyclohexyl |
| X.108 | H | H | H | CN | cyclohexyl |
| X.109 | H | H | H | $CH_2CH_2CN$ | cyclohexyl |
| X.110 | H | H | H | $C_6H_5$ | cyclohexyl |
| X.111 | H | H | H | 4-Cl—$C_6H_4$ | cyclohexyl |
| X.112 | H | H | H | 3-F—$C_6H_4$ | cyclohexyl |
| X.113 | H | H | H | 2-$CH_3$—$C_6H_4$ | cyclohexyl |
| X.114 | H | H | H | 3,5-di-F—$C_6H_3$ | cyclohexyl |
| X.115 | H | H | H | $NH_2$ | cyclohexyl |
| X.116 | H | H | H | $NMe_2$ | cyclohexyl |
| X.117 | H | H | H | $CH_3$ | cyclopropyl |
| X.118 | H | H | H | $CH_2CH_3$ | cyclopropyl |
| X.119 | H | H | H | $CH_2CH_2CH_3$ | cyclopropyl |
| X.120 | H | H | H | $CH_2CH_2CH_2CH_3$ | cyclopropyl |
| X.121 | H | H | H | $CH(CH_3)_2$ | cyclopropyl |
| X.122 | H | H | H | $C(CH_3)_3$ | cyclopropyl |
| X.123 | H | H | H | cyclopropyl | cyclopropyl |
| X.124 | H | H | H | $(CH_2)_4CH_3$ | cyclopropyl |
| X.125 | H | H | H | cyclohexyl | cyclopropyl |
| X.126 | H | H | H | $CF_3$ | cyclopropyl |
| X.127 | H | H | H | $CHF_2$ | cyclopropyl |
| X.128 | H | H | H | benzyl | cyclopropyl |
| X.129 | H | H | H | Cl | cyclopropyl |
| X.130 | H | H | H | Br | cyclopropyl |
| X.131 | H | H | H | CN | cyclopropyl |
| X.132 | H | H | H | $CH_2CH_2CN$ | cyclopropyl |
| X.133 | H | H | H | $C_6H_5$ | cyclopropyl |
| X.134 | H | H | H | 4-Cl—$C_6H_4$ | cyclopropyl |
| X.135 | H | H | H | 3-F—$C_6H_4$ | cyclopropyl |
| X.136 | H | H | H | 2-$CH_3$—$C_6H_4$ | cyclopropyl |
| X.137 | H | H | H | 3,5-di-F—$C_6H_3$ | cyclopropyl |
| X.138 | H | H | H | $NH_2$ | cyclopropyl |
| X.139 | H | H | H | $NMe_2$ | cyclopropyl |
| X.140 | H | H | H | $CH_3$ | $CH_3$ |
| X.141 | H | H | H | $CH_3$ | $CH_2CH_2CH_3$ |
| X.142 | H | H | H | $CH_3$ | $CH(CH_3)_2$ |
| X.143 | H | H | H | $CH_3$ | cyclopentyl |
| X.144 | H | H | H | $CH_3$ | $CH(CH_3)CH_2CH_3$ |
| X.145 | H | H | H | $CH_3$ | $CH_2CH=CH_2$ |
| X.146 | H | H | H | $CH_3$ | $CH_2CCH$ |
| X.147 | H | H | H | $CH_3$ | $CH_2C_6H_5$ |
| X.148 | H | H | H | $CH_3$ | $CH_2$-3-F-phenyl |
| X.149 | H | H | H | $CH_3$ | $CH(CH_3)$—$OCH_2CH_3$ |
| X.150 | H | H | H | $CH_3$ | $CH_2CH_2C_6H_5$ |
| X.151 | H | H | H | $CH_3$ | $CH_2CH_2$-4-Cl-phenyl |
| X.152 | $CH_3$ | H | H | H | $CH_3$ |
| X.153 | $CH_3$ | H | H | H | $CH_2CH_3$ |
| X.154 | $CH_3$ | H | H | H | $CH_2CH_2CH_3$ |

TABLE X-continued

| | $Y_1$ | $Y_2$ | $Y_3$ | $V_3$ | $V_4$ |
|---|---|---|---|---|---|
| X.155 | $CH_3$ | H | H | H | $CH(CH_3)_2$ |
| X.156 | $CH_3$ | H | H | H | $CH_2CH(CH_3)_2$ |
| X.157 | $CH_3$ | H | H | H | cyclopropyl |
| X.158 | $CH_3$ | H | H | H | cyclopentyl |
| X.159 | $CH_3$ | H | H | H | cyclohexyl |
| X.160 | $CH_2CH_3$ | H | H | H | $CH_3$ |
| X.161 | $CH_2CH_3$ | H | H | H | $CH_2CH_3$ |
| X.162 | $CH_2CH_3$ | H | H | H | $CH_2CH_2CH_3$ |
| X.163 | $CH_2CH_3$ | H | H | H | $CH(CH_3)_2$ |
| X.164 | $CH_2CH_3$ | H | H | H | $CH_2CH(CH_3)_2$ |
| X.165 | $CH_2CH_3$ | H | H | H | cyclopropyl |
| X.166 | $CH_2CH_3$ | H | H | H | cyclopentyl |
| X.167 | $CH_2CH_3$ | H | H | H | cyclohexyl |
| X.168 | $C_6H_5$ | H | H | H | H |
| X.169 | $C_6H_5$ | H | H | H | $CH_3$ |
| X.170 | $C_6H_5$ | H | H | H | $CH_2CH_3$ |
| X.171 | $C_6H_5$ | H | H | H | $CH_2CH_2CH_3$ |
| X.172 | $C_6H_5$ | H | H | H | $CH(CH_3)_2$ |
| X.173 | $C_6H_5$ | H | H | H | $CH_2CH(CH_3)_2$ |
| X.174 | $C_6H_5$ | H | H | H | cyclopropyl |
| X.175 | $C_6H_5$ | H | H | H | cyclopentyl |
| X.176 | $C_6H_5$ | H | H | H | cyclohexyl |
| X.177 | 2-Cl—$C_6H_4$ | H | H | H | $CH_3$ |
| X.178 | 2-Cl—$C_6H_4$ | H | H | H | $CH_2CH_3$ |
| X.179 | 2-Cl—$C_6H_4$ | H | H | H | $CH_2CH_2CH_3$ |
| X.180 | 4-Cl—$C_6H_4$ | H | H | H | $CH_3$ |
| X.181 | 4-Cl—$C_6H_4$ | H | H | H | $CH_2CH_3$ |
| X.182 | 4-Cl—$C_6H_4$ | H | H | H | $CH_2CH_2CH_3$ |
| X.183 | 2,4-di-Cl—$C_6H_3$ | H | H | H | $CH_3$ |
| X.184 | 2,4-di-Cl—$C_6H_3$ | H | H | H | $CH_2CH_3$ |
| X.185 | 2,4-di-Cl—$C_6H_3$ | H | H | H | $CH_2CH_2CH_3$ |
| X.186 | 2-F—$C_6H_4$ | H | H | H | $CH_3$ |
| X.187 | 2-F—$C_6H_4$ | H | H | H | $CH_2CH_3$ |
| X.188 | 2-F—$C_6H_4$ | H | H | H | $CH_2CH_2CH_3$ |
| X.189 | 4-F—$C_6H_4$ | H | H | H | $CH_3$ |
| X.190 | 4-F—$C_6H_4$ | H | H | H | $CH_2CH_3$ |
| X.191 | 4-F—$C_6H_4$ | H | H | H | $CH_2CH_2CH_3$ |
| X.192 | 2,4-di-F—$C_6H_3$ | H | H | H | $CH_3$ |
| X.193 | 2,4-di-F—$C_6H_3$ | H | H | H | $CH_2CH_3$ |
| X.194 | 2,4-di-F—$C_6H_3$ | H | H | H | $CH_2CH_2CH_3$ |
| X.195 | 2,5-di-F—$C_6H_3$ | H | H | H | $CH_3$ |
| X.196 | 2,5-di-F—$C_6H_3$ | H | H | H | $CH_2CH_3$ |
| X.197 | 2,5-di-F—$C_6H_3$ | H | H | H | $CH_2CH_2CH_3$ |
| X.198 | 2,5-di-Cl—$C_6H_3$ | H | H | H | $CH_3$ |
| X.199 | 2,5-di-Cl—$C_6H_3$ | H | H | H | $CH_2CH_3$ |
| X.200 | 2,5-di-Cl—$C_6H_3$ | H | H | H | $CH_2CH_2CH_3$ |
| X.201 | 2-Cl-4-$CF_3$—$C_6H_3$ | H | H | H | $CH_3$ |
| X.202 | 2-Cl-4-$CF_3$—$C_6H_3$ | H | H | H | $CH_2CH_3$ |
| X.203 | 2-Cl-4-$CF_3$—$C_6H_3$ | H | H | H | $CH_2CH_2CH_3$ |
| X.204 | 4-$CF_3$—$C_6H_4$ | H | H | H | $CH_3$ |
| X.205 | 4-$CF_3$—$C_6H_4$ | H | H | H | $CH_2CH_3$ |
| X.206 | 4-$CF_3$—$C_6H_4$ | H | H | H | $CH_2CH_2CH_3$ |
| X.207 | 2-F-4-$CF_3$—$C_6H_3$ | H | H | H | $CH_3$ |
| X.208 | 2-F-4-$CF_3$—$C_6H_3$ | H | H | H | $CH_2CH_3$ |
| X.209 | 2-F-4-$CF_3$—$C_6H_3$ | H | H | H | $CH_2CH_2CH_3$ |
| X.210 | 2-Cl-4-$CH_3$—$C_6H_3$ | H | H | H | $CH_3$ |
| X.211 | 2-Cl-4-$CH_3$—$C_6H_3$ | H | H | H | $CH_2CH_3$ |
| X.212 | 2-Cl-4-$CH_3$—$C_6H_3$ | H | H | H | $CH_2CH_2CH_3$ |
| X.213 | 2-F-4-$CH_3$—$C_6H_3$ | H | H | H | $CH_3$ |
| X.214 | 2-F-4-$CH_3$—$C_6H_3$ | H | H | H | $CH_2CH_3$ |
| X.215 | 2-F-4-$CH_3$—$C_6H_3$ | H | H | H | $CH_2CH_2CH_3$ |
| X.216 | 2-Cl-4-$CH_3O$—$C_6H_3$ | H | H | H | $CH_3$ |
| X.217 | 2-Cl-4-$CH_3O$—$C_6H_3$ | H | H | H | $CH_2CH_3$ |
| X.218 | 2-Cl-4-$CH_3O$—$C_6H_3$ | H | H | H | $CH_2CH_2CH_3$ |
| X.219 | 2-F-4-$CH_3O$—$C_6H_3$ | H | H | H | $CH_3$ |
| X.220 | 2-F-4-$CH_3O$—$C_6H_3$ | H | H | H | $CH_2CH_3$ |
| X.221 | 2-F-4-$CH_3O$—$C_6H_3$ | H | H | H | $CH_2CH_2CH_3$ |
| X.222 | 2-$CH_3O$—$C_6H_4$ | H | H | H | $CH_3$ |
| X.223 | 2-$CH_3O$—$C_6H_4$ | H | H | H | $CH_2CH_3$ |
| X.224 | 2-$CH_3O$—$C_6H_4$ | H | H | H | $CH_2CH_2CH_3$ |
| X.225 | 2,4-di-$CH_3O$—$C_6H_3$ | H | H | H | $CH_3$ |
| X.226 | 2,4-di-$CH_3O$—$C_6H_3$ | H | H | H | $CH_2CH_3$ |
| X.227 | 2,4-di-$CH_3O$—$C_6H_3$ | H | H | H | $CH_2CH_2CH_3$ |
| X.228 | 2-$CH_3O$-4-Cl—$C_6H_3$ | H | H | H | $CH_3$ |
| X.229 | 2-$CH_3O$-4-Cl—$C_6H_3$ | H | H | H | $CH_2CH_3$ |
| X.230 | 2-$CH_3O$-4-Cl—$C_6H_3$ | H | H | H | $CH_2CH_2CH_3$ |
| X.231 | 2-$CH_3O$-4-F—$C_6H_3$ | H | H | H | $CH_3$ |
| X.232 | $CH_2CH_2CH_3$ | H | H | H | $CH_3$ |

TABLE X-continued

| | $Y_1$ | $Y_2$ | $Y_3$ | $V_3$ | $V_4$ |
|---|---|---|---|---|---|
| X.233 | $CH_2CH_2CH_3$ | H | H | H | $CH_2CH_3$ |
| X.234 | $CH_2CH_2CH_3$ | H | H | H | $CH_2CH_2CH_3$ |
| X.235 | $CH_2CH_2CH_3$ | H | H | H | $CH(CH_3)_2$ |
| X.236 | $CH_2CH_2CH_3$ | H | H | H | $CH_2CH(CH_3)_2$ |
| X.237 | $CH_2CH_2CH_3$ | H | H | H | cyclopropyl |
| X.238 | $CH_2CH_2CH_3$ | H | H | H | cyclopentyl |
| X.239 | $CH_2CH_2CH_3$ | H | H | H | cyclohexyl |
| X.240 | $CH(CH_3)_2$ | H | H | H | $CH_3$ |
| X.241 | $CH(CH_3)_2$ | H | H | H | $CH_3$ |
| X.242 | $CH(CH_3)_2$ | H | H | H | $CH_2CH_3$ |
| X.243 | $CH(CH_3)_2$ | H | H | H | $CH_2CH_2CH_3$ |
| X.244 | $CH(CH_3)_2$ | H | H | H | $CH(CH_3)_2$ |
| X.245 | $CH(CH_3)_2$ | H | H | H | $CH_2CH(CH_3)_2$ |
| X.246 | $CH(CH_3)_2$ | H | H | H | cyclopropyl |
| X.247 | $CH(CH_3)_2$ | H | H | H | cyclopentyl |
| X.248 | $CH(CH_3)_2$ | H | H | H | cyclohexyl |

TABLE 1

This table discloses compounds 1.001 to 1.248 of the formula (I-I)

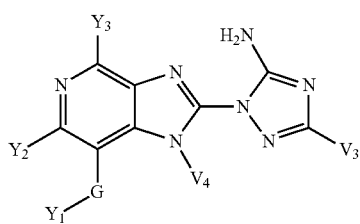

(I-I)

wherein G is a direct bond and $Y_1$, $Y_2$, $Y_3$, $V_3$ and $V_4$ have the specific meanings given in the Table

TABLE 2

This table discloses compounds 2.001 to 2.248 of the formula (I-II)

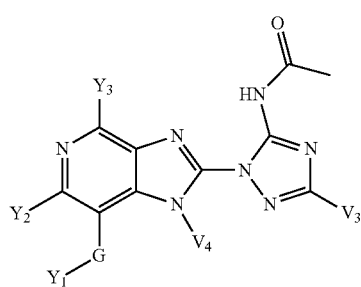

(I-II)

wherein G is a direct bond and $Y_1$, $Y_2$, $Y_3$, $V_3$ and $V_4$ have the specific meanings given in the Table

TABLE 3

This table discloses compounds 3.001 to 3.248 of the formula (I-III)

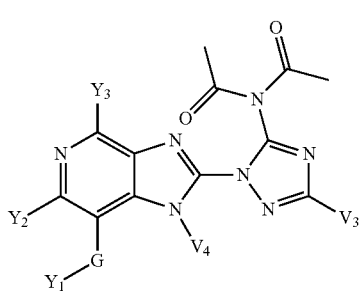

(I-III)

wherein G is a direct bond and $Y_1$, $Y_2$, $Y_3$, $V_3$ and $V_4$ have the specific meanings given in the Table

TABLE 4

This table discloses compounds 4.001 to 4.248 of the formula (I-IV)

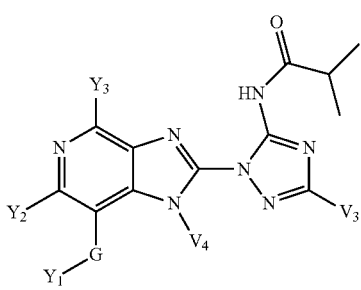

(I-IV)

wherein G is a direct bond and $Y_1$, $Y_2$, $Y_3$, $V_3$ and $V_4$ have the specific meanings given in the Table

TABLE 5

This table discloses compounds 5.001 to 5.248 of the formula (I-V)

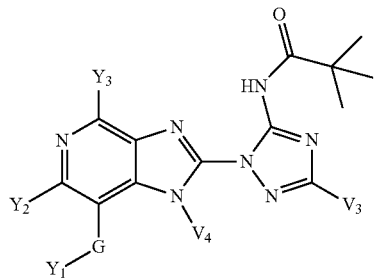

(I-V)

wherein G is a direct bond and $Y_1$, $Y_2$, $Y_3$, $V_3$ and $V_4$ have the specific meanings given in the Table

TABLE 6

This table discloses compounds 6.001 to 6.248 of the formula (I-VI)

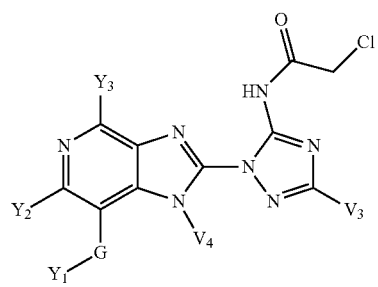

(I-VI)

wherein G is a direct bond and $Y_1$, $Y_2$, $Y_3$, $V_3$ and $V_4$ have the specific meanings given in the Table

TABLE 7

This table discloses compounds 7.001 to 7.248 of the formula (I-VII)

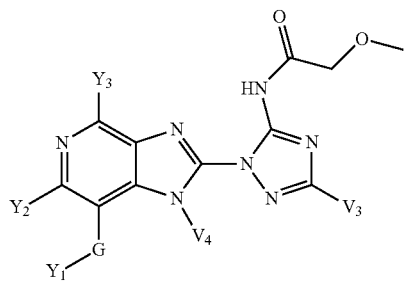

(I-VII)

wherein G is a direct bond and $Y_1$, $Y_2$, $Y_3$, $V_3$ and $V_4$ have the specific meanings given in the Table

TABLE 8

This table discloses compounds 8.001 to 8.248 of the formula (I-VIII)

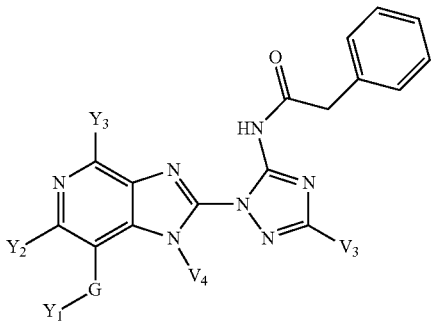

(I-VIII)

wherein G is a direct bond and $Y_1$, $Y_2$, $Y_3$, $V_3$ and $V_4$ have the specific meanings given in the Table

TABLE 9

This table discloses compounds 9.001 to 9.248 of the formula (I-IX)

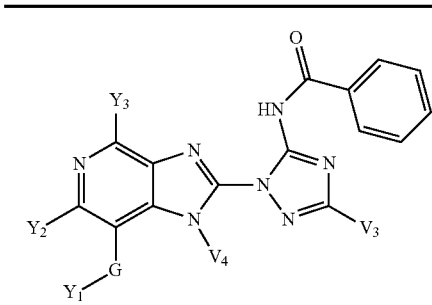

(I-IX)

wherein G is a direct bond and $Y_1$, $Y_2$, $Y_3$, $V_3$ and $V_4$ have the specific meanings given in the Table

TABLE 10

This table discloses compounds 10.001 to 10.248 of the formula (I-X)

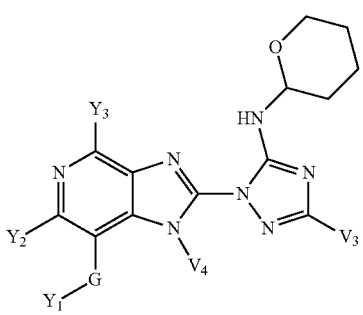

(I-X)

wherein G is a direct bond and $Y_1$, $Y_2$, $Y_3$, $V_3$ and $V_4$ have the specific meanings given in the Table

TABLE 11

This table discloses compounds 11.001 to 11.248 of the formula (I-XI)

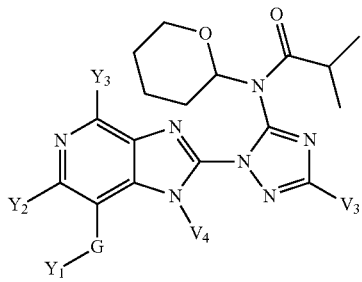

(I-XI)

wherein G is a direct bond and $Y_1$, $Y_2$, $Y_3$, $V_3$ and $V_4$ have the specific meanings given in the Table

TABLE 12

This table discloses compounds 12.001 to 12.248 of the formula (I-XII)

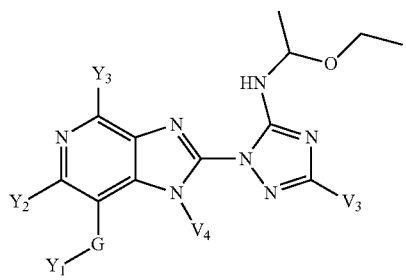

(I-XII)

wherein G is a direct bond and $Y_1$, $Y_2$, $Y_3$, $V_3$ and $V_4$ have the specific meanings given in the Table

TABLE 13

This table discloses compounds 13.001 to 13.248 of the formula (I-XIII)

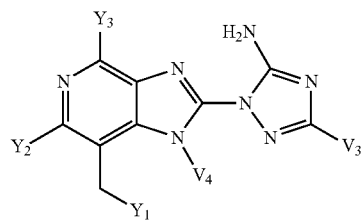

(I-XIII)

wherein $Y_1$, $Y_2$, $Y_3$, $V_3$ and $V_4$ have the specific meanings given in the Table

TABLE 14

This table discloses compounds 14.001 to 14.248 of the formula (I-XIV)

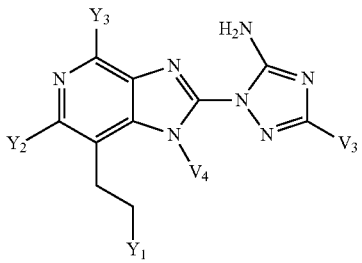

(I-XIV)

wherein $Y_1$, $Y_2$, $Y_3$, $V_3$ and $V_4$ have the specific meanings given in the Table

TABLE 15

This table discloses compounds 15.001 to 15.248 of the formula (I-XV)

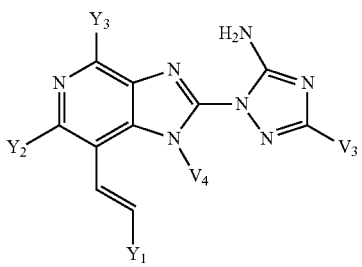

(I-XV)

wherein $Y_1$, $Y_2$, $Y_3$, $V_3$ and $V_4$ have the specific meanings given in the Table

TABLE 16

This table discloses compounds 16.001 to 16.248 of the formula (I-XVI)

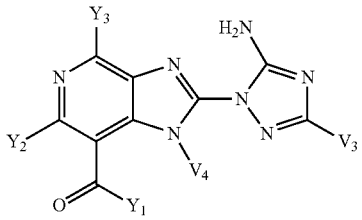

(I-XVI)

wherein $Y_1$, $Y_2$, $Y_3$, $V_3$ and $V_4$ have the specific meanings given in the Table The compounds in Tables 1 to 16 include all isomers, tautomers and mixtures thereof, including the cis/trans isomers shown above.

Compounds of Tables 1 to 16 can be prepared according to the following methods.

Scheme 1

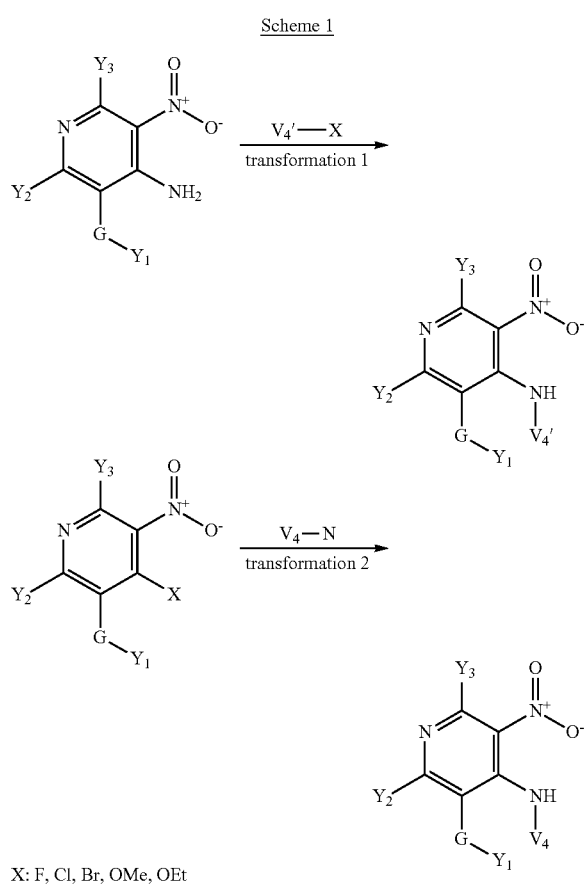

X: F, Cl, Br, OMe, OEt

In scheme 1, G, $Y_1$, $Y_2$, $Y_3$, $V_4$ have the meanings given above. The intermediates shown are either commercial or can easily be prepared from commercial starting materials.

Transformation 1

$V_4'$ represents $C_1$-$C_8$ alkyl, $C_2$-$C_8$ alkenyl, $C_3$-$C_8$ cycloalkyl, $C_3$-$C_8$ cycloalkenyl, $C_2$-$C_8$ alkynyl, phenyl, phenyl-$C_1$-$C_6$-alkyl, pyridyl, pyridyl-$C_1$-$C_6$-alkyl, $COR^2$ (wherein $R^2$ is defined as above) or $SO_2$—$C_1$-$C_8$-alkyl, wherein the alkyl, alkenyl, alkynyl, cycloalkyl, cycloalkenyl, phenyl, benzyl and pyridyl are optionally substituted by one or more groups independently selected from halogen, CN, $NH_2$, $NO_2$, OH, $C_1$-$C_4$ alkyl, $C_1$-$C_4$ haloalkyl, $C_1$-$C_4$ alkoxy and $C_1$-$C_4$ haloalkoxy. Here the $NH_2$ of the amino-nitro-pyridine is transformed into NH—$V_4'$ by electrophilic reagents $V_4'$—X whereby X is a halogen or a sulfonic acid ester group. The reaction is usually carried out in an inert solvent such as THF, dioxane, diethyl ether, NMP, DMF, DMPU, DMSO, sulfolane in the presence of bases such as sodium or potassium hydroxide, carbonate or tert-butoxide, or sodium hydride. Relevant literature references include: Bioorganic & Medicinal Chemistry, 16(3), 1511-1530; 2008; PCT Int. Appl., 2006013195; Nucleosides & Nucleotides, 10(1-3), 543-5; 1991; Tetrahedron, 65(44), 8950-8955; 2009; Tetrahedron, 65(44), 8950-8955; 2009

When $V_4'$ is $COR^2$, transformation 1 is an acylation of the amino group. This process is described in scheme 7, transformation 1 below.

When $V_4'$ is $SO_2$—$C_1$-$C_8$-alkyl then the process is an alkylsulfonylation of an amine a well-established reaction. Relevant literature references include Journal of Medicinal Chemistry, 48(18), 5823-5836; 2005 and WO 2006101321

Transformation 2

Here, the amino group is introduced by a nucleophilic substitution whereby the nucleophile $H_2N$—$V_4$ is displacing the leaving group X. Such nucleophilic substitutions can be done in a number of solvents such as water, methanol, butanol, tert-butanol, MeCN, DMF, NMP, DMSO and $CH_2Cl_2$. Often, the reaction is carried out in the presence of a base such as triethylamine, Hünig's base, inorganic bases such as sodium or potassium carbonate or bicarbonate. Relevant literature references include: Organic Process Research & Development, 12(6), 1261-1264; 2008; Organic Process Research & Development, 8(6), 903-908; 2004; Journal of Medicinal Chemistry, 38(20), 4131-4; 1995; Bioorganic & Medicinal Chemistry Letters, 19(5), 1508-1511; 2009; PCT Int. Appl., 2008056150, 15 May 2008; PCT Int. Appl., 2005011700, 10 Feb. 2005; European Journal of Medicinal Chemistry, 24(3), 227-32; 1989; PCT Int. Appl., 2005051324, 9 Jun. 2005; Bioorganic & Medicinal Chemistry, 14(12), 4029-4034; 2006; Journal of Heterocyclic Chemistry, 14(5), 813-21; 1977

Scheme 2

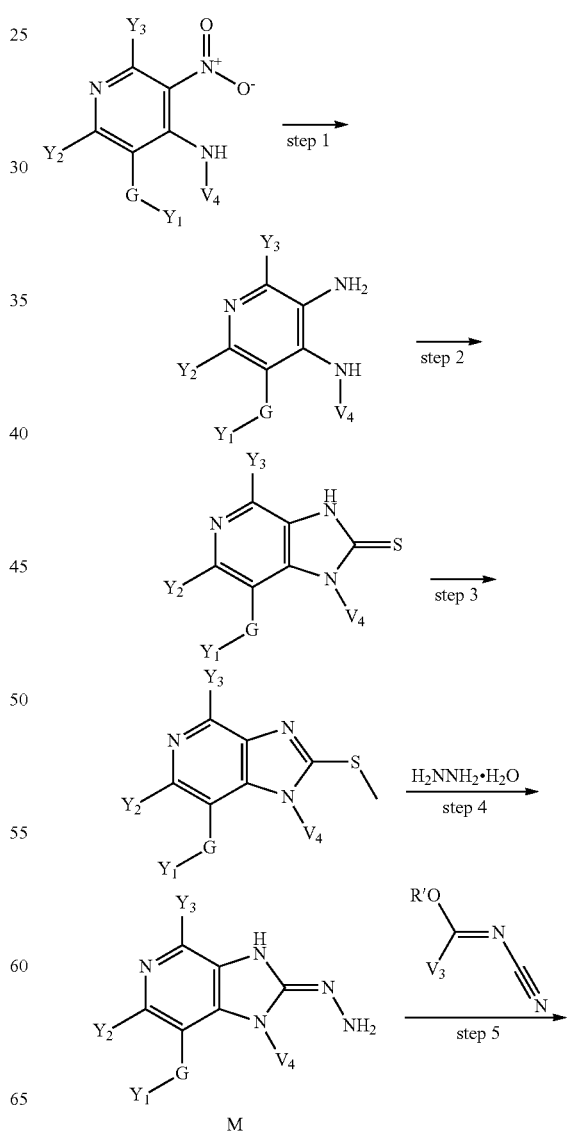

M

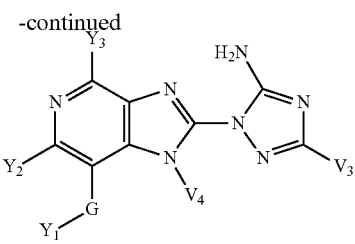

In scheme 2, G, $Y_1$, $Y_2$, $Y_3$, $V_3$, $V_4$ have the meanings as defined for compounds of formula I.

Step 1

The nitro-pyridine derivative can be transformed into the corresponding amino-pyridine by a number of methods. Metal reductions using metals or metal derivatives such as iron, tin, tin dichloride, zinc, indium are well documented in the literature.

Relevant references include: WO 2010078408; WO 2009155527; U.S. Pat. No. 7,737,279; Bioorganic & Medicinal Chemistry Letters (2010), 20(15), 4350-4354; WO 2009000663;

disodium dithionite: WO 2010030785

Step 2

The cyclization reaction towards the thione intermediate is a standard reaction and can be found well documented in the literature. The methods comprise the use of thiourea, carbon disulfide, thiocarbonyldiimidazole, thiophosgene, potassium xanthogenate as the thionylating agent. The transformation is usually carried out in an inert solvent such as DMF, NMP, DMSO, THF, dioxane, pyridine, dimethylacetamide, MeCN, toluene, $CH_2Cl_2$, and also alcohols such as ethanol or butanol for certain transformations. Relevant literature references include: Journal of Medicinal Chemistry, 48(10), 3481-3491; 2005; WO 2008115262; WO 2007106852; WO 2007056112, Khimiya Geterotsiklicheskikh Soedinenii (1988), (6), 799-804; Journal of Heterocyclic Chemistry, 26(2), Journal of the Chemical Society, 2379-82; 1962; 409-12; 1989; Bioorganic & Medicinal Chemistry, 18(21), 7357-7364; 2010; Indian Journal of Chemistry, Section B: Organic Chemistry Including Medicinal Chemistry, 21B(5), 485-7; 1982

Step 3

The transformation of the thione to the methyl-thio derivative has been described in the literature. Methyl iodide or dimethyl sulphate may be used along with a base such as dipotassium, disodium or dicaesium carbonate, potassium or sodium hydroxide, a sodium or potassium alcoholate, such as sodium or potassium methylate or ethylate. Relevant literature references include: Journal of Medicinal Chemistry (2005), 48(10), 3481-3491; WO 2010036613; Organic Communications (2009), 2(2), 49-59; Heterocyclic Communications (2008), 14(6), 469-472; Steroids (2004), 69(3), 201-217; Acta Chemica Scandinavica (1994), 48(10), 823-30; Khimiko-Farmatsevticheskii Zhurnal (1989), 23(8), 952-6

Step 4

The transformation consists of substituting the methylthio group by hydrazine. As the nucleophile, either hydrazine hydrate or a properly protected hydrazine derivative may be used. Such protected hydrazine derivatives include compounds such as $(CH_3)_3C-O-CO-NH-NH_2$, $PhCH_2-O-CO-NH-NH_2$, $H_2C=CHCH_2-O-CO-NH-NH_2$, $CH_3-CO-NH-NH_2$. In order to obtain the free hydrazone compound M, the protecting group is cleaved according to one of the deprotection scenarios of the well-known protecting groups. Relevant literature references include the following: Acta Poloniae Pharmaceutica, 40(1), 7-14; 1983; Canadian Journal of Chemistry, 61(11), 2563-6; 1983

Step 5

In this step, the aminotriazole ring is built up. The hydrazine derivative is typically reacted with reactants of the form $NC-N=C(OR^1)-V_3$ wherein $R^1$ is typically an alkyl group such as methyl, ethyl, propyl, butyl or $R^1$ is an optionally substituted phenyl moiety such as phenyl, 4-chloro-phenyl, or alternatively with a reactant of the form or $(V_3'-S-C=N-CN$ wherein $V_3'$ is a suitable subgroup of $V_3$ such as H, $C_1$-$C_8$ alkyl, $C_3$-$C_8$ cycloalkyl, $C_3$-$C_8$ cycloalkenyl, $C_2$-$C_8$ alkenyl, $C_2$-$C_8$ alkynyl, benzyl, each of which can—apart form H—optionally be substituted. The preparation of the reagents is well described in the literature. Solvents usually used include water, methanol ethanol, butanol, tert-butanol, DMF, NMP, dimethylacetamide, THF, dioxane, DMSO, sulfolane, pyridine, MeCN, toluene, cyclohexane, hexanes, $CH_2Cl_2$, $CHCl_3$, $ClCH_2CH_2Cl$. The reaction can be carried out in the presence of bases such as triethylamine, Hünig's base, sodium tert-butylate, sodium or potassium carbonate or bicarbonate. Relevant literature references include the following: Journal of Heterocyclic Chemistry, 19(5), 1157-64; 1982; Organic Letters, 11(23), 5482-5485; 2009; Tetrahedron Letters, 39(43), 7983-7986; 1998; Journal of Heterocyclic Chemistry, 29(5), 1209-11; 1992; PCT Int. Appl., 2005013982, 17 Feb. 2005; PCT Int. Appl., 2008083353, 10 Jul. 2008; WO 2005/077939; WO 2008/083356

Scheme 3

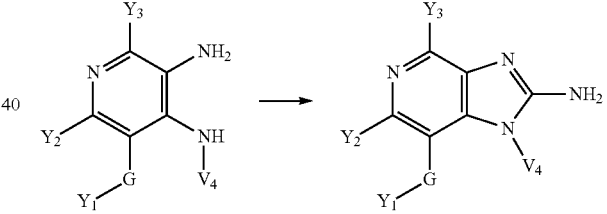

In scheme 3, G, $Y_1$, $Y_2$, $Y_3$, $V_4$ have the meanings as defined for compounds of formula I.

The transformation is done using reagents such as cyanogen bromide, cyanamide, 1,1'-carbonimidoylbis-1H-imidazole and iminourea.

Typically, solvents such as $CH_2Cl_2$, $ClCH_2CH_2Cl$, $CHCl_3$, ethanol, butanol, water, THF, dioxane, DMF, NMP, dimethylacetamide, MeCN, DMSO, cyclohexane, hexanes, ethyl acetate are used. Relevant literature references include: Bioorganic & Medicinal Chemistry Letters, 16(11), 2842-2845; 2006; PCT Int. Appl., 2010078408, 8 Jul. 2010; PCT Int. Appl., 2007106852, 20 Sep. 2007; PCT Int. Appl., 2005080380, 1 Sep. 2005; Journal of Organic Chemistry, 67(5), 1708-1711; 2002; Tetrahedron, 32(7), 839-42; 1976; Bioorganic & Medicinal Chemistry Letters, 18(23), 6218-6221; 2008; Journal of Organic Chemistry, 67(21), 7553-7556; 2002

In the preparation of compounds of formula (I), the following alternative scheme may be chosen.

Scheme 4

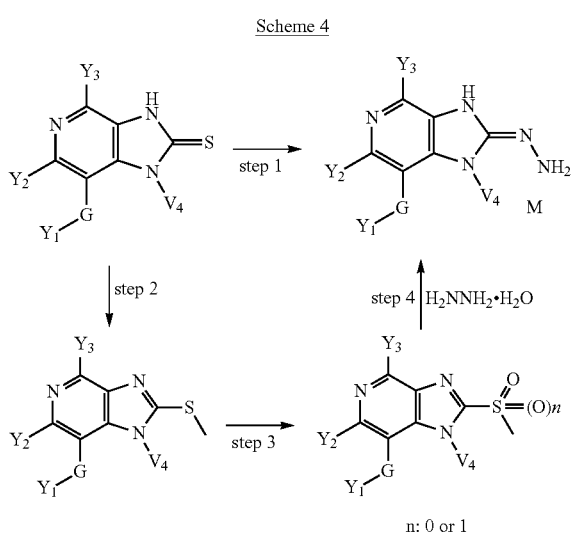

n: 0 or 1

In scheme 4, G, $Y_1$, $Y_2$, $Y_3$, $V_4$ have the meanings as defined for compounds of formula I.

Step 1

The thione intermediate may be directly transformed into compound M whereby the thione starting material is reacted with hydrazine hydrate to give compound M.

Analogous transformations are to be found in the literature and include the following: Australian Journal of Chemistry, 35(6), 1263-7; 1982; Heterocyclic Communications, 14(6), 469-472; 2008; Indian Journal of Chemistry, Section B: Organic Chemistry Including Medicinal Chemistry, 27B (3), 298-300; 1988; WO 2005/077939.

Step 2 is already described in scheme 2, step 3 above.

Step 3

Deviating from the sequence in the previous scheme 2, the methyl-thio intermediate is oxidized either to the methyl sulfoxide or to the methyl sulfone. A large variety of oxidants can be used. Such oxidants include hydrogen peroxide or hydrogen peroxide-urea adduct in the presence of an acid such as acetic acid or trifluoroacetic acid. Oxidants include also the use of peracids such as meta-chloroperbenzoic acid, peracetic acid or trifluoroperacetic acid. Such peracids can be used as such, or, alternatively, they can be generated in situ from the corresponding acids and hydrogen peroxide or the corresponding acid anhydride and hydrogen peroxide. Still other oxidants include permanganates, such as sodium or potassium permanganate, or $MeReO_3$ and hydrogen peroxide. Depending upon the reaction time and the stoichiometry, the reaction can be tuned either towards the formation of the sulfoxide or the sulfone. Furthermore, if a mixture of both the sulfoxide and the sulfone is obtained they can usually be separated by chromatography.

Analogous transformations can be found in the literature: Journal of Heterocyclic Chemistry, 32(1), 227-34; 1995; Bioorganic & Medicinal Chemistry Letters, 19(3), 903-907; 2009; Synthetic Communications, 40(6), 808-813; 2010; Journal of Medicinal Chemistry, 48(10), 3481-3491; 2005, Journal of Organic Chemistry, 57(5), 1390-405; 1992; Canadian Journal of Chemistry, 61(11), 2563-6; 1983; Acta Poloniae Pharmaceutica, 40(1), 7-14; 1983; Journal of Organic Chemistry, 72(26), 9924-9935; 2007; Advanced Synthesis & Catalysis, 351(6), 903-919; 2009

Step 4

Step 4 demonstrates the nucleophilic substitution whereby hydrazine replaces the methylsulfone or methylsulfoxide group. Hydrazine hydrate is the preferred nucleophile. Relevant literature references include: Heterocycles, 6(12), 1999-2004; 1977; Chemical Research in Toxicology, 16(11), 1433-1439; 2003; Synthesis, (6), 894-898; 2003

Scheme 5

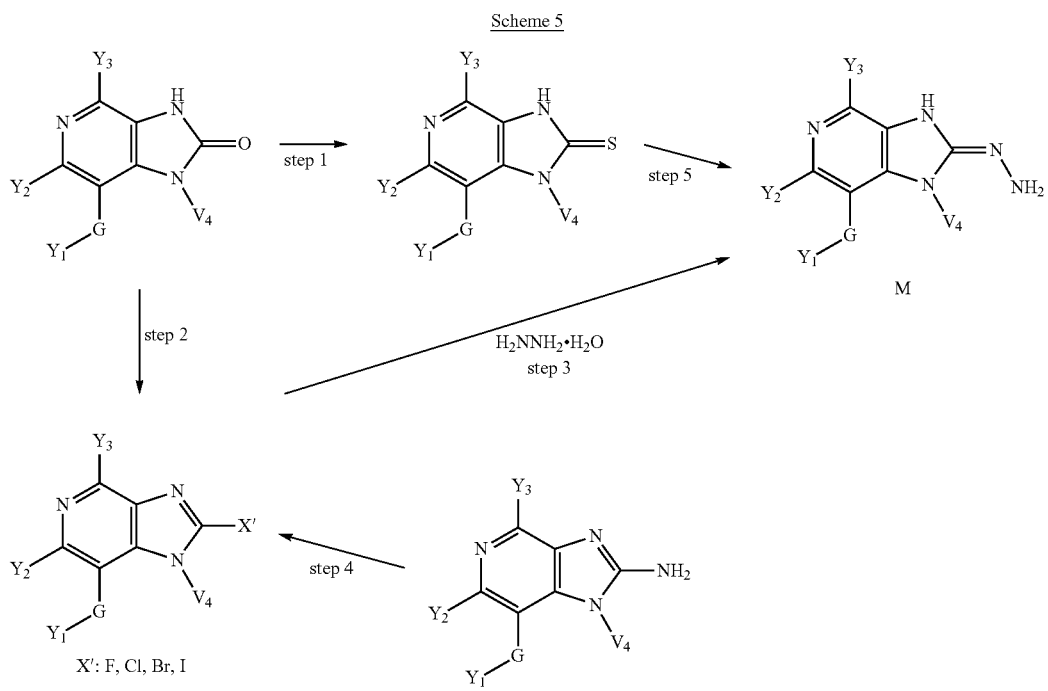

X': F, Cl, Br, I

In scheme 5, G, $Y_1$, $Y_2$, $Y_3$, $V_4$ have the meanings as defined for compounds of formula I.

Step 1

Step 1 is the transformation of a urea functional group into the corresponding thiourea. Reagents to carry out this transformation include $P_2S_5$, Lawesson's reagent and thiourea. Solvents used include THF, dioxane, ethanol, toluene, DMF, xylene, MeCN and $CH_2Cl_2$. The transformation can be done in the presence of a base, such as pyridine. Relevant literature includes: Journal of Heterocyclic Chemistry, 18(4), 751-3; 1981, Journal of the American Chemical Society, 80, 6671-9; 1958; Tetrahedron Letters, 29(2), 195-8; 1988; Journal of the Chemical Society, 860-4; 1962; PCT Int. Appl., 2010068483, 17 Jun. 2010

Step 2

The 2H-imidazo[4,5-c]pyridin-2-one starting material is transformed into the corresponding halogen compound. To obtain the chloride, reagents such as $POCl_3$, $(Cl_3CO)_2C=O$ with a base such as pyridine are used. In order to obtain the bromide, reagents such as $POBr_3$ and $PBr_3$ are used. These transformations can be done neat or in the presence of (an) inert solvent(s) such as $CH_2Cl_2$, $ClCH_2CH_2Cl$, $CHCl_3$, $CCl_4$, AcOEt, THF, dioxane, toluene, chloro-benzene, cyclohexane or sulfolane. The transformations can be done in the presence of a base such as pyridine, N,N-dimethylaniline or N,N-diethylaniline. The iodo derivative is usually prepared from the chloro or bromo analogues.

Supporting Literature References:

Cl: Journal of Medicinal Chemistry, 29(6), 1099-113; 1986; Helvetica Chimica Acta, 61(8), 2958-73; 1978; PCT Int. Appl., 2009134750, 5 Nov. 2009; Bioorganic & Medicinal Chemistry Letters, 18(18), 5010-5014; 2008; Chemical & Pharmaceutical Bulletin, 37(10), 2723-6; 1989;

Br: PCT Int. Appl., 2008082003; PCT Int. Appl., 2007069053; Synlett, (16), 2625-2628; 2006; Journal of Organic Chemistry, 69(25), 8829-8835; 2004;

I: Tetrahedron, 57(9), 1677-1687; 2001

Step 3

To obtain compound M, the halide is reacted with hydrazine hydrate either in pure form or in the presence of an inert solvent such as THF, dioxane, diethyl ether, toluene, DMF, NMP, DMSO, ethanol or butanol. The reaction is run either at room temperature or under heating.

Relevant literature references include: PCT Int. Appl., 2008024981, 28 Feb. 2008; Journal of Medicinal Chemistry, 44(25), 4359-4369; 2001; Journal of Medicinal Chemistry, 44(25), 4359-4369; 2001; Australian Journal of Chemistry, 35(6), 1263-7; 1982; Chemische Berichte, 88, 1932-7; 1955; Journal of Heterocyclic Chemistry, 35(4), 949-954; 1998; Bulletin de la Societe Chimique de France, 1793-8, 1959

Step 4

The amine compound is first transformed into the corresponding diazonium salt by the treatment with a nitrite such as sodium or potassium nitrite in the presence of an acid such as hydrochloric or hydrobromic acid, phosphoric or sulphuric acid. Alternatively the transformation can also be carried out under non-aqueous conditions whereby an alkyl nitrite such as iso-pentyl or tert-butyl nitrite in an inert solvent such as $CH_2Cl_2$, $CHCl_3$, $ClCH_2CH_2Cl$ or tert-butyl-$NO_2$ is used. The intermediate diazonium salt is then transformed into the halide by reagents such as KI, with or without a catalytic amount of $I_2$, or CuBr, CuCl, $CuBr_2$ or $CuCl_2$. Relevant literature references: Helvetica Chimica Acta, 83(12), 3229-3245; 2000; Journal of Medicinal Chemistry, 38(20), 4098-105; 1995; PCT Int. Appl., 2009011880, 22 Jan. 2009; Journal of Medicinal Chemistry, 38(20), 4098-105; 1995

Step 5

This step is the same as step 1 in scheme 4 above.

Scheme 6

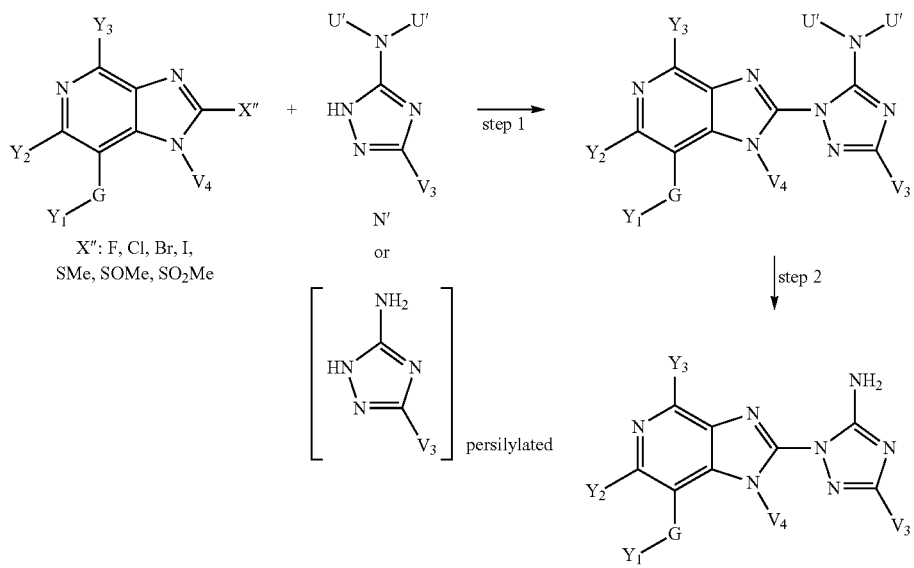

In scheme 6, G, $Y_1$, $Y_2$, $Y_3$, $V_3$, $V_4$ have the meanings as defined for compounds of formula I.

Each U' is independently of the other H, (tert-butyl)-O—CO, allyl-O—CO, benzyl-O—CO, HC(=O), $C_1$-$C_6$-alkyl-O—CO or $C_1$ $C_6$-alkyl-CO, or both U' together with the nitrogen atom to which they are attached form one of the following cycles:

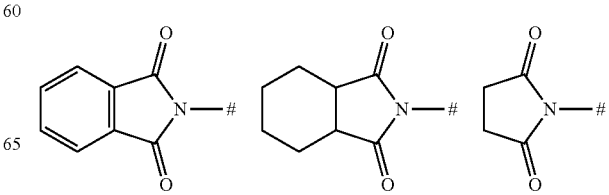

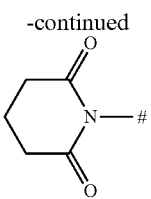

Typical such compounds N' are either available commercially or are described in the literature. Alternatively, intermediates N' may be a silylated or persilylated form of the aminotriazole, wherein U' is tri-($C_1$-$C_6$-alkyl)-silyl, preferentially trimethylsilyl. Partially or fully silylated form of intermediates N' are obtained by treating a given compound of formula N' wherein U' is H with a silylating agent. This may be performed either with or without a solvent being present, and optionally in the presence of a catalyst such as $Et_3N$, $(NH_4)_2SO_4$ or $CF_3SO_2OSiMe_3$.

The preferred trimethylsilylation may consist of treating N' wherein U' is H, with a trimethylsilylating agent such as $Me_3SiCl$, $Me_3SiBr$, $(Me_3Si)_2NH$ or $MeC(=NSiMe_3)$—O—$SiMe_3$. This may be performed either with or without an inert solvent, such as DMF, NMP, dimethylacetamide, MeCN, toluene being present, and optionally in the presence of a catalyst such as $Et_3N$, $(NH_4)_2SO_4$ or $CF_3SO_2OSiMe_3$. Relevant references for analoguous transformations include Organic Reactions 55, 1; 2000; Synthesis, (8), 773-8; 1992; Synthetic Communications, 34(5), 917-932; 2004

Step 1

This transformation consists of condensing an optionally protected amino triazole derivative with an electrophilic 3H-imidazo[4,5-c]pyridine derivative having a leaving group X" in the 2-position. Leaving group X" is selected from F, Cl, Br, I, SMe, SOMe and $SO_2Me$. In the course of the condensation reaction, the leaving group is displaced by the nitrogen atom of the triazole derivative to give the [1H-1,2,4-triazol-5-yl]amino substituent, optionally protected at the amino group. Relevant literature references for analogous transformations: Eur. Pat. Appl., 330959, 6 Sep. 1989, Russian Journal of Organic Chemistry (Translation of Zhurnal Organicheskoi Khimii), 34(7), 1032-1039; 1998; Russian Journal of Organic Chemistry (Translation of Zhurnal Organicheskoi Khimii), 37(8), 1158-1168; 2001

Step 2

In this step the amine is generated from the bis-amino-protected precursor. Such deprotection steps are standard procedures and well documented in the literature. When the protecting group is BOC, the deprotection is described in scheme 8, step 3. In some cases e.g. when U' is $C_1$-$C_6$-alkyl-CO, the deprotection consists of a hydrolysis preferentially under acidic conditions.

Scheme 7

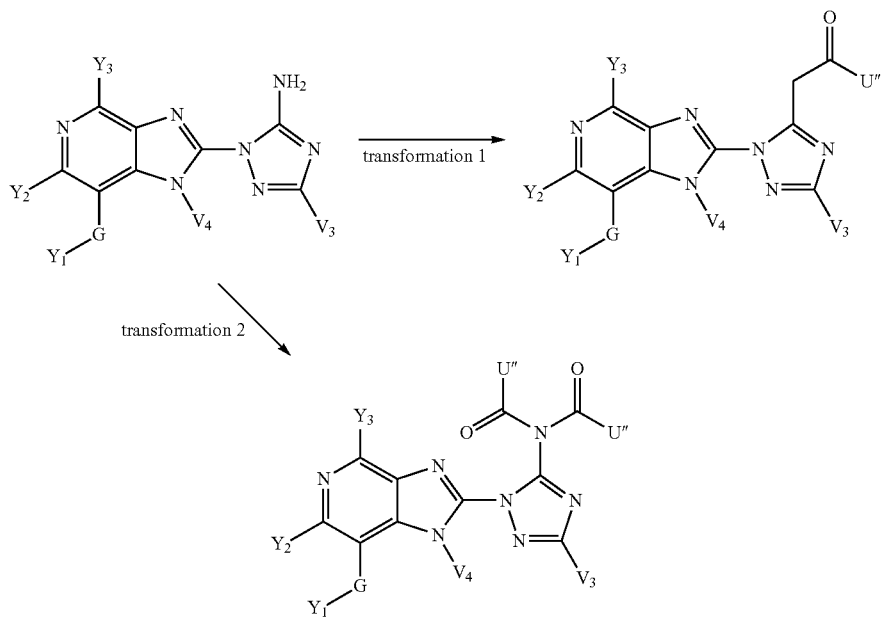

wherein the meanings of the G, $Y_1$, $Y_2$, $Y_3$, $V_3$, $V_4$ are as defined for compounds of formula I and wherein U" has the meaning $R^2$, $C_1$-$C_8$-alkoxy, $C_3$-$C_8$-alkenyloxy or benzyloxy, wherein $R^2$ is as defined above.

Transformation 1

The acylation at the amino function is usually carried out using an acyl chloride (Cl—CO—U") or carboxylic acid anhydride (U"—CO—O—CO—U" or e.g. U"—CO—O—CO—C(CH$_3$)$_3$). Typical solvents used include $CH_2Cl_2$, $CHCl_3$, $ClCH_2CH_2Cl$, diethyl ether, THF, dioxane, toluene, cyclohexane, pyridine, ethyl acetate, MeCN. The reaction is typically done in the presence of a base such as Hünig's base or triethylamine. The acylation can be done with or without an acylation catalyst such as pyridine, 4-dimethylamino-pyridine or 4-pyrrolidino-pyridine. Most often, such acylation catalysts are used together with a base such as triethylamine or Hünig's base. In certain cases the reaction is carried out in water in the presence of an inorganic base such as sodium or potassium hydroxide or carbonate. Relevant literature references include the following: Russ. 2290398, 27 Dec. 2006; Chemistry of Heterocyclic Compounds, 41(9), 1139-1146, 2005; Journal of Agricultural and Food Chemistry, 50(6), 1383-1388; 2002; Journal of Heterocyclic Chemistry, 24(1), 127-42; 1987; Heterocyclic Communications, 13(1), 73-76; 2007

Transformation 2

As for transformation 1 but with the stoichiometry adjusted such that a bis-acylation at the nitrogen atom takes place. Relevant literature references include: Zeitschrift fuer Chemie, 17(6), 220-1; 1977; Monatshefte fuer Chemie, 135(2), 173-184; 2004; Journal of Medicinal Chemistry, 53(3), 1117-1127; 2010; Journal of Medicinal Chemistry, 53(10), 4266-4276; 2010; Journal of Medicinal Chemistry, 43(1), 27-40; 2000; Zeitschrift fuer Chemie, 17(6), 220-1; 1977.

Scheme 8

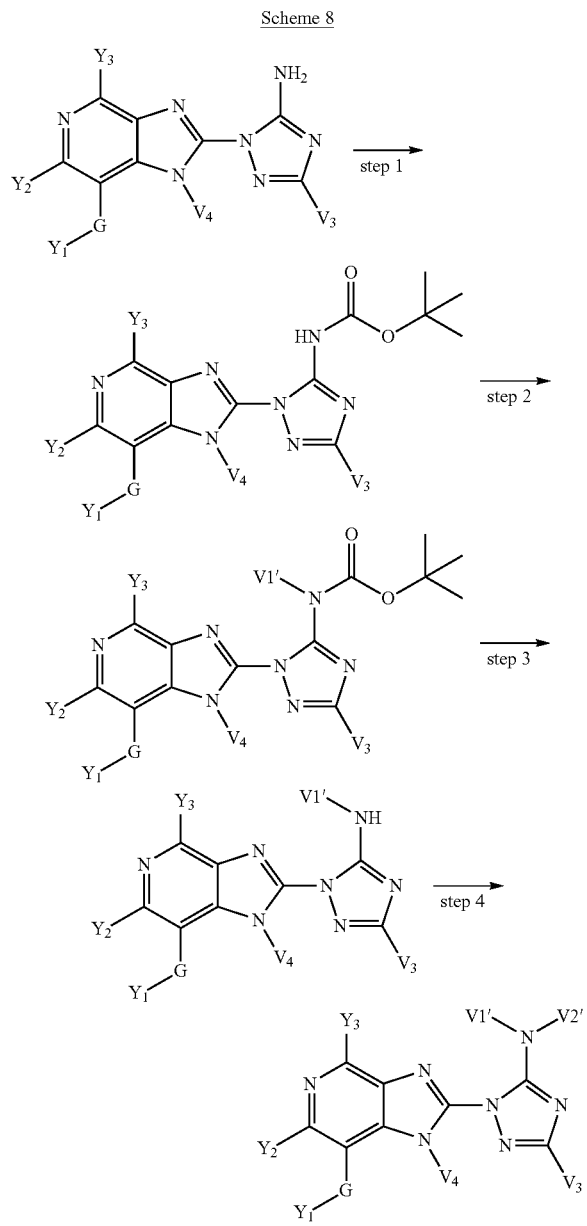

where the meanings of $G$, $Y_1$, $Y_2$, $Y_3$, $V_3$, $V_4$ are as defined for compounds of formula I.

$V_1'$ and $V_2'$, independently of each other, have the following meanings:

$C_1$-$C_8$ alkyl, $C_3$-$C_8$ alkenyl, $C_3$-$C_8$ cycloalkyl, $C_3$-$C_8$ cycloalkenyl, $C_3$-$C_8$ alkynyl or benzyl, wherein the alkyl, alkenyl, alkynyl, cycloalkyl, cycloalkenyl and benzyl are optionally substituted by one or more halogen, CN, OH, $C_1$-$C_4$ alkyl, $C_1$-$C_4$ haloalkyl, $C_1$-$C_4$ alkoxy or $C_1$-$C_4$ haloalkoxy.

Step 1 was already dealt with in scheme 7, transformation 2.

Step 2

This is an alkylation of a BOC-protected secondary amine. The process is not limited to the use of a BOC-protected amine, though; an acetyl protected amine could be used instead, for example. The BOC protecting group is chosen to illustrate the principle.

The BOC-protected amine is treated with a base such as sodium hydride, LDA, sodium or potassium alcoholate (e. g. tert-butylate), sodium or potassium carbonate, and with an alkylating agent. Such alkylating agents include Cl—$V_1'$, Br—$V_1'$, I—$V_1'$, MeSO$_2$O—$V_1'$, p-Me-C$_6$H$_4$—SO$_2$O—$V_1'$, CF$_3$SO$_2$O—$V_1'$. Preferred solvents to carry out this transformation include diethyl ether, THF, dioxane, toluene, DMF, NMP, much depending on the chosen reaction conditions. Literature references relevant to this transformation include: Bioorganic & Medicinal Chemistry Letters, 17(16), 4495-4499; 2007; PCT Int. Appl., 2006107923, 12 Oct. 2006; Journal of Medicinal Chemistry, 32(2), 409-17; 1989; PCT Int. Appl., 2006107923, 12 Oct. 2006; Bioorganic & Medicinal Chemistry Letters, 16(11), 2842-2845; 2006

Step 3

This step consists of removing the BOC-protecting group. This is suitably carried out under acidic conditions. These include mixtures of CH$_2$Cl$_2$ and trifluoro acetic acid (e.g. using the two components in a 1:1 ratio (v:v)), trifluoro acetic acid alone, acetic acid (preferably at elevated temperature), HCl in a number of solvents (e.g. water, diethyl ether, MeOH) or HBr in acetic acid. Relevant literature references include the following: Angewandte Chemie, International Edition, 47(19), 3581-3583; 2008; Bioorganic & Medicinal Chemistry, 18(2), 663-674; 2010; Journal of the American Chemical Society, 131(29), 9868-9869; 2009; U.S. Pat. Appl. Publ., 20090186879, 23 Jul. 2009

Step 4

This step consists of alkylation, alkenylation, alkynylaton or benzylation of a secondary amine to obtain a tertiary amine. Typically the secondary amine is treated with a strong base such as sodium hydride or LDA, followed by the addition of an alkylating agent, for example. Such alkylating agents include Cl—$V_2'$, Br—$V_2'$, I—$V_2'$, MeSO$_2$O—$V_2'$, p-Me-C6H4-SO$_2$O—$V_2'$ and CF$_3$SO$_2$O—$V_2'$. For the case where $V_2'$ is methyl or ethyl, preferred reagents are MeO—SO$_2$—OMe and EtO—SO$_2$—OEt. Relevant literature references include the following: PCT Int. Appl., 2006031878, 23 Mar. 2006; Bioorganic & Medicinal Chemistry, 12(1), 139-149; 2004; PCT Int. Appl., 2010138487, 2 Dec. 2010; European Journal of Organic Chemistry, (9), 2419-2428; 1999.

Scheme 9

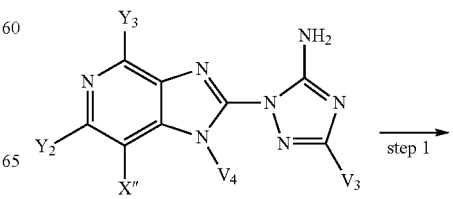

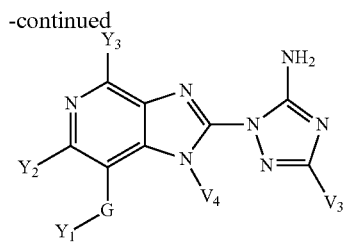

where the meanings of G, $Y_1$, $Y_2$, $Y_3$, $V_3$ and $V_4$ are as defined for compounds of formula I.

X" is a halogen, preferably Cl, Br or I. More preferably X" is Br

Step 1

The step consist of a Suzuki, Stille, Sonogashira or other similar cross coupling reactions. Typically, the halogenated starting material, preferably chloro, bromo or iodo, is reacted with an acetylene or an organometallic reagent of formula M[G-Y1], wherein M is $InCl_2$, InCl(G-Y1), In(G-Y1)$_2$, MgCl, MgBr, Sn($R_7$)$_3$, ZnCl, ZnBr or B(O$R_7$)$_2$, wherein either $R_7$ is independently from each other hydrogen, $C_1$-$C_6$alkyl or wherein two $R_7$ together can form a $C_3$-$C_8$cycloalkyl, and a catalyst, such as tetrakistriphenylphosphinepalladium, palladium dichloride, [1,1-bis(diphenylphosphino) ferrocene]dichloropalladium(II), palladium acetate or bis(diphenylphosphine)palladium(II) chloride.

It has now been found that the compounds of formula (I) according to the invention have, for practical purposes, a very advantageous spectrum of activities for protecting useful plants against diseases that are caused by phytopathogenic microorganisms, such as fungi, bacteria or viruses.

The invention therefore also relates to a method of controlling or preventing infestation of useful plants by phytopathogenic microorganisms, especially fungi, wherein a compound of formula (I) is applied as active ingredient to the plants, to parts thereof or the locus thereof. The compounds of formula (I) according to the invention are distinguished by excellent activity at low rates of application, by being well tolerated by plants and by being environmentally safe. They have very useful curative, preventive and systemic properties and are used for protecting numerous useful plants. The compounds of formula (I) can be used to inhibit or destroy the diseases that occur on plants or parts of plants (fruit, blossoms, leaves, stems, tubers, roots) of different crops of useful plants, while at the same time protecting also those parts of the plants that grow later e.g. from phytopathogenic microorganisms.

It is also possible to use compounds of formula (I) as dressing agents for the treatment of plant propagation material, in particular of seeds (fruit, tubers, grains) and plant cuttings (e.g. rice), for the protection against fungal infections as well as against phytopathogenic fungi occurring in the soil.

Furthermore the compounds of formula (I) according to the invention may be used for controlling fungi in related areas, for example in the protection of technical materials, including wood and wood related technical products, in food storage or in hygiene management.

The compounds of formula (I) are particularly effective to protect useful plants or plant propagation material thereof against phytopathogenic fungi belonging to the following classes: Ascomycetes (e.g. the genus *Cochliobolus, Colletotrichum, Fusarium, Gaeumannomyces, Giberella, Monographella, Microdochium, Penicillium, Phoma, Pyricularia, Magnaporthe, Septoria, Pseudocercosporella, Tapesia* and *Thielaviopsis*); Basidiomycetes (e.g. the genus *Phakopsora, Puccinia, Rhizoctonia, Thanatephorus, Sphacelotheca, Tilletia, Typhula* and *Ustilago*); Fungi imperfecti (also known as Deuteromycetes; e.g. the genus *Ascochyta, Diplodia, Erysiphe, Fusarium, Helminthosporium, Phomopsis, Pyrenophora* and *Verticillium*); Oomycetes (e.g. *Aphanomyces, Peronospora, Peronosclerospora, Phytophthora, Plasmopara, Pseudoperonospora, Pythium*); and Zygomycets (e.g. the genus *Rhizopus*).

Within the scope of the invention, useful plants to be protected typically comprise the following species of plants: cereal (wheat, barley, rye, oat, rice, maize, sorghum and related species); beet (sugar beet and fodder beet); pomes, drupes and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucumber plants (pumpkins, cucum-bers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocado, *cinnamomum*, camphor) or plants such as tobacco, nuts, coffee, eggplants, sugar cane, tea, pepper, vines, hops, bananas and natural rubber plants, as well as ornamentals.

The term "useful plants" is to be understood as including also useful plants that have been rendered tolerant to herbicides like bromoxynil or classes of herbicides (such as, for example, HPPD inhibitors, ALS inhibitors, for example primisulfuron, prosulfuron and trifloxysulfuron, EPSPS (5-enol-pyrovyl-shikimate-3-phosphate-synthase) inhibitors, GS (glutamine synthetase) inhibitors or PPO (protoporphyrinogen-oxidase) inhibitors) as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady®, Herculex I® and LibertyLink®.

The term "useful plants" is to be understood as including also useful plants which have been so transformed by the use of recombinant DNA techniques that they are capable of synthesising one or more selectively acting toxins, such as are known, for example, from toxin-producing bacteria, especially those of the genus *Bacillus*.

Examples of such plants are: YieldGard® (maize variety that expresses a CryIA(b) toxin); YieldGard Rootworm® (maize variety that expresses a CryIIIB(b1) toxin); YieldGard Plus® (maize variety that expresses a CryIA(b) and a CryIIIB(b1) toxin); Starlink® (maize variety that expresses a Cry9(c) toxin); Herculex I® (maize variety that expresses a CryIF(a2) toxin and the enzyme phosphinothricine N-acetyltransferase (PAT) to achieve tolerance to the herbicide glufosinate ammonium); NuCOTN 33B® (cotton variety that expresses a CryIA(c) toxin); Bollgard I® (cotton variety that expresses a CryIA(c) toxin); Bollgard II® (cotton variety that expresses a CryIA(c) and a CryIIA(b) toxin); VIPCOT® (cotton variety that expresses a VIP toxin); NewLeaf® (potato variety that expresses a CryIIIA toxin); Nature-Gard® Agrisure® GT Advantage (GA21 glyphosate-tolerant trait), Agrisure® CB Advantage (Bt11 corn borer (CB) trait), Agrisure® RW (corn rootworm trait) and Protecta®.

The term "useful plants" is to be understood as including also useful plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818, and EP-A-0 353 191. The methods of producing such transgenic plants are generally known to the person skilled in the art and are described, for example, in the publications mentioned above.

The term "locus" of a useful plant as used herein is intended to embrace the place on which the useful plants are growing, where the plant propagation materials of the useful plants are sown or where the plant propagation materials of the useful plants will be placed into the soil. An example for such a locus is a field, on which crop plants are growing.

The term "plant propagation material" is understood to denote generative parts of the plant, such as seeds, which can be used for the multiplication of the latter, and vegetative material, such as cuttings or tubers, for example potatoes. There may be mentioned for example seeds (in the strict sense), roots, fruits, tubers, bulbs, rhizomes and parts of plants. Germinated plants and young plants which are to be transplanted after germination or after emergence from the soil, may also be mentioned. These young plants may be protected before transplantation by a total or partial treatment by immersion. Preferably "plant propagation material" is understood to denote seeds.

The compounds of formula (I) can be used in unmodified form or, preferably, together with carriers and adjuvants conventionally employed in the art of formulation.

Therefore the invention also relates to compositions for controlling and protecting against phytopathogenic microorganisms, comprising a compound of formula (I) and an inert carrier, and to a method of controlling or preventing infestation of useful plants by phytopathogenic microorganisms, wherein a composition, comprising a compound of formula (I) as active ingredient and an inert carrier, is applied to the plants, to parts thereof or the locus thereof.

To this end compounds of formula (I) and inert carriers are conveniently formulated in known manner to emulsifiable concentrates, coatable pastes, directly sprayable or dilutable solutions, dilute emulsions, wettable powders, soluble powders, dusts, granulates, and also encapsulations e.g. in polymeric substances. As with the type of the compositions, the methods of application, such as spraying, atomising, dusting, scattering, coating or pouring, are chosen in accordance with the intended objectives and the prevailing circumstances. The compositions may also contain further adjuvants such as stabilizers, antifoams, viscosity regulators, binders or tackifiers as well as fertilizers, micronutrient donors or other formulations for obtaining special effects.

Suitable carriers and adjuvants (auxiliaries) can be solid or liquid and are substances useful in formulation technology, e.g. natural or regenerated mineral substances, solvents, dispersants, wetting agents, tackifiers, thickeners, binders or fertilizers. Such carriers are for example described in WO 97/33890.

The compounds of formula (I) or compositions, comprising a compound of formula (I) as active ingredient and an inert carrier, can be applied to the locus of the plant or plant to be treated, simultaneously or in succession with further compounds. These further compounds can be e.g. fertilizers or micronutrient donors or other preparations which influence the growth of plants. They can also be selective herbicides as well as insecticides, fungicides, bactericides, nematicides, molluscicides or mixtures of several of these preparations, if desired together with further carriers, surfactants or application promoting adjuvants customarily employed in the art of formulation.

A preferred method of applying a compound of formula (I), or a composition, comprising a compound of formula (I) as active ingredient and an inert carrier, is foliar application. The frequency of application and the rate of application will depend on the risk of infestation by the corresponding pathogen. However, the compounds of formula (I) may also penetrate the plant through the roots via the soil (systemic action) by drenching the locus of the plant with a liquid formulation, or by applying the compounds in solid form to the soil, e.g. in granular form (soil application). In crops of water rice such granulates can be applied to the flooded rice field. The compounds of formula (I) may also be applied to seeds (coating) by impregnating the seeds or tubers either with a liquid formulation of the fungicide or coating them with a solid formulation.

A formulation, i.e. a composition comprising the compound of formula (I) and, if desired, a solid or liquid adjuvant, is prepared in a known manner, typically by intimately mixing and/or grinding the compound with extenders, for example solvents, solid carriers and, optionally, surface-active compounds (surfactants).

The agrochemical formulations will usually contain from 0.1 to 99% by weight, preferably from 0.1 to 95% by weight, of the compound of formula (I), 99.9 to 1% by weight, preferably 99.8 to 5% by weight, of a solid or liquid adjuvant, and from 0 to 25% by weight, preferably from 0.1 to 25% by weight, of a surfactant.

Whereas it is preferred to formulate commercial products as concentrates, the end user will normally use dilute formulations.

Advantageous rates of application are normally from 5 g to 2 kg of active ingredient (a.i.) per hectare (ha), preferably from 10 g to 1 kg a.i./ha, most preferably from 20 g to 600 g a.i./ha. When used as seed drenching agent, convenient rates of application are from 10 mg to 1 g of active substance per kg of seeds. The rate of application for the desired action can be determined by experiments. It depends for example on the type of action, the developmental stage of the useful plant, and on the application (location, timing, application method) and can, owing to these parameters, vary within wide limits.

The compounds of formula (I), or a pharmaceutical salt thereof, described above may also have an advantageous spectrum of activity for the treatment and/or prevention of microbial infection in an animal. "Animal" can be any animal, for example, insect, mammal, reptile, fish, amphibian, preferably mammal, most preferably human. "Treatment" means the use on an animal which has microbial infection in order to reduce or slow or stop the increase or spread of the infection, or to reduce the infection or to cure the infection. "Prevention" means the use on an animal which has no apparent signs of microbial infection in order to prevent any future infection, or to reduce or slow the increase or spread of any future infection.

According to the present invention there is provided the use of a compound of formula (I) in the manufacture of a medicament for use in the treatment and/or prevention of microbial infection in an animal. There is also provided the use of a compound of formula (I) as a pharmaceutical agent. There is also provided the use of a compound of formula (I)

as an antimicrobial agent in the treatment of an animal. According to the present invention there is also provided a pharmaceutical composition comprising as an active ingredient a compound of formula (I), or a pharmaceutically acceptable salt thereof, and a pharmaceutically acceptable diluent or carrier. This composition can be used for the treatment and/or prevention of antimicrobial infection in an animal. This pharmaceutical composition can be in a form suitable for oral administration, such as tablet, lozenges, hard capsules, aqueous suspensions, oily suspensions, emulsions dispersible powders, dispersible granules, syrups and elixirs. Alternatively this pharmaceutical composition can be in a form suitable for topical application, such as a spray, a cream or lotion. Alternatively this pharmaceutical composition can be in a form suitable for parenteral administration, for example injection. Alternatively this pharmaceutical composition can be in inhalable form, such as an aerosol spray.

The compounds of formula (I) may be effective against various microbial species able to cause a microbial infection in an animal. Examples of such microbial species are those causing Aspergillosis such as *Aspergillus fumigatus, A. flavus, A. terrus, A. nidulans* and *A. niger*; those causing Blastomycosis such as *Blastomyces dermatitidis*; those causing Candidiasis such as *Candida albicans, C. glabrata, C. tropicalis, C. parapsilosis, C. krusei* and *C. lusitaniae*; those causing Coccidioidomycosis such as *Coccidioides immitis*; those causing Cryptococcosis such as *Cryptococcus neoformans*; those causing Histoplasmosis such as *Histoplasma capsulatum* and those causing Zygomycosis such as *Absidia corymbifera, Rhizomucor pusillus* and *Rhizopus arrhizus*. Further examples are *Fusarium* Spp such as *Fusarium oxysporum* and *Fusarium solani* and *Scedosporium* Spp such as *Scedosporium apiospermum* and *Scedosporium prolificans*. Still further examples are *Microsporum* Spp, *Trichophyton* Spp, *Epidermophyton* Spp, *Mucor* Spp, Sporothorix Spp, Phialophora Spp, *Cladosporium* Spp, *Petriellidium* spp, *Paracoccidioides* Spp and *Histoplasma* Spp.

The compositions of this invention may contain other compounds having biological activity, for example micronutrients or compounds having fungicidal activity or which possess plant growth regulating, herbicidal, insecticidal, nematicidal or acaricidal activity.

EXAMPLES

The following non-limiting Examples illustrate the above-described invention in greater detail without limiting it. Those skilled in the art will promptly recognise appropriate variations from the procedures both as to reactants and as to reaction conditions and techniques. All references mentioned herein are incorporated by reference in their entirety.

Example P1

Preparation of 2-(1-cyclohexylimidazo[4,5-c]pyridin-2-yl)-5-phenyl-1,2,4-triazol-3-amine a) Preparation of 5-phenyl-1H-1,2,4-triazol-3-amine; to a stirred solution of benzaldehyde (1.0 g, 9 mmol) and cyanamide (1.7 g, 40 mmol) in ethanol (20 mL) at 5-10° C. under inert atmosphere was added portionwise t-BuONa. The reaction mixture was then warmed to room temperature and stirred for 30 minutes. To this stirring mixture, recrystallized N-bromosuccinimide was added in portions. The reaction mixture was heated under reflux for 6 h and the reaction progress was monitored by TLC. Upon completion of reaction, the mixture was diluted with ice water (~50 mL) and extracted with ethyl acetate (3×20 mL). The organic layer was separated, washed with brine (50 mL), filtered and dried over $Na_2SO_4$. The solvent was removed in vacuo and the crude residue was chromatographed on silica gel (8% EtOAc in hexanes) to afford 5-phenyl-1H-1,2,4-triazol-3-amine (0.80 g, 49%) as a white solid.

$^1$H-NMR (400 MHz, $CDCl_3$): δ ppm=8.07-8.04 (m, 2H), 7.62-7.58 (m, 1H), 7.52-7.48 (m, 2H), 4.49-4.44 (q, 2H), 1.46-1.42 (t, 3H); LC-MS: $[M+H]^+$=174.90 b) To a stirred solution of 4-methoxy-3-nitro-pyridine (10.0 g, 65 mmol) in ethanol (100 mL) at room temperature was added cyclohexylamine (14.2 g, 143 mmol). The clear solution was then heated under reflux for 12 h and progress was monitored by TLC. Upon completion of the reaction, the volatiles were removed in vacuo to give crude material which was subjected to flash column chromatography (50% ethyl acetate in hexanes) to afford 4-cyclohexylamino-3-nitro-pyridine (14.1 g, 98% yield) as a pale yellow solid.

$^1$H-NMR (400 MHz, $CDCl_3$): δ ppm=9.19 (s, 1H), 8.24-8.22 (d, 1H), 8.18-8.17 (m, 1H), 6.70-6.69 (d, 1H), 3.52-3.48 (m, 1H), 2.04-2.02 (m, 2H), 1.82-1.79 (m, 2H), 1.68-1.65 (m, 1H), 1.45-1.39 (m, 5H); LC-MS $[M+H]^+$=222 c) To a solution of 4-cyclohexylamino-3-nitro-pyridine (14.0 g, 63 mmol) in ethanol (150 mL) under inert atmosphere was added 10% Pd/C (1.5 g). the reaction mixture was flushed with nitrogen followed by hydrogen gas for 2-3 times. The reaction mixture was then stirred under hydrogen atmosphere at room temperature for 12 h. Progress of the reaction was monitored by TLC. After completion of the reaction, the mixture was filtered through a celite bed and the filter cake washed with methanol (N200 mL). The filtrate was concentrated in vacuo to give the desired title 3-amino-4-cyclohexylamino-pyridine (11.2 g, 92%) as a brown solid.

$^1$H-NMR (400 MHz, DMSO): δ ppm=7.61 (s, 1H), 7.55-7.54 (d, 1H), 6.34-6.33 (d, 1H), 4.97-4.95 (d, 1H), 4.55 (s, 2H), 3.28-3.21 (m, 1H), 1.94-1.92 (m, 2H), 1.74-1.71 (m, 2H), 1.62-1.59 (m, 1H), 1.40-1.30 (m, 2H), 1.22-1.14 (m 3H); LC-MS $[M+H]^+$=192 d) To a stirred solution of 3-amino-4-cyclohexylamino-pyridine (3.0 g, 16 mmol) in THF (30 mL) at room temperature was added 1,1'-thiocarbonyldiimidazole (4.2 g; 26 mmol) and the resulting mixture was stirred for 30 minutes. Reaction progress was monitored by TLC. Upon completion of the reaction, the mixture was concentrated in vacuo to give crude material which was purified by flash column chromatography (3% methanol in dichloromethane) to afford 1-cyclohexyl-1,3-dihydro-2H-imidazo[4,5-c]pyridine-2-thione (3.2 g, 87%) as a brown solid.

$^1$HNMR (400 MHz, DMSO): δ ppm=13.15 (br, 1H), 8.42 (s, 1H), 8.27-8.26 (d, 1H), 7.72-7.71 (d, 1H), 5.04-4.98 (m, 1H), 2.12-2.10 (m, 2H), 1.88-1.86 (m, 2H), 1.72-1.69 (m, 3H), 1.45-1.36 (m, 3H); LC-MS: $[M+H]^+$=234 e) To a stirred suspension of 1-cyclohexyl-1,3-dihydro-2H-imidazo[4,5-c]pyridine-2-thione (3.0 g, 13 mmol) in a mixture of acetic acid (72 mL) and 48% aqueous HBr (1 mL, 18 mmol) at 0° C. was slowly added bromine (2.4 mL, 46 mmol). The thick orange mixture thus formed was stirred for 4.5 h. The mixture was then diluted with zed water (48 mL), and the product was neutralized by the addition of solid NaOH pellets until the pH reached 7. The resulting mixture was extracted with ethyl acetate (3×50 mL). The organic layer was separated, dried over $Na_2SO_4$, filtered and the solvent removed in vacuo to dryness. The resulting residue was purified by flash column chromatography (50% ethyl acetate in hexanes) to afford 2-bromo-1-(cyclohexyl)-1H-imidazo[4,5-c]pyridine (2.04 g, 56%) as a yellow solid.

$^1$H-NMR (400 MHz, $CDCl_3$): δ ppm=8.99 (s, 1H), 8.37-8.36 (d, 1H), 7.49-7.47 (d, 1H), 4.51-4.44 (m, 1H), 2.17-2.10 (m, 2H), 1.99-1.97 (m, 4H), 1.85-1.82 (m, 1H), 1.51-1.44 (m, 2H), 1.34-1.24 (m, 1H); LC-MS $[M+H]^+$=280 f) To a suspension of sodium hydride (32 mg, 1.3 mmol) in anhydrous DMF (2 mL) at 0° C. was added a solution of 5-phenyl-1H-1,2,4-triazol-3-amine (150 mg, 1.3 mmol). The reaction mixture was then warmed to at room temperature, stirred for 15 minutes and cooled back to 0° C. To this mixture was added dropwise a solution of 2-bromo-1-(cyclohexyl)-1H-imidazo[4,5-c]pyridine (340 mg, 1.2 mmol) in DMF (0.5 mL). The reaction mixture was allowed to warm to room temperature and heated at 100° C. for 6 h. The reaction was monitored by TLC. After completion, the reaction mixture was diluted with water and extracted with ethyl acetate (3×10 mL). The organic layer was separated, washed with brine, dried over $Na_2SO_4$ and, after filtration, was evaporated to dryness in vacuo. The crude material thus obtained was purified by preparative HPLC to afford 2-(1-cyclohexyl-1H-imidazo[4,5-c]pyridin-2-yl)-5-phenyl-2H-[1,2,4]-triazol-3-ylamine (100 mg, 31%) as a white solid.

$^1$H-NMR (400 MHz, DMSO): δ ppm=8.98 (s, 1H), 8.40-8.38 (d, 1H), 7.99-7.94 (m, 3H), 7.52-7.45 (m, 3H), 7.39 (br, 2H), 4.96-4.88 (m, 1H), 2.23-2.15 (m, 2H), 2.03-2.00 (m, 2H), 1.89 (m, 2H), 1.67 (m, 1H), 1.38 (m, 3H); melting point 222-225° C.;

LC-MS: $[M+H]^+$=360; HPLC (purity): 97.23%

Example P2

Preparation of 2-[1-ethyl-7-(p-tolyl)imidazo[4,5-c]pyridin-2-yl]-1,2,4-triazol-3-amine a) To a mixture of 5-bromo-N4-ethyl-pyridine-3,4-diamine (6.5 g, 30 mmol) and carbon disulfide (3 equiv., 90 mmol) in ethanol (10 mL/g), was added an aqueous solution of potassium hydroxide (3 equiv., 90 mmol) and the mixture was stirred overnight at 65° C. and allowed to return to room temperature. The reaction mixture was diluted with water, neutralized with acetic acid and the solids obtained were filtered off and washed with water and little ethanol to afford 7-bromo-1-ethyl-3H-imidazo[4,5-c]pyridine-2-thione (6.0 g, 77% yield) as a light brown solid.

$^1$-HNMR (400 MHz, DMSO): δ ppm=13.43 (br, 1H), 8.41 (s, 1H), 8.37 (s, 1H), 4.58-4.52 (q, 2H), 1.31-1.28 (t, 3H); melting point 250-255° C.

LC-MS: $[M+H]^+$=258, 260 b) To a stirred suspension of 7-bromo-1-ethyl-3H-imidazo[4,5-c]pyridine-2-thione (1.0 g, 3.9 mmol) in acetic acid (10 mL/g) and hydrogen bromide (48 mass %) in water (1.5 equiv., 5.8 mmol), bromine (4 equiv., 15.5 mmol) was added slowly at 0° C. The thick orange mixture thus formed was stirred for 12 h. The mixture was then concentrated, diluted with deionized water (10 mL), and the product was neutralized by the addition of solid NaOH pellets. The resulting mixture was further diluted with deionized water (15 mL) and extracted with ethyl acetate (3×50 mL). The organic layers were combined, dried over $Na_2SO_4$ and evaporated. The crude residue was purified by flash column chromatography (30 to 80% ethyl acetate gradient in hexanes) to afford 2,7-dibromo-1-ethyl-imidazo[4,5-c]pyridine (0.30 g, 30% yield) as a yellow solid.

$^1$H-NMR (400 MHz, DMSO): δ ppm=8.88 (s, 1H), 8.49 (s, 1H), 4.56-4.51 (q, 2H), 1.40-1.36 (t, 3H). LC-MS [M+1]=304, 306 c) To a stirred solution of 1H-1,2,4-triazol-5-amine (1.1 equiv., 1.1 mmol) in anhydrous DMF (2 ml) under inert atmosphere at 0° C. was slowly added cesium carbonate (1.5 equiv., 1.5 mmol). To this mixture was added a solution of 2,7-dibromo-1-ethyl-imidazo[4,5-c]pyridine (0.30 g, 1.0 mmol) in DMF. The reaction mixture was allowed to warm to room temperature and then heated to 35° C. The reaction was monitored by TLC and upon completion the mixture was cooled, diluted with water and extracted with ethyl acetate (3×15 mL). The organic layers were combined, washed with brine, dried over $Na_2SO_4$ and evaporated to dryness. The crude residue was then purified by flash chromatography (0 to 5% methanol gradient in dichloromethane) to afford 2-(7-bromo-1-ethyl-imidazo[4,5-c]pyridin-2-yl)-1,2,4-triazol-3-amine as an off white solid (0.125 g, 41% yield)

$^1$-HNMR (400 MHz, DMSO): δ ppm=8.94 (s, 1H), 8.54 (s, 1H), 7.81 (s, 1H), 7.43 (br, 2H), 4.72-4.67 (q, 2H), 1.46-1.43 (t, 3H); melting point 237-239° C.

d) To a solution of 2-(7-bromo-1-ethyl-imidazo[4,5-c]pyridin-2-yl)-1,2,4-triazol-3-amine (0.04 g, 0.1 mmol) in 1,2-dimethoxyethane (0.6 mL) in a round bottom flask covered with aluminium foil was added p-tolylboronic acid (1.5 equiv., 0.2 mmol) and aqueous sodium carbonate (2M, 3 equiv., 0.4 mmol). The reaction mixture was degassed for 20 minutes, then [1,1'-bis(diphenylphosphino)ferrocene]dichloropalladium (II) dichloromethane complex (0.05 equiv., 0.006 mmol) was added and the reaction mixture was heated 3 h at 80° C. The reaction mixture was then concentrated under educed pressure, diluted with water and extracted with ethyl acetate (2×10 mL). The organic layers were combined, washed with water (2×5 mL), brine (1×5 mL), dried over $Na_2SO_4$ and concentrated under reduced pressure. The crude residue was purified by flash column chromatography (0-10% MeOH gradient in dichloromethane) to afford 2-[1-ethyl-7-(p-tolyl)imidazo[4,5-c]pyridin-2-yl]-1,2,4-triazol-3-amine (0.026 g, 60% yield) as a white solid.

$^1$-HNMR (400 MHz, DMSO): δ ppm=8.98 (s, 1H), 8.10 (s, 1H), 7.76 (s, 1H), 7.46-7.44 (d, 2H), 7.40 (br, 2H), 7.36-7.34 (d, 2H), 4.11-4.09 (q, 2H), 2.41 (s, 3H), 1.46-1.43 (t, 3H); melting point 234-236° C.

Example P3

Preparation of 2-(2-(7-ethyl-1-propyl-imidazo[4,5-c]pyridin-2-yl)-1,2,4-triazol-3-amine a) 2-(7-bromo-1-propyl-imidazo[4,5-c]pyridin-2-yl)-1,2,4-triazol-3-amine was obtained following the procedure described in example 2 using 5-bromo-N4-propyl-pyridine-3,4-diamine as starting material (steps a, b and c). To a solution of 2-(7-bromo-1-propyl-imidazo[4,5- c]pyridin-2-yl)-1,2,4-triazol-3-amine (0.100 g, 0.310 mmol) in dry DMF (0.9 mL) was added tetraethylstannane (0.088 g, 0.074 mL, 0.37 mmol) followed by Pd(PPh3)4 (0.072 g, 0.062 mmol). The reaction mixture was heated at 170° C. under MW irradiation for 20 min. Water was added followed by AcOEt and 2 spoons of K2CO3, and the reaction mixture was stirred overnight at rt. The solution was then extracted with AcOEt, and the combined organic layers were washed with brine, dried over MgSO4, filtered, concentrated and purified by Isco combiflash Rf using DCM/MeOH to give 2-(7-ethyl-1-propyl-imidazo[4,5-c]pyridin-2-yl)-1,2,4-triazol-3-amine as a white solid.

1H NMR (400 MHz, CDCl3) δ ppm 0.87 (t, J=7.6 Hz, 3H), 1.34 (t, J=7.6 Hz, 3H), 1.71-1.82 (m, 2H), 2.96 (q, J=7.6 Hz, 2H), 4.65-4.75 (m, 2H), 6.53 (br. s, 2H), 7.58 (s, 1H), 8.21 (br. s, 1H), 8.79 (br. s, 1H)

Example P4

Preparation of 2-(5-amino-1,2,4-triazol-1-yl)-1-ethyl-imidazo[4,5-c]pyridine-7-carbonitrile a) To a solution of 2-(7-bromo-1-ethyl-imidazo[4,5-c]pyridin-2-yl)-1,2,4-triazol-3-amine (0.400 g, 1.30 mmol) in dry DMF (3.7 mL) was added tributyltin cyanide (0.492 g, 1.56 mmol) followed by Pd(PPh3)4 (C, 0.300 g, 0.260 mmol). The reaction mixture was heated at 150° C. under MW irradiation for 30 min. Water was added followed by AcOEt and solid K2CO3, and the reaction mixture was stirred overnight at rt. The solution was extracted with AcOEt. The combined organic layers were washed with brine, dried over MgSO4, filtered, concentrated and purified by Isco combiflash Rf using DCM/MeOH as eluent to give 2-(5-amino-1,2,4-triazol-1-yl)-1-ethyl-imidazo[4,5-c]pyridine-7-carbonitrile as a grey solid. 1H NMR (400 MHz, CDCl3) δ ppm 1.56 (t, J=7.0 Hz, 3H), 5.03 (q, J=7.0 Hz, 2H), 6.78 (br. s, 2H), 7.64 (s, 1H), 8.70 (s, 1H), 9.04 (s, 1H)

Example P5

Preparation of 1-[2-(7-acetyl-1-ethyl-imidazo[4,5-c]pyridin-2-yl)-1,2,4-triazol-3-yl]pyrrolidine-2,5-dione a) To a solution of 2-(7-bromo-1-ethyl-imidazo[4,5-c]pyridin-2-yl)-1,2,4-triazol-3-amine (3.2 g) and in DMF (48 mL) under nitrogen was added tributyl(1-ethoxyvinyl)stannane (1.1 equiv.) and PdCl$_2$(PPh$_3$)$_2$ (0.05 equiv.) and the reaction was heated at 100° C. for 5 h and then stirred at room temperature overnight. The reaction mixture was quenched with water and extracted with ethyl acetate. The combined organic layers were washed with water, sodium bicarbonate solution and brine, dried over sodium sulphate and concentrated. The product material was then purified by Combiflash using 0-5% MeOH in DCM to afford 2-[7-(1-ethoxyvinyl)-1-ethyl-imidazo[4,5-c]pyridin-2-yl]-1,2,4-triazol-3-amine as a white solid.
Melting point: 193-195° C.

b) To a solution of 2-[7-(1-ethoxyvinyl)-1-ethyl-imidazo[4,5-c]pyridin-2-yl]-1,2,4-triazol-3-amine (2.3 g) in methanol (23 mL) was added 23 mL of 2N hydrochloric acid, and the reaction mixture was stirred at room temperature overnight. The reaction mixture was then concentrated, neutralized with a sodium bicarbonate solution and extracted with ethyl acetate. The combined organic layers were washed with water and brine, dried over sodium sulphate and concentrated. The crude material was then purified by Combiflash using 0-5% MeOH in DCM to afford 1-[2-(5-amino-1,2,4-triazol-1-yl)-1-ethyl-imidazo[4,5-c]pyridin-7-yl]ethanone as a white solid.
Melting point: 242-244° C.

c) To a suspension of 1-[2-(5-amino-1,2,4-triazol-1-yl)-1-ethyl-imidazo[4,5-c]pyridin-7-yl]ethanone (0.080 g, 0.30 mmol) in xylene (1.5 mL) was added succinic anhydride (0.030 g, 0.30 mmol) followed by triethylamine (0.030 g, 0.041 mL, 0.30 mmol). The reaction mixture was stirred for 1 h30 at 125° C. The reaction was cooled to rt and the solvent was evaporated. The residue was purified by Isco combiflash Rf using DCM/MeOH as eluent to give 1-[2-(7-acetyl-1-ethyl-imidazo[4,5-c]pyridin-2-yl)-1,2,4-triazol-3-yl]pyrrolidine-2,5-dione as a white solid.

$^1$H NMR (400 MHz, CDCl$_3$) δ ppm 1.24 (t, J=7.0 Hz, 3H), 2.75 (s, 3H), 2.84 (s, 4H), 4.64 (q, J=7.0 Hz, 2H), 8.22 (s, 1H), 8.87 (s, 1H), 9.07 (s, 1H)

Example P6

Preparation of 2-[7-(2-cyclopropylethynyl)-1-ethyl-imidazo[4,5-c]pyridin-2-yl]-1,2,4-triazol-3-amine a) A solution of 2-(7-bromo-1-ethyl-imidazo[4,5-c]pyridin-2-yl)-1,2,4-triazol-3-amine (0.10 g) and ethynylcyclopropane (1.5 equiv.) in 1.5 mL DMF and 0.5 mL triethylamine was degassed with N$_2$ for 10 min. CuI (0.02 equiv.) and PdCl$_2$(PPh$_3$)$_2$ (0.02 equiv.) were then added and the reaction mixture was stirred at 80° C. for 4 h. The reaction mixture was then quenched with water and extracted with ethyl acetate. The combined organic layers were washed with water and brine, dried over sodium sulphate and concentrated. The residue was then purified by Combiflash using 3-8% MeOH in DCM as the eluent system to give 2-[7-(2-cyclopropylethynyl)-1-ethyl-imidazo[4,5-c]pyridin-2-yl]-1,2,4-triazol-3-amine as a light brown solid.
Melting point: 188-192° C.

$^1$H NMR (400 MHz, DMSO-d6) δ ppm: 0.78-0.90 (m, 2H), 0.92-1.04 (m, 2H), 1.43 (t, J=7.0 Hz, 3H), 1.65-1.75 (m, 1H), 4.72 (q, J=7.0 Hz, 2H), 7.50 (s, 2H), 7.81 (s, 1H), 8.41 (br. s, 1H), 8.82-8.95 (m, 1H)

Example P7

Preparation of 2-[4-chloro-1-ethyl-7-(o-toll)imidazo[4,5-c]pyridin-2-yl]-1,2,4-triazol-3-amine a) 2-[1-ethyl-7-(o-tolyl)imidazo[4,5-c]pyridin-2-yl]-1,2,4-triazol-3-amine was prepared according to procedures described in example 2, using o-tolylboronic acid for the last step. To a solution of 2-[1-ethyl-7-(o-tolyl)imidazo[4,5-c]pyridin-2-yl]-1,2,4-triazol-3-amine (0.75 g) in 45 mL dichloromethane was added 3-chloroperbenzoic acid (2 equiv.) and the reaction mixture was stirred at RT for 10 h. Reaction mixture was then quenched with a solution of thiosulphate, water was added and the aqueous layer was extracted with 10% MeOH/DCM The combined organic layers were dried over sodium sulphate, concentrated under reduced pressure and the residue was purified by Combiflash using 0-10% MeOH in DCM as the eluent system to give 2-[1-ethyl-7-(o-tolyl)-5-oxido-imidazo[4,5-c]pyridin-5-ium-2-yl]-1,2,4-triazol-3-amine as a light brown solid.

Melting point: 221-26° C.

¹H NMR (400 MHz, DMSO-d6) δ ppm: 0.82 (t, J=7.0 Hz, 3H), 2.13 (s, 3H), 3.66 (m, 1H), 4.08 (m, 1H) 7.34-7.50 (m, 4H) 7.53 (s, 2H) 7.76 (s, 1H) 7.91 (d, J=1.76 Hz, 1H) 8.76 (d, J=1.76 Hz, 1H).

b) A mixture of 2-[1-ethyl-7-(o-tolyl)-5-oxido-imidazo[4,5-c]pyridin-5-ium-2-yl]-1,2,4-triazol-3-amine (0.08 g) in 2.5 mL POCl₃ was heated under reflux for 5 h. The reaction mixture was then slowly poured onto crushed ice, neutralised with sodium bicarbonate and extracted with ethyl acetate. The combined organic layers were washed with water and brine, dried over sodium sulphate and concentrated under reduced pressure. The residue was then purified by Combiflash using 0-10% MeOH in DCM as the eluent system to give 2-[4-chloro-1-ethyl-7-(o-tolyl)imidazo[4,5-c]pyridin-2-yl]-1,2,4-triazol-3-amine as a brown solid.

Melting point: 274-278° C.

¹H NMR (400 MHz, DMSO-d6) δ ppm: 0.79 (t, J=7.0 Hz, 3H) 2.03 (s, 3H) 3.68 (m, 1H) 4.06 (m, 1H) 7.28-7.48 (m, 6H) 7.72 (s, 1H) 7.92 (s, 1H).

Example P8

Preparation of 1-[2-(5-amino-1,2,4-triazol-1-yl)-1-ethyl-imidazo[4,5-c]pyridin-7-yl]ethanol a) To a mixture of 1-[2-(5-amino-1,2,4-triazol-1-yl)-1-ethyl-imidazo[4,5-c]pyridin-7-yl]ethanone (0.025 g) in 0.75 mL of methanol (30 mL/g, 100 mass %) was slowly added sodium borohydride (2 equiv.) The reaction mixture was stirred at RT for 3 h after which it was concentrated under reduced pressure, and redissolved in ethyl acetate. The organic layer was washed with water and brine, dried over sodium sulphate and concentrated under reduced pressure. The crude material was then purified by Combiflash using 0-5% MeOH in DCM to afford 1-[2-(5-amino-1,2,4-triazol-1-yl)-1-ethyl-imidazo[4,5-c]pyridin-7-yl]ethanol as an off-white solid.

Melting point: 220-226° C.

Example P9

Preparation of 2-(7-bromo-1-ethyl-imidazo[4,5-c]pyridin-2-yl)-N,N-dimethyl-1,2,4-triazol-3-amine and 2-(7-bromo-1-ethyl-imidazo[4,5-c]pyridin-2-yl)-N-methyl-1,2,4-triazol-3-amine a) To a mixture of sodium hydride (2 equiv., 60% in oil) in 4 mL DMF at 0° C. was added 2-(7-bromo-1-ethyl-imidazo[4,5-c]pyridin-2-yl)-1,2,4-triazol-3-amine (0.20 g). The reaction mixture was stirred at room temperature for 20 min and then iodomethane (1.1 equivalent) was added. The reaction mixture was warmed to room temperature and stirred until no further evolution was observed. The reaction mixture was then quenched with water and extracted with ethyl acetate. The combined organic layers were dried over sodium sulphate and concentrated under reduced pressure. The crude oily residue was left still until some solid material settles down at the bottom of the round bottom flask. The organic residue was decanted and the solid mass so obtained was washed two times with diethyl ether and dried in vacuo to afford 2-(7-bromo-1-ethyl-imidazo[4,5-c]pyridin-2-yl)-N,N-dimethyl-1,2,4-triazol-3-amine as a yellow solid. A small amount of 2-(7-bromo-1-ethyl-imidazo[4,5-c]pyridin-2-yl)-N-methyl-1,2,4-triazol-3-amine was also formed (LCMS; RT=1.60, method B, [M+H]=321. 2-(7-bromo-1-ethyl-imidazo[4,5-c]pyridin-2-yl)-N,N-dimethyl-1,2,4-triazol-3-amine Melting point: 159-161° C.

¹H NMR (400 MHz, DMSO-d6) δ ppm: 1.47 (t, J=7.1 Hz, 3H) 2.84 (s, 6H) 4.47 (q, J=7.1 Hz, 2H) 7.89 (s, 1H) 8.60 (s, 1H) 9.00 (s, 1H)

Example P10

Preparation of 2-[7-[N-[(E)-3-chlorobut-2-enoxy]-C-methyl-carbonimidoyl]-1-ethyl-imidazo[4,5-c]pyridin-2-yl]-1,2,4-triazol-3-amine To a solution of 1-[2-(5-amino-1,2,4-triazol-1-yl)-1-ethyl-imidazo[4,5-c]pyridin-7-yl]ethanone (0.100 g, 0.369 mmol) in 3.7 mL acetonitrile was added O-[(E)-3-chlorobut-2-enyl] hydroxylamine hydrochloride (0.291 g, 1.84 mmol) followed by 4-methylbenzenesulfonic acid (0.021 g, 0.12 mmol). The reaction mixture was heated at 120° C. under MW irradiation for 20 min. Water was added and the solution was extracted with AcOEt. The combined organic layers were washed with a sat. solution of NaHCO₃ and water, dried over MgSO₄, filtered, concentrated and purified as follow:

Autopurification System from Waters: 2767 sample Manager, 2489 UV/Visible Detector, 2545 Quaternary Gradient Module.

Column: Phenomenex Gemini NX C18, 4 micron particle size, 80 Angström, 75×30.00 mm, DAD Wavelength (nm): 220 and 254

Solvent Gradient: Reversed Phase

| Time | A % | B % | Flow (ml/min) |
|------|-----|-----|---------------|
| 0.00 | 80  | 20  | 50.00         |
| 0.01 | 80  | 20  | 50.00         |
| 6.00 | 65  | 35  | 50.00         |
| 7.90 | 65  | 35  | 50.00         |
| 8.00 | 0   | 100 | 50.00         |
| 8.90 | 0   | 100 | 50.00         |
| 9.00 | 80  | 20  | 50.00         |
| 10.0 | 80  | 20  | 50.00         |

A = water (in House-HPLC quality)
B = Acetonitrile for prep. HPLC to give 2-[7-[(Z)—N-[(E)-3-chlorobut-2-enoxy]-C-methyl-carbonimidoyl]-1-ethyl-imidazo[4,5-c]pyridin-2-yl]-1,2,4-triazol-3-amine (0.057 g, 0.15 mmol, 41% Yield) and 2-[7-[(E)-N-[(E)-3-chlorobut-2-enoxy]-C-methyl-carbonimidoyl]-1-ethyl-imidazo[4,5-c]pyridin-2-yl]-1,2,4-triazol-3-amine (0.030 g, 0.080 mmol, 22% Yield) as white solids.

2-[7-[(E)-N-[(E)-3-chlorobut-2-enoxy]-C-methyl-carbonimidoyl]-1-ethyl-imidazo[4,5-c]pyridin-2-yl]-1,2,4-triazol-3-amine: ¹H NMR (400 MHz, CDCl₃) δ ppm 1.26 (t, J=7.1 Hz, 3H), 2.02 (q, J=1.1 Hz, 3H), 2.32 (s, 3H), 4.36-4.47 (m, 1H), 4.54-4.66 (m, 2H), 4.78-4.87 (m, 1H), 5.53 (td, J=6.1, 1.3 Hz, 1H), 6.63 (br. s, 2H), 7.58 (s, 1H), 8.11 (br. s, 1H), 8.88 (br. s, 1H)

2-[7-[(Z)—N-[(E)-3-chlorobut-2-enoxy]-C-methyl-carbonimidoyl]-1-ethyl-imidazo[4,5-c]pyridin-2-yl]-1,2,4-triazol-3-amine: ¹H NMR (400 MHz, CDCl₃) δ ppm 1.25 (t, J=7.0 Hz, 3H), 2.10 (q, J=1.2 Hz, 3H), 2.33 (s, 3H), 4.77-4.85 (m, 4H), 5.73 (tq, J=6.1, 1.3 Hz, 1H), 6.53 (br. s, 2H), 7.59 (s, 1H), 8.30 (br. s, 1H), 8.90 (br. s, 1H)

TABLE 17

Physical data of compounds of formula (I):

| Entry | IUPAC Names | RT (min) | [M + H]+ (measured) | Method | MP (° C.) |
|---|---|---|---|---|---|
| 1 | 2-(1-cyclopropylimidazo[4,5-c]pyridin-2-yl)-1,2,4-triazol-3-amine | 0.22 | 242 | A | |
| 2 | 2-(1-cyclohexylimidazo[4,5-c]pyridin-2-yl)-1,2,4-triazol-3-amine | 0.96 | 284 | A | |
| 3 | 2-(1-cyclohexylimidazo[4,5-c]pyridin-2-yl)-5-(trifluoromethyl)-1,2,4-triazol-3-amine | | | | 203-206 |
| 4 | 2-(1-cyclohexylimidazo[4,5-c]pyridin-2-yl)-5-phenyl-1,2,4-triazol-3-amine | | | | 222-225 |
| 5 | 2-(1-cyclohexylimidazo[4,5-c]pyridin-2-yl)-5-methyl-1,2,4-triazol-3-amine | | | | 212-215 |
| 6 | 5-butyl-2-(1-cyclohexylimidazo[4,5-c]pyridin-2-yl)-1,2,4-triazol-3-amine | | | | 163-165 |
| 7 | 2-(1-cyclohexylimidazo[4,5-c]pyridin-2-yl)-5-ethyl-1,2,4-triazol-3-amine | | | | 198-203 |
| 8 | 2-(1-cyclohexylimidazo[4,5-c]pyridin-2-yl)-5-cyclopropyl-1,2,4-triazol-3-amine | | | | 196-199 |
| 9 | 5-benzyl-2-(1-cyclohexylimidazo[4,5-c]pyridin-2-yl)-1,2,4-triazol-3-amine | | | | 219-222 |
| 10 | 2-(1-benzylimidazo[4,5-c]pyridin-2-yl)-1,2,4-triazol-3-amine | | | | 224-229 |
| 11 | 1-(1-cyclohexylimidazo[4,5-c]pyridin-2-yl)-1,2,4-triazole-3,5-diamine | | | | 236-238 |
| 12 | 2-[1-(2-phenylethyl)imidazo[4,5-c]pyridin-2-yl]-1,2,4-triazol-3-amine | | | | 198-200 |
| 13 | 2-(1-propylimidazo[4,5-c]pyridin-2-yl)-1,2,4-triazol-3-amine | | | | 210-212 |
| 14 | 2-(1-methylimidazo[4,5-c]pyridin-2-yl)-1,2,4-triazol-3-amine | | | | 240-244 |
| 15 | 2-(7-bromo-1-ethylimidazo[4,5-c]pyridin-2-yl)-1,2,4-triazol-3-amine | | | | 231-232 |
| 16 | 2-(1-prop-1-enylimidazo[4,5-c]pyridin-2-yl)-1,2,4-triazol-3-amine | | | | 199-200 |
| 17 | 2-(1-prop-2-enylimidazo[4,5-c]pyridin-2-yl)-1,2,4-triazol-3-amine | | | | 215-216 |
| 18 | 2-(1H-imidazo[4,5-c]pyridin-2-yl)-1,2,4-triazol-3-amine | | | | 305-306 |
| 19 | 2-(1-ethyl-7-phenylimidazo[4,5-c]pyridin-2-yl)-1,2,4-triazol-3-amine | | | | 247-251 |
| 20 | 5-bromo-2-(1-cyclohexylimidazo[4,5-c]pyridin-2-yl)-1,2,4-triazol-3-amine | | | | 217-221 |
| 21 | 2-[1-ethyl-7-(2-phenylethenyl)imidazo[4,5-c]pyridin-2-yl]-1,2,4-triazol-3-amine | | | | 247-252 |
| 22 | 2-(1-ethyl-7-methylimidazo[4,5-c]pyridin-2-yl)-1,2,4-triazol-3-amine | | | | 194-198 |
| 23 | 2-(1,7-diethylimidazo[4,5-c]pyridin-2-yl)-1,2,4-triazol-3-amine | | | | 176-179 |
| 24 | 2-[1-ethyl-7-(2-phenylethyl)imidazo[4,5-c]pyridin-2-yl]-1,2,4-triazol-3-amine | | | | 205-208 |
| 25 | 2-(7-benzyl-1-ethylimidazo[4,5-c]pyridin-2-yl)-1,2,4-triazol-3-amine | | | | 220-224 |
| 26 | N-[2-(7-bromo-1-ethylimidazo[4,5-c]pyridin-2-yl)-1,2,4-triazol-3-yl]acetamide | | | | 238-240 |
| 27 | N-[2-[1-ethyl-7-(4-methylphenyl)imidazo[4,5-c]pyridin-2-yl]-1,2,4-triazol-3-yl]acetamide | | | | 251-253 |
| 28 | 2-[1-ethyl-7-(4-methylphenyl)imidazo[4,5-c]pyridin-2-yl]-1,2,4-triazol-3-amine | | | | 234-236 |
| 29 | 2-[1-ethyl-7-(4-fluorophenyl)imidazo[4,5-c]pyridin-2-yl]-1,2,4-triazol-3-amine | | | | 275-277 |
| 30 | 2-[1-ethyl-7-[4-(trifluoromethyl)phenyl]imidazo[4,5-c]pyridin-2-yl]-1,2,4-triazol-3-amine | 1.06 | 374 | U | |
| 31 | 2-[1-ethyl-7-[3-(trifluoromethyl)phenyl]imidazo[4,5-c]pyridin-2-yl]-1,2,4-triazol-3-amine | 1.05 | 374 | U | |
| 32 | 2-[1-ethyl-7-[2-(trifluoromethyl)phenyl]imidazo[4,5-c]pyridin-2-yl]-1,2,4-triazol-3-amine | 1.00 | 374 | U | |
| 33 | 2-[7-(2-chlorophenyl)-1-ethylimidazo[4,5-c]pyridin-2-yl]-1,2,4-triazol-3-amine | 0.92 | 340 | U | |
| 34 | 2-[7-(3-chlorophenyl)-1-ethylimidazo[4,5-c]pyridin-2-yl]-1,2,4-triazol-3-amine | 0.96 | 340 | U | |
| 35 | 2-[7-(4-chlorophenyl)-1-ethylimidazo[4,5-c]pyridin-2-yl]-1,2,4-triazol-3-amine | 0.95 | 340 | U | |
| 36 | 2-[7-(3,4-dichlorophenyl)-1-ethylimidazo[4,5-c]pyridin-2-yl]-1,2,4-triazol-3-amine | 1.12 | 374 | U | |
| 37 | 2-[7-(3,5-difluorophenyl)-1-ethylimidazo[4,5-c]pyridin-2-yl]-1,2,4-triazol-3-amine | 0.92 | 342 | U | |
| 38 | 2-[7-(2,4-dichlorophenyl)-1-ethylimidazo[4,5-c]pyridin-2-yl]-1,2,4-triazol-3-amine | 1.13 | 374 | U | |
| 39 | 2-[7-(2,5-difluorophenyl)-1-ethylimidazo[4,5-c]pyridin-2-yl]-1,2,4-triazol-3-amine | 0.91 | 342 | U | |
| 40 | 2-(1-ethyl-7-naphthalen-1-ylimidazo[4,5-c]pyridin-2-yl)-1,2,4-triazol-3-amine | 1.01 | 356 | U | |
| 41 | 2-[1-ethyl-7-(3-fluoro-4-methylphenyl)imidazo[4,5-c]pyridin-2-yl]-1,2,4-triazol-3-amine | 0.96 | 338 | U | |
| 42 | 2-[1-ethyl-7-(4-morpholin-4-ylphenyl)imidazo[4,5-c]pyridin-2-yl]-1,2,4-triazol-3-amine | 0.78 | 390 | U | |
| 43 | 2-[1-ethyl-7-(3-fluoro-4-methoxyphenyl)imidazo[4,5-c]pyridin-2-yl]-1,2,4-triazol-3-amine | 0.82 | 354 | U | |
| 44 | 2-[1-ethyl-7-(4-methyl-3-nitrophenyl)imidazo[4,5-c]pyridin-2-yl]-1,2,4-triazol-3-amine | 0.93 | 365 | U | |
| 45 | 2-[7-(2,4-dimethylphenyl)-1-ethylimidazo[4,5-c]pyridin-2-yl]-1,2,4-triazol-3-amine | 0.98 | 334 | U | |
| 46 | 2-[7-(3,4-dimethylphenyl)-1-ethylimidazo[4,5-c]pyridin-2-yl]-1,2,4-triazol-3-amine | 0.99 | 334 | U | |
| 47 | 2-[1-ethyl-7-(4-methoxy-3,5-dimethylphenyl)imidazo[4,5-c]pyridin-2-yl]-1,2,4-triazol-3-amine | 0.97 | 364 | U | |
| 48 | 2-[7-(2,2-difluoro-1,3-benzodioxol-4-yl)-1-ethylimidazo[4,5-c]pyridin-2-yl]-1,2,4-triazol-3-amine | 1.12 | 386 | U | |
| 49 | 2-[7-[4-chloro-3-(trifluoromethyl)phenyl]-1-ethylimidazo[4,5-c]pyridin-2-yl]-1,2,4-triazol-3-amine | 1.21 | 408 | U | |
| 50 | 2-(1-ethyl-7-pyrimidin-5-ylimidazo[4,5-c]pyridin-2-yl)-1,2,4-triazol-3-amine | 0.51 | 308 | U | |
| 51 | 2-[7-(1-benzofuran-2-yl)-1-ethylimidazo[4,5-c]pyridin-2-yl]-1,2,4-triazol-3-amine | 1.16 | 346 | U | |
| 52 | 2-[7-(2,5-dimethylthiophen-3-yl)-1-ethylimidazo[4,5-c]pyridin-2-yl]-1,2,4-triazol-3-amine | 0.98 | 340 | U | |
| 53 | 2-[1-ethyl-7-(2-methoxypyrimidin-5-yl)imidazo[4,5-c]pyridin-2-yl]-1,2,4-triazol-3-amine | 0.60 | 338 | U | |
| 54 | 2-[1-ethyl-7-[6-(4-fluorophenyl)pyridin-3-yl]imidazo[4,5-c]pyridin-2-yl]-1,2,4-triazol-3-amine | 1.05 | 401 | U | |
| 55 | 2-[1-ethyl-7-(furan-3-yl)imidazo[4,5-c]pyridin-2-yl]-1,2,4-triazol-3-amine | 0.65 | 296 | U | |
| 56 | 2-[7-(2,6-dimethoxypyridin-3-yl)-1-ethylimidazo[4,5-c]pyridin-2-yl]-1,2,4-triazol-3-amine | 0.88 | 367 | U | |
| 57 | 2-(1-ethyl-7-isoquinolin-4-ylimidazo[4,5-c]pyridin-2-yl)-1,2,4-triazol-3-amine | 0.72 | 357 | U | |
| 58 | 2-[1-ethyl-7-(2-methoxypyridin-3-yl)imidazo[4,5-c]pyridin-2-yl]-1,2,4-triazol-3-amine | 0.71 | 337 | U | |
| 59 | 2-[1-ethyl-7-(6-methoxypyridin-3-yl)imidazo[4,5-c]pyridin-2-yl]-1,2,4-triazol-3-amine | 0.71 | 337 | U | |
| 60 | 2-[1-ethyl-7-(2-fluoropyridin-4-yl)imidazo[4,5-c]pyridin-2-yl]-1,2,4-triazol-3-amine | 0.69 | 325 | U | |
| 61 | 2-[1-ethyl-7-(1-methylpyrazol-4-yl)imidazo[4,5-c]pyridin-2-yl]-1,2,4-triazol-3-amine | 0.51 | 310 | U | |
| 62 | 2-(1-ethyl-7-isoquinolin-5-ylimidazo[4,5-c]pyridin-2-yl)-1,2,4-triazol-3-amine | 0.60 | 357 | U | |
| 63 | 2-[1-ethyl-7-[6-(trifluoromethyl)pyridin-3-yl]imidazo[4,5-c]pyridin-2-yl]-1,2,4-triazol-3-amine | 0.91 | 375 | U | |
| 64 | 2-[7-(5-chloropyridin-3-yl)-1-ethylimidazo[4,5-c]pyridin-2-yl]-1,2,4-triazol-3-amine | 0.77 | 341 | U | |
| 65 | 2-[7-(6-chloro-5-methylpyridin-3-yl)-1-ethylimidazo[4,5-c]pyridin-2-yl]-1,2,4-triazol-3-amine | 0.85 | 355 | U | |
| 66 | 2-[1-ethyl-7-(2-fluoroquinolin-3-yl)imidazo[4,5-c]pyridin-2-yl]-1,2,4-triazol-3-amine | 0.97 | 375 | U | |
| 67 | 2-(1-ethyl-7-prop-1-enylimidazo[4,5-c]pyridin-2-yl)-1,2,4-triazol-3-amine | 0.65 | 270 | U | |
| 68 | 2-(1-ethyl-7-pent-1-enylimidazo[4,5-c]pyridin-2-yl)-1,2,4-triazol-3-amine | 0.90 | 298 | U | |
| 69 | 2-[7-[2-(4-chlorophenyl)ethenyl]-1-ethylimidazo[4,5-c]pyridin-2-yl]-1,2,4-triazol-3-amine | 1.11 | 366 | U | |
| 70 | 2-[7-(2-cyclohexylethenyl)-1-ethylimidazo[4,5-c]pyridin-2-yl]-1,2,4-triazol-3-amine | 1.14 | 338 | U | |
| 71 | 2-[1-ethyl-7-[2-(4-methylphenyl)ethenyl]imidazo[4,5-c]pyridin-2-yl]-1,2,4-triazol-3-amine | 1.06 | 346 | U | |
| 72 | 2-[1-ethyl-7-(2-methylphenyl)imidazo[4,5-c]pyridin-2-yl]-1,2,4-triazol-3-amine | 0.87 | 320 | U | |
| 73 | 2-(1-ethyl-7-propylimidazo[4,5-c]pyridin-2-yl)-1,2,4-triazol-3-amine | 0.65 | 272 | U | |
| 74 | 2-[7-(1-ethoxyethenyl)-1-ethylimidazo[4,5-c]pyridin-2-yl]-1,2,4-triazol-3-amine | | | | 193-195 |

TABLE 17-continued

Physical data of compounds of formula (I):

| Entry | IUPAC Names | RT (min) | [M + H]+ (measured) | Method | MP (° C.) |
|---|---|---|---|---|---|
| 75 | 1-[2-(5-amino-1,2,4-triazol-1-yl)-1-ethylimidazo[4,5-c]pyridin-7-yl]ethanone | | | | 242-244 |
| 76 | 2-[7-bromo-1-(2,2,2-trifluoroethyl)imidazo[4,5-c]pyridin-2-yl]-1,2,4-triazol-3-amine | | | | 234-236 |
| 77 | 2-(6-bromo-1-ethyl-7-methoxyimidazo[4,5-c]pyridin-2-yl)-1,2,4-triazol-3-amine | | | | 247-249 |
| 78 | 2-[7-[3,5-bis(trifluoromethyl)phenyl]-1-ethylimidazo[4,5-c]pyridin-2-yl]-1,2,4-triazol-3-amine | 1.52 | 442 | U | |
| 79 | 2-[1-ethyl-7-(2-fluorophenyl)imidazo[4,5-c]pyridin-2-yl]-1,2,4-triazol-3-amine | 1.02 | 324 | U | |
| 80 | 2-[7-(2,4-difluorophenyl)-1-ethylimidazo[4,5-c]pyridin-2-yl]-1,2,4-triazol-3-amine | 1.09 | 342 | U | |
| 81 | 2-[7-(2,4-dimethoxyphenyl)-1-ethylimidazo[4,5-c]pyridin-2-yl]-1,2,4-triazol-3-amine | 1 | 366 | U | |
| 82 | 2-[7-(2,3-dimethylphenyl)-1-ethylimidazo[4,5-c]pyridin-2-yl]-1,2,4-triazol-3-amine | 1.12 | 334 | U | |
| 83 | 2-[7-(2,3-dimethoxyphenyl)-1-ethylimidazo[4,5-c]pyridin-2-yl]-1,2,4-triazol-3-amine | 1.01 | 366 | U | |
| 84 | 2-[1-ethyl-7-[2-fluoro-5-(trifluoromethyl)phenyl]imidazo[4,5-c]pyridin-2-yl]-1,2,4-triazol-3-amine | 1.3 | 392 | U | |
| 85 | 2-[2-(5-amino-1,2,4-triazol-1-yl)-1-ethylimidazo[4,5-c]pyridin-7-yl]benzonitrile | 0.97 | 331 | U | |
| 86 | 2-[1-ethyl-7-(2,3,4-trifluorophenyl)imidazo[4,5-c]pyridin-2-yl]-1,2,4-triazol-3-amine | 1.2 | 360 | U | |
| 87 | 2-[7-(2,3-dichlorophenyl)-1-ethylimidazo[4,5-c]pyridin-2-yl]-1,2,4-triazol-3-amine | 1.26 | 374 | U | |
| 88 | 2-[7-(2,5-dichlorophenyl)-1-ethylimidazo[4,5-c]pyridin-2-yl]-1,2,4-triazol-3-amine | 1.29 | 374 | U | |
| 89 | 2-[1-ethyl-7-(2-fluoropyridin-3-yl)imidazo[4,5-c]pyridin-2-yl]-1,2,4-triazol-3-amine | 0.87 | 325 | U | |
| 90 | 2-[7-(3-chloro-2-fluorophenyl)-1-ethylimidazo[4,5-c]pyridin-2-yl]-1,2,4-triazol-3-amine | 1.22 | 358 | U | |
| 91 | 2-[7-(5-chloro-2-fluorophenyl)-1-ethylimidazo[4,5-c]pyridin-2-yl]-1,2,4-triazol-3-amine | 1.2 | 358 | U | |
| 92 | 2-[1-ethyl-7-(4-fluoro-2-methylphenyl)imidazo[4,5-c]pyridin-2-yl]-1,2,4-triazol-3-amine | 1.08 | 338 | U | |
| 93 | 2-[1-ethyl-7-(2-fluoro-3-methoxyphenyl)imidazo[4,5-c]pyridin-2-yl]-1,2,4-triazol-3-amine | 1.03 | 354 | U | |
| 94 | 2-[7-(2-chloro-4-methoxyphenyl)-1-ethylimidazo[4,5-c]pyridin-2-yl]-1,2,4-triazol-3-amine | 1.12 | 370 | U | |
| 95 | 2-[1-ethyl-7-(4-fluoro-2-methoxyphenyl)imidazo[4,5-c]pyridin-2-yl]-1,2,4-triazol-3-amine | 1.03 | 354 | U | |
| 96 | 2-[1-ethyl-7-(2-fluoro-4-methoxyphenyl)imidazo[4,5-c]pyridin-2-yl]-1,2,4-triazol-3-amine | 1.06 | 354 | U | |
| 97 | 2-[7-[2-chloro-4-(trifluoromethyl)phenyl]-1-ethylimidazo[4,5-c]pyridin-2-yl]-1,2,4-triazol-3-amine | 1.42 | 408 | U | |
| 98 | 2-[7-(4-chloro-2-fluorophenyl)-1-ethylimidazo[4,5-c]pyridin-2-yl]-1,2,4-triazol-3-amine | 1.23 | 358 | U | |
| 99 | 2-[7-(3-chloro-2-methylphenyl)-1-ethylimidazo[4,5-c]pyridin-2-yl]-1,2,4-triazol-3-amine | 1.21 | 354 | U | |
| 100 | 2-[7-(3,4-dichloro-2-fluorophenyl)-1-ethylimidazo[4,5-c]pyridin-2-yl]-1,2,4-triazol-3-amine | 1.4 | 392 | U | |
| 101 | 2-[7-(2-chloro-4-fluorophenyl)-1-ethylimidazo[4,5-c]pyridin-2-yl]-1,2,4-triazol-3-amine | 1.16 | 358 | U | |
| 102 | 2-[7-(2,3-difluorophenyl)-1-ethylimidazo[4,5-c]pyridin-2-yl]-1,2,4-triazol-3-amine | 1.12 | 342 | U | |
| 103 | 2-[7-(2-chloropyridin-3-yl)-1-ethylimidazo[4,5-c]pyridin-2-yl]-1,2,4-triazol-3-amine | 0.91 | 341 | U | |
| 104 | N-[3-[2-(5-amino-1,2,4-triazol-1-yl)-1-ethylimidazo[4,5-c]pyridin-7-yl]phenyl]acetamide | 0.84 | 363 | U | |
| 105 | 1-[2-(5-amino-1,2,4-triazol-1-yl)-1-ethylimidazo[4,5-c]pyridin-7-yl]ethanol | | | | 220-226 |
| 106 | 2-(7-ethenyl-1-ethylimidazo[4,5-c]pyridin-2-yl)-1,2,4-triazol-3-amine | | | | 178-186 |
| 107 | tert-butyl 4-[2-(5-amino-1,2,4-triazol-1-yl)-1-ethylimidazo[4,5-c]pyridin-7-yl]-3,6-dihydro-2H-pyridine-1-carboxylate | | | | 183-186 |
| 108 | 1-[2-(5-amino-1,2,4-triazol-1-yl)-1-ethylimidazo[4,5-c]pyridin-7-yl]-3-(4-fluorophenyl)prop-2-en-1-one | | | | 205-209 |
| 109 | 2-[1-ethyl-7-(3-phenyl-4,5-dihydro-1,2-oxazol-5-yl)imidazo[4,5-c]pyridin-2-yl]-1,2,4-triazol-3-amine | | | | 201-209 |
| 110 | 2-(7-bromo-1-propylimidazo[4,5-c]pyridin-2-yl)-1,2,4-triazol-3-amine | | | | 207-208 |
| 111 | 2-(7-bromo-1-cyclopropylimidazo[4,5-c]pyridin-2-yl)-1,2,4-triazol-3-amine | | | | 186-192 |
| 112 | 2-(7-bromo-1-cyclohexylimidazo[4,5-c]pyridin-2-yl)-1,2,4-triazol-3-amine | | | | 217-218 |
| 113 | 1-[2-(7-acetyl-1-ethylimidazo[4,5-c]pyridin-2-yl)-1,2,4-triazol-3-yl]pyrrolidine-2,5-dione | 0.67 | 354 | A | |
| 114 | 1-[2-[7-(2,4-dichlorophenyl)-1-ethylimidazo[4,5-c]pyridin-2-yl]-1,2,4-triazol-3-yl]pyrrolidine-2,5-dione | 0.94 | 456 | A | |
| 115 | 4-[2-(5-amino-1,2,4-triazol-1-yl)-1-ethylimidazo[4,5-c]pyridin-7-yl]-2-methylbut-3-yn-2-ol | | | | 253-259 |
| 116 | 2-[1-ethyl-7-[2-(4-methylphenyl)ethynyl]imidazo[4,5-c]pyridin-2-yl]-1,2,4-triazol-3-amine | | | | 211-218 |
| 117 | 2-[4-chloro-1-ethyl-7-(2-methylphenyl)imidazo[4,5-c]pyridin-2-yl]-1,2,4-triazol-3-amine | | | | 274-278 |
| 118 | 2-[7-(2,4-dichlorophenyl)-1-propylimidazo[4,5-c]pyridin-2-yl]-1,2,4-triazol-3-amine | 0.90 | 388 | A | |
| 119 | 2-[1-cyclopropyl-7-(2,4-dichlorophenyl)imidazo[4,5-c]pyridin-2-yl]-1,2,4-triazol-3-amine | 0.81 | 386 | A | |
| 120 | 2-[1-cyclohexyl-7-(2,4-dichlorophenyl)imidazo[4,5-c]pyridin-2-yl]-1,2,4-triazol-3-amine | 0.96 | 428 | A | |
| 121 | 2-[7-(2-fluorophenyl)-1-propylimidazo[4,5-c]pyridin-2-yl]-1,2,4-triazol-3-amine | 0.75 | 338 | A | |
| 122 | 2-[1-cyclopropyl-7-(2-fluorophenyl)imidazo[4,5-c]pyridin-2-yl]-1,2,4-triazol-3-amine | 0.89 | 329 | A | |
| 123 | 2-[7-(2-cyclopropylethynyl)-1-ethylimidazo[4,5-c]pyridin-2-yl]-1,2,4-triazol-3-amine | | | | 188-192 |
| 124 | 2-[1-ethyl-7-(2-methylphenyl)-5-oxidoimidazo[4,5-c]pyridin-5-ium-2-yl]-1,2,4-triazol-3-amine | | | | 221-226 |
| 125 | 2-[7-(2-chlorophenyl)-1-cyclopropylimidazo[4,5-c]pyridin-2-yl]-1,2,4-triazol-3-amine | 0.69 | 352 | A | |
| 126 | 2-[7-(2-chlorophenyl)-1-cyclohexylimidazo[4,5-c]pyridin-2-yl]-1,2,4-triazol-3-amine | 0.86 | 394 | A | |
| 127 | 2-[1-cyclohexyl-7-(2-fluorophenyl)imidazo[4,5-c]pyridin-2-yl]-1,2,4-triazol-3-amine | 0.83 | 378 | A | |
| 128 | 2-(5-amino-1,2,4-triazol-1-yl)-1-ethylimidazo[4,5-c]pyridine-7-carbonitrile | 0.66 | 255 | A | |
| 129 | 2-(5-amino-1,2,4-triazol-1-yl)-1-propylimidazo[4,5-c]pyridine-7-carbonitrile | 0.73 | 269 | A | |
| 130 | 2-(5-amino-1,2,4-triazol-1-yl)-1-cyclopropylimidazo[4,5-c]pyridine-7-carbonitrile | 0.57 | 267 | A | |
| 131 | 2-(5-amino-1,2,4-triazol-1-yl)-1-cyclohexylimidazo[4,5-c]pyridine-7-carbonitrile | 0.81 | 309 | A | |
| 132 | 2-(7-bromo-1-ethylimidazo[4,5-c]pyridin-2-yl)-N,N-dimethyl-1,2,4-triazol-3-amine | 1.30 | 336 | B | 159-161 |
| 133 | 2-[1-ethyl-7-[N-methoxy-C-methyl-carbonimidoyl]imidazo[4,5-c]pyridin-2-yl]-1,2,4-triazol-3-amine | 1.09/1.15 | 301 | B | 170-173 |
| 134 | 2-[7-[N-ethoxy-C-methyl-carbonimidoyl]-1-ethyl-imidazo[4,5-c]pyridin-2-yl]-1,2,4-triazol-3-amine | 0.82/0.87 | 315 | U | 160-165 |
| 135 | 2-[1-ethyl-7-[N-[(4-fluorophenyl)methoxy]-C-methyl-carbonimidoyl]imidazo[4,5-c]pyridin-2-yl]-1,2,4-triazol-3-amine | 1.56 | 395 | B | 175-187 |
| 136 | 1-[2-(5-amino-1,2,4-triazol-1-yl)-1-ethyl-imidazo[4,5-c]pyridin-7-yl]ethanone oxime | 1.11/1.17 | 287 | B | 228-240 |
| 137 | 2-[1-ethyl-7-[N-[(2-fluorophenyl)methoxy]-C-methyl-carbonimidoyl]imidazo[4,5-c]pyridin-2-yl]-1,2,4-triazol-3-amine | 1.53 | 395 | B | 159-171 |
| 138 | 2-[7-[N-allyloxy-C-methyl-carbonimidoyl]-1-ethyl-imidazo[4,5-c]pyridin-2-yl]-1,2,4-triazol-3-amine | 1.34 | 327 | B | 142-146 |

TABLE 17-continued

Physical data of compounds of formula (I):

| Entry | IUPAC Names | RT (min) | [M + H]+ (measured) | Method | MP (° C.) |
|---|---|---|---|---|---|
| 139 | 2-[1-ethyl-7-[C-methyl-N-(p-tolylmethoxy)carbonimidoyl]imidazo[4,5-c]pyridin-2-yl]-1,2,4-triazol-3-amine | 1.57/1.62 | 391 | B | |
| 140 | 2-[7-[N-tert-butoxy-C-methyl-carbonimidoyl]-1-ethyl-imidazo[4,5-c]pyridin-2-yl]-1,2,4-triazol-3-amine | 1.09/1.14 | 343 | U | 171-175 |
| 141 | 2-[7-[N-(cyclopropylmethoxy)-C-methyl-carbonimidoyl]-1-ethyl-imidazo[4,5-c]pyridin-2-yl]-1,2,4-triazol-3-amine | 1.38/1.41 | 341 | B | 151-163 |
| 142 | 2-[1-ethyl-7-[C-methyl-N-(2-pyridylmethoxy)carbonimidoyl]imidazo[4,5-c]pyridin-2-yl]-1,2,4-triazol-3-amine | 1.03 | 378 | B | 138-149 |
| 143 | 2-[1-ethyl-7-[C-methyl-N-propoxy-carbonimidoyl]imidazo[4,5-c]pyridin-2-yl]-1,2,4-triazol-3-amine | 0.96/1.03 | 329 | U | |
| 144 | 2-[7-[N-[(2-chlorophenyl)methoxy]-C-methyl-carbonimidoyl]-1-ethyl-imidazo[4,5-c]pyridin-2-yl]-1,2,4-triazol-3-amine | 1.21/1.29 | 411 | U | |
| 145 | 2-[7-[N-[(4-chlorophenyl)methoxy]-C-methyl-carbonimidoyl]-1-ethyl-imidazo[4,5-c]pyridin-2-yl]-1,2,4-triazol-3-amine | 1.24/1.28 | 411 | U | |
| 146 | 2-[1-ethyl-7-[N-[(2-methoxyphenyl)methoxy]-C-methyl-carbonimidoyl]imidazo[4,5-c]pyridin-2-yl]-1,2,4-triazol-3-amine | 1.10/1.15 | 407 | U | |
| 147 | 2-[1-ethyl-7-[(Z)-N-hexoxy-C-methyl-carbonimidoyl]imidazo[4,5-c]pyridin-2-yl]-1,2,4-triazol-3-amine | 1.34 | 371 | U | |
| 148 | 2-[1-ethyl-7-[(E)-N-hexoxy-C-methyl-carbonimidoyl]imidazo[4,5-c]pyridin-2-yl]-1,2,4-triazol-3-amine | 1.44 | 371 | U | |
| 149 | 2-[7-[(Z)-N-[(E)-3-chloroallyloxy]-C-methyl-carbonimidoyl]-1-ethyl-imidazo[4,5-c]pyridin-2-yl]-1,2,4-triazol-3-amine | 1.00 | 361 | U | |
| 150 | 2-[7-[(E)-N-[(E)-3-chloroallyloxy]-C-methyl-carbonimidoyl]-1-ethyl-imidazo[4,5-c]pyridin-2-yl]-1,2,4-triazol-3-amine | 1.05 | 361 | U | |
| 151 | 2-[7-[(Z)-N-(2-chloroallyloxy)-C-methyl-carbonimidoyl]-1-ethyl-imidazo[4,5-c]pyridin-2-yl]-1,2,4-triazol-3-amine | 1.00 | 361 | U | |
| 152 | 2-[7-[(E)-N-(2-chloroallyloxy)-C-methyl-carbonimidoyl]-1-ethyl-imidazo[4,5-c]pyridin-2-yl]-1,2,4-triazol-3-amine | 1.06 | 361 | U | |
| 153 | 2-[7-[(Z)-N-[(E)-3-chlorobut-2-enoxy]-C-methyl-carbonimidoyl]-1-ethyl-imidazo[4,5-c]pyridin-2-yl]-1,2,4-triazol-3-amine | 1.11 | 375 | U | |
| 154 | 2-[7-[(E)-N-[(E)-3-chlorobut-2-enoxy]-C-methyl-carbonimidoyl]-1-ethyl-imidazo[4,5-c]pyridin-2-yl]-1,2,4-triazol-3-amine | 1.16 | 375 | U | |
| 155 | 2-[7-[N-(3,3-dichloroallyloxy)-C-methyl-carbonimidoyl]-1-ethyl-imidazo[4,5-c]pyridin-2-yl]-1,2,4-triazol-3-amine | 1.17/1.22 | 395 | U | |
| 156 | 2-[1-ethyl-7-[(Z)-C-methyl-N-(3-methylbut-2-enoxy)carbonimidoyl]imidazo[4,5-c]pyridin-2-yl]-1,2,4-triazol-3-amine | 1.11 | 355 | U | |
| 157 | 2-[1-ethyl-7-[(E)-C-methyl-N-(3-methylbut-2-enoxy)carbonimidoyl]imidazo[4,5-c]pyridin-2-yl]-1,2,4-triazol-3-amine | 1.16 | 355 | U | |
| 158 | ethyl 2-[(Z)-1-[2-(5-amino-1,2,4-triazol-1-yl)-1-ethyl-imidazo[4,5-c]pyridin-7-yl]ethylideneamino]oxypropanoate | 0.96 | 387 | U | |
| 159 | ethyl 2-[(E)-1-[2-(5-amino-1,2,4-triazol-1-yl)-1-ethyl-imidazo[4,5-c]pyridin-7-yl]ethylideneamino]oxypropanoate | 0.99 | 387 | U | |
| 160 | 2-[7-[N-[(2,6-dichlorophenyl)methoxy]-C-methyl-carbonimidoyl]-1-ethyl-imidazo[4,5-c]pyridin-2-yl]-1,2,4-triazol-3-amine | 1.29/1.37 | 445 | U | |
| 161 | 2-[1-ethyl-7-[(Z)-N-isobutoxy-C-methyl-carbonimidoyl]imidazo[4,5-c]pyridin-2-yl]-1,2,4-triazol-3-amine | 1.07 | 343 | U | |
| 162 | 2-[1-ethyl-7-[(E)-N-isobutoxy-C-methyl-carbonimidoyl]imidazo[4,5-c]pyridin-2-yl]-1,2,4-triazol-3-amine | 1.16 | 343 | U | |
| 163 | 2-[1-ethyl-7-[C-methyl-N-[(2,3,4,5,6-pentafluorophenyl)methoxy]carbonimidoyl]imidazo[4,5-c]pyridin-2-yl]-1,2,4-triazol-3-amine | 1.30/1.35 | 467 | U | |
| 164 | 2-[1-ethyl-7-[C-methyl-N-[(2,4,5-trichlorophenyl)methoxy]carbonimidoyl]imidazo[4,5-c]pyridin-2-yl]-1,2,4-triazol-3-amine | 1.51/1.58 | 479 | U | |
| 165 | 2-[7-[N-benzyloxy-C-methyl-carbonimidoyl]-1-ethyl-imidazo[4,5-c]pyridin-2-yl]-1,2,4-triazol-3-amine | 1.10/1.16 | 377 | U | |
| 166 | 2-[1-ethyl-7-[(Z)-N-isopropoxy-C-methyl-carbonimidoyl]imidazo[4,5-c]pyridin-2-yl]-1,2,4-triazol-3-amine | 0.93 | 329 | U | |
| 167 | 2-[1-ethyl-7-[(E)-N-isopropoxy-C-methyl-carbonimidoyl]imidazo[4,5-c]pyridin-2-yl]-1,2,4-triazol-3-amine | 1.00 | 329 | U | |
| 168 | 2-[1-ethyl-7-[C-methyl-N-phenoxy-carbonimidoyl]imidazo[4,5-c]pyridin-2-yl]-1,2,4-triazol-3-amine | 1.15/1.20 | 363 | U | |
| 169 | 2-[1-ethyl-7-[C-methyl-N-(2,2,2-trifluoroethoxy)carbonimidoyl]imidazo[4,5-c]pyridin-2-yl]-1,2,4-triazol-3-amine | 0.97/1.03 | 369 | U | |
| 170 | 2-[7-[(Z)-N-[(Z)-3-chloroallyloxy]-C-methyl-carbonimidoyl]-1-ethyl-imidazo[4,5-c]pyridin-2-yl]-1,2,4-triazol-3-amine | 0.75 | 361 | A | |
| 171 | 2-[7-[(E)-N-[(Z)-3-chloroallyloxy]-C-methyl-carbonimidoyl]-1-ethyl-imidazo[4,5-c]pyridin-2-yl]-1,2,4-triazol-3-amine | 0.77 | 361 | A | |
| 172 | 2-[7-(2-chlorophenyl)-1-propyl-imidazo[4,5-c]pyridin-2-yl]-1,2,4-triazol-3-amine | 0.79 | 354 | A | |
| 173 | 2-(7-methyl-1-propyl-imidazo[4,5-c]pyridin-2-yl)-1,2,4-triazol-3-amine | 0.39 | 258 | A | |
| 174 | 2-(7-ethyl-1-propyl-imidazo[4,5-c]pyridin-2-yl)-1,2,4-triazol-3-amine | 0.55 | 272 | A | |
| 175 | 2-(1-cyclopropyl-7-methyl-imidazo[4,5-c]pyridin-2-yl)-1,2,4-triazol-3-amine | 0.18-0.23 | 256 | A | |
| 176 | 2-[7-[(Z)-N-[(E)-but-2-enoxy]-C-methyl-carbonimidoyl]-1-ethyl-imidazo[4,5-c]pyridin-2-yl]-1,2,4-triazol-3-amine | 0.76 | 341 | A | |
| 177 | 2-[7-[(E)-N-[(E)-but-2-enoxy]-C-methyl-carbonimidoyl]-1-ethyl-imidazo[4,5-c]pyridin-2-yl]-1,2,4-triazol-3-amine | 0.80 | 341 | A | |

TABLE 17-continued

Physical data of compounds of formula (I):

| Entry | IUPAC Names | RT (min) | [M + H]+ (measured) | Method | MP (° C.) |
|---|---|---|---|---|---|
| 178 | 2-[1-ethyl-7-[(Z)-C-methyl-N-(2-methylallyloxy)carbonimidoyl]imidazo[4,5-c]pyridin-2-yl]-1,2,4-triazol-3-amine | 0.76 | 341 | A | |
| 179 | 2-[1-ethyl-7-[(E)-C-methyl-N-(2-methylallyloxy)carbonimidoyl]imidazo[4,5-c]pyridin-2-yl]-1,2,4-triazol-3-amine | 0.79 | 341 | A | |
| 180 | 2-[7-[(Z)-N-[(Z)-3-chloroallyloxy]-C-methyl-carbonimidoyl]-1-propyl-imidazo[4,5-c]pyridin-2-yl]-1,2,4-triazol-3-amine | 0.82 | 375 | A | |
| 181 | 2-[7-[(E)-N-[(Z)-3-chloroallyloxy]-C-methyl-carbonimidoyl]-1-propyl-imidazo[4,5-c]pyridin-2-yl]-1,2,4-triazol-3-amine | 0.84 | 375 | A | |
| 182 | 2-[7-[(Z)-N-[(E)-3-chloroallyloxy]-C-methyl-carbonimidoyl]-1-propyl-imidazo[4,5-c]pyridin-2-yl]-1,2,4-triazol-3-amine | 0.82 | 375 | A | |
| 183 | 2-[7-[(E)-N-[(E)-3-chloroallyloxy]-C-methyl-carbonimidoyl]-1-propyl-imidazo[4,5-c]pyridin-2-yl]-1,2,4-triazol-3-amine | 0.85 | 375 | A | |
| 184 | 2-[7-[(Z)-N-[(E)-3-chlorobut-2-enoxy]-C-methyl-carbonimidoyl]-1-propyl-imidazo[4,5-c]pyridin-2-yl]-1,2,4-triazol-3-amine | 0.88 | 389 | A | |
| 185 | 2-[7-[(E)-N-[(E)-3-chlorobut-2-enoxy]-C-methyl-carbonimidoyl]-1-propyl-imidazo[4,5-c]pyridin-2-yl]-1,2,4-triazol-3-amine | 0.90 | 389 | A | |
| 186 | 2-[7-[N-(3,3-dichloroallyloxy)-C-methyl-carbonimidoyl]-1-propyl-imidazo[4,5-c]pyridin-2-yl]-1,2,4-triazol-3-amine | 0.91 | 409 | A | |
| 187 | 2-[7-[(E)-N-(3,3-dichloroallyloxy)-C-methyl-carbonimidoyl]-1-propyl-imidazo[4,5-c]pyridin-2-yl]-1,2,4-triazol-3-amine | 0.93 | 409 | A | |
| 188 | 2-[7-[(Z)-C-methyl-N-(3-methylbut-2-enoxy)carbonimidoyl]-1-propyl-imidazo[4,5-c]pyridin-2-yl]-1,2,4-triazol-3-amine | 0.87 | 369 | A | |
| 189 | 2-[7-[(E)-C-methyl-N-(3-methylbut-2-enoxy)carbonimidoyl]-1-propyl-imidazo[4,5-c]pyridin-2-yl]-1,2,4-triazol-3-amine | 0.91 | 369 | A | |
| 190 | 2-(1,7-dipropylimidazo[4,5-c]pyridin-2-yl)-1,2,4-triazol-3-amine | 0.64 | 286 | A | |
| 191 | 2-(1-methyl-7-phenyl-imidazo[4,5-c]pyridin-2-yl)-1,2,4-triazol-3-amine | 0.19 | 292 | B | 215-217 |
| 192 | 2-[7-(2,4-dichlorophenyl)-1-methyl-imidazo[4,5-c]pyridin-2-yl]-1,2,4-triazol-3-amine | 0.29 | 360 | B | 240-242 |
| 193 | 2-(7-bromo-1-methyl-imidazo[4,5-c]pyridin-2-yl)-1,2,4-triazol-3-amine | 1.02 | 294 | B | 226-227 |
| 194 | N-[2-(7-bromo-1-methyl-imidazo[4,5-c]pyridin-2-yl)-1,2,4-triazol-3-yl]acetamide | 0.85 | 336 | B | 230-232 |
| 195 | N-[2-[1-ethyl-7-(o-tolyl)imidazo[4,5-c]pyridin-2-yl]-1,2,4-triazol-3-yl]acetamide | | | | 192-194 |
| 196 | 2-[7-(2-chlorophenyl)-1-methyl-imidazo[4,5-c]pyridin-2-yl]-1,2,4-triazol-3-amine | 0.25 | 326 | B | 216-218 |
| 197 | 2-[7-(2-fluorophenyl)-1-methyl-imidazo[4,5-c]pyridin-2-yl]-1,2,4-triazol-3-amine | 1.04 | 310 | B | |
| 198 | 2-[7-(1-ethoxyvinyl)-1-methyl-imidazo[4,5-c]pyridin-2-yl]-1,2,4-triazol-3-amine | 1.09 | 286 | B | 163-166 |
| 199 | 1-[2-(5-amino-1,2,4-triazol-1-yl)-1-methyl-imidazo[4,5-c]pyridin-7-yl]ethanone | 0.26/0.48 | 258 | B | 245-249 |
| 200 | 2-[7-[(E)-N-ethoxy-C-methyl-carbonimidoyl]-1-methyl-imidazo[4,5-c]pyridin-2-yl]-1,2,4-triazol-3-amine | 0.81/1.03 | 301 | B | |
| 201 | 2-[7-[(E)-N-methoxy-C-methyl-carbonimidoyl]-1-methyl-imidazo[4,5-c]pyridin-2-yl]-1,2,4-triazol-3-amine | 0.46 | 287 | B | |
| 202 | 2-[7-[(E)-N-tert-butoxy-C-methyl-carbonimidoyl]-1-methyl-imidazo[4,5-c]pyridin-2-yl]-1,2,4-triazol-3-amine | 1.37 | 329 | B | |
| 203 | 2-[7-[(E)-N-benzyloxy-C-methyl-carbonimidoyl]-1-methyl-imidazo[4,5-c]pyridin-2-yl]-1,2,4-triazol-3-amine | 1.41 | 363 | B | |
| 204 | 2-[1-methyl-7-[(E)-C-methyl-N-(p-tolylmethoxy)carbonimidoyl]imidazo[4,5-c]pyridin-2-yl]-1,2,4-triazol-3-amine | 1.47 | 377 | B | |
| 205 | 2-[1-ethyl-7-[(Z)-C-methyl-N-[[3-(trifluoromethyl)phenyl]methoxy]carbonimidoyl]imidazo[4,5-c]pyridin-2-yl]-1,2,4-triazol-3-amine | 0.94 | 445 | A | |
| 206 | 2-[1-ethyl-7-[(E)-C-methyl-N-[[3-(trifluoromethyl)phenyl]methoxy]carbonimidoyl]imidazo[4,5-c]pyridin-2-yl]-1,2,4-triazol-3-amine | 0.96 | 445 | A | |
| 207 | 2-[1-ethyl-7-[(Z)-C-methyl-N-[[2-(trifluoromethyl)phenyl]methoxy]carbonimidoyl]imidazo[4,5-c]pyridin-2-yl]-1,2,4-triazol-3-amine | 0.93 | 445 | A | |
| 208 | 2-[1-ethyl-7-[(E)-C-methyl-N-[[2-(trifluoromethyl)phenyl]methoxy]carbonimidoyl]imidazo[4,5-c]pyridin-2-yl]-1,2,4-triazol-3-amine | 0.96 | 445 | A | |
| 209 | 2-[1-ethyl-7-[(Z)-C-methyl-N-[[4-(trifluoromethyl)phenyl]methoxy]carbonimidoyl]imidazo[4,5-c]pyridin-2-yl]-1,2,4-triazol-3-amine | 0.94 | 445 | A | |
| 210 | 2-[1-ethyl-7-[(E)-C-methyl-N-[[4-(trifluoromethyl)phenyl]methoxy]carbonimidoyl]imidazo[4,5-c]pyridin-2-yl]-1,2,4-triazol-3-amine | 0.96 | 445 | A | |
| 211 | 2-[1-ethyl-7-[(Z)-N-[(3-methoxyphenyl)methoxy]-C-methyl-carbonimidoyl]imidazo[4,5-c]pyridin-2-yl]-1,2,4-triazol-3-amine | 0.83 | 407 | A | |
| 212 | 2-[1-ethyl-7-[(E)-N-[(3-methoxyphenyl)methoxy]-C-methyl-carbonimidoyl]imidazo[4,5-c]pyridin-2-yl]-1,2,4-triazol-3-amine | 0.86 | 407 | A | |
| 213 | 2-[1-ethyl-7-[(Z)-N-[(2-methoxyphenyl)methoxy]-C-methyl-carbonimidoyl]imidazo[4,5-c]pyridin-2-yl]-1,2,4-triazol-3-amine | 0.84 | 407 | A | |
| 214 | 2-[1-ethyl-7-[(E)-N-[(2-methoxyphenyl)methoxy]-C-methyl-carbonimidoyl]imidazo[4,5-c]pyridin-2-yl]-1,2,4-triazol-3-amine | 0.87 | 407 | A | |
| 215 | 2-[1-ethyl-7-[(Z)-N-[(4-methoxyphenyl)methoxy]-C-methyl-carbonimidoyl]imidazo[4,5-c]pyridin-2-yl]-1,2,4-triazol-3-amine | 0.83 | 407 | A | |
| 216 | 2-[1-ethyl-7-[(E)-N-[(4-methoxyphenyl)methoxy]-C-methyl-carbonimidoyl]imidazo[4,5-c]pyridin-2-yl]-1,2,4-triazol-3-amine | 0.86 | 407 | A | |
| 217 | 2-[7-[(Z)-N-[(3-chlorophenyl)methoxy]-C-methyl-carbonimidoyl]-1-ethyl-imidazo[4,5-c]pyridin-2-yl]-1,2,4-triazol-3-amine | 0.90 | 411 | A | |
| 218 | 2-[7-[(E)-N-[(3-chlorophenyl)methoxy]-C-methyl-carbonimidoyl]-1-ethyl-imidazo[4,5-c]pyridin-2-yl]-1,2,4-triazol-3-amine | 0.93 | 411 | A | |
| 219 | 2-[1-ethyl-7-[(Z)-N-[(3-fluorophenyl)methoxy]-C-methyl-carbonimidoyl]imidazo[4,5-c]pyridin-2-yl]-1,2,4-triazol-3-amine | 0.85 | 395 | A | |

TABLE 17-continued

Physical data of compounds of formula (I):

| Entry | IUPAC Names | RT (min) | [M + H]+ (measured) | Method | MP (° C.) |
|---|---|---|---|---|---|
| 220 | 2-[1-ethyl-7-[(E)-N-[(3-fluorophenyl)methoxy]-C-methyl-carbonimidoyl]imidazo[4,5-c]pyridin-2-yl]-1,2,4-triazol-3-amine | 0.87 | 395 | A | |
| 221 | 2-[7-[(Z)-N-[(2-chlorophenyl)methoxy]-C-methyl-carbonimidoyl]-1-methyl-imidazo[4,5-c]pyridin-2-yl]-1,2,4-triazol-3-amine | 0.79 | 397 | A | |
| 222 | 2-[7-[(E)-N-[(2-chlorophenyl)methoxy]-C-methyl-carbonimidoyl]-1-methyl-imidazo[4,5-c]pyridin-2-yl]-1,2,4-triazol-3-amine | 0.83 | 397 | A | |
| 223 | 2-[7-[(Z)-N-[(2-fluorophenyl)methoxy]-C-methyl-carbonimidoyl]-1-methyl-imidazo[4,5-c]pyridin-2-yl]-1,2,4-triazol-3-amine | 0.75 | 381 | A | |
| 224 | 2-[7-[(E)-N-[(2-fluorophenyl)methoxy]-C-methyl-carbonimidoyl]-1-methyl-imidazo[4,5-c]pyridin-2-yl]-1,2,4-triazol-3-amine | 0.78 | 381 | A | |
| 225 | 2-[7-[(Z)-N-[(Z)-3-chloroallyloxy]-C-methyl-carbonimidoyl]-1-methyl-imidazo[4,5-c]pyridin-2-yl]-1,2,4-triazol-3-amine | 0.68 | 347 | A | |
| 226 | 2-[7-[(E)-N-[(Z)-3-chloroallyloxy]-C-methyl-carbonimidoyl]-1-methyl-imidazo[4,5-c]pyridin-2-yl]-1,2,4-triazol-3-amine | 0.71 | 347 | A | |
| 227 | 2-[7-[(Z)-N-(2-chloroallyloxy)-C-methyl-carbonimidoyl]-1-methyl-imidazo[4,5-c]pyridin-2-yl]-1,2,4-triazol-3-amine | 0.67 | 347 | A | |
| 228 | 2-[7-[(E)-N-(2-chloroallyloxy)-C-methyl-carbonimidoyl]-1-methyl-imidazo[4,5-c]pyridin-2-yl]-1,2,4-triazol-3-amine | 0.71 | 347 | A | |
| 229 | 2-[7-[(Z)-N-[(E)-3-chlorobut-2-enoxy]-C-methyl-carbonimidoyl]-1-methyl-imidazo[4,5-c]pyridin-2-yl]-1,2,4-triazol-3-amine | 0.74 | 361 | A | |
| 230 | 2-[7-[(E)-N-[(E)-3-chlorobut-2-enoxy]-C-methyl-carbonimidoyl]-1-methyl-imidazo[4,5-c]pyridin-2-yl]-1,2,4-triazol-3-amine | 0.77 | 361 | A | |
| 231 | 2-[7-[(Z)-N-[(E)-but-2-enoxy]-C-methyl-carbonimidoyl]-1-propyl-imidazo[4,5-c]pyridin-2-yl]-1,2,4-triazol-3-amine | 0.83 | 355 | A | |
| 232 | 2-[7-[(E)-N-[(E)-but-2-enoxy]-C-methyl-carbonimidoyl]-1-propyl-imidazo[4,5-c]pyridin-2-yl]-1,2,4-triazol-3-amine | 0.86 | 355 | A | |
| 233 | 2-[7-[(Z)-C-methyl-N-(2-methylallyloxy)carbonimidoyl]-1-propyl-imidazo[4,5-c]pyridin-2-yl]-1,2,4-triazol-3-amine | 0.82 | 355 | A | |
| 234 | 2-[7-[(E)-C-methyl-N-(2-methylallyloxy)carbonimidoyl]-1-propyl-imidazo[4,5-c]pyridin-2-yl]-1,2,4-triazol-3-amine | 0.85 | 355 | A | |
| 235 | 2-(5-amino-1,2,4-triazol-1-yl)-1-ethyl-imidazo[4,5-c]pyridine-7-carbaldehyde | 0.54 | 258 | A | |
| 236 | 2-[7-[(Z)-N-benzyloxy-C-methyl-carbonimidoyl]-1-propyl-imidazo[4,5-c]pyridin-2-yl]-1,2,4-triazol-3-amine | 0.87 | 391 | A | |
| 237 | 2-[7-[(E)-N-benzyloxy-C-methyl-carbonimidoyl]-1-propyl-imidazo[4,5-c]pyridin-2-yl]-1,2,4-triazol-3-amine | 0.89 | 391 | A | |
| 238 | 2-(1-ethyl-7-isopropenyl-imidazo[4,5-c]pyridin-2-yl)-1,2,4-triazol-3-amine | 0.56 | 270 | A | |
| 239 | 2-[7-[(E)-[(Z)-3-chloroallyloxy]iminomethyl]-1-ethyl-imidazo[4,5-c]pyridin-2-yl]-1,2,4-triazol-3-amine | 0.78 | 347 | A | |
| 240 | 2-[7-(1,2-dimethylprop-1-enyl)-1-ethyl-imidazo[4,5-c]pyridin-2-yl]-1,2,4-triazol-3-amine | 0.69 | 298 | A | |
| 241 | 2-[7-[(E)-benzyloxyiminomethyl]-1-ethyl-imidazo[4,5-c]pyridin-2-yl]-1,2,4-triazol-3-amine | 0.85 | 363 | A | |
| 242 | 2-[1-ethyl-7-[(E)-(2-fluorophenyl)methoxyiminomethyl]imidazo[4,5-c]pyridin-2-yl]-1,2,4-triazol-3-amine | 0.86 | 381 | A | |
| 243 | 2-[7-[(E)-[(E)-3-chlorobut-2-enoxy]iminomethyl]-1-ethyl-imidazo[4,5-c]pyridin-2-yl]-1,2,4-triazol-3-amine | 0.86 | 361 | A | |
| 244 | 1-[2-(5-amino-1,2,4-triazol-1-yl)-1-propyl-imidazo[4,5-c]pyridin-7-yl]ethanone | 0.64 | 286 | A | |

LC-MS Methods Used
Method A
ZQ Mass Spectrometer from Waters (Single quadrupole mass spectrometer)
  Instrument Parameters:
  Ionisation method: Electrospray
  Polarity: positive and negative ions
  Capillary (kV) 3.00, Cone (V) 30.00, Extractor (V) 2.00, Source Temperature (° C.) 150, Desolvation Temperature (° C.) 250, Cone Gas Flow (L/Hr) 50, Desolvation Gas Flow (L/Hr) 400 Mass range: 100 to 900 Da
  HP 1100 HPLC from Agilent:
    Solvent degasser, binary pump, heated column compartment and diode-array detector.
  Column: Phenomenex Gemini C18, 3 µm, 30×3 mm
  Temperature: 60° C.
  DAD Wavelength range (nm): 210 to 500
  Solvent Gradient:

| Time | A % | B % | Flow (mL/min) |
|---|---|---|---|
| 0.00 | 100 | 0 | 1.700 |
| 2.00 | 0 | 100 | 1.700 |
| 2.80 | 0 | 100 | 1.700 |
| 2.90 | 100 | 0 | 1.700 |
| 3.00 | 100 | 0 | 1.700 |

A = water + 5% MeOH + 0.05% HCOOH
B = Acetonitrile + 0.05% HCOOH

Method B
Mass Spectrometer: 6410 Triple quadrupole Mass Spectrometer from Agilent Technologies
HPLC: Agilent 1200 Series HPLC
Ionisation method: Electrospray (ESI)
Polarity: positive and Negative Polarity Switch
Scan Type: MS2 Scan
Capillary (kV): 4.00
Fragmentor (V): 100.00
Gas Temperature (° C.): 350
Gas Flow (L/min): 11
Nebulizer Gas (psi): 35
Mass range: 110 to 1000 Da
DAD Wavelength range (nm): 190 to 400

Column: Waters Xterra MS C18
Column length: 30 mm
Internal diameter of column: 4.6 mm
Particle Size: 3.5μ
Temperature: Room Temperature
Gradient Conditions

| (Solvent A: Water, 0.1% formic acid and Solvent B: Acetonitrile, 0.1% formic acid) | | | |
|---|---|---|---|
| Time (minutes) | A (%) | B (%) | Flow rate (ml/min) |
| 0 | 90 | 10 | 1.8 |
| 2.0 | 0 | 100 | 1.8 |
| 3.0 | 0 | 100 | 1.8 |
| 3.2 | 90 | 10 | 1.8 |
| 4.0 | 90 | 10 | 1.8 |

Method U
ACQUITY SQD Mass Spectrometer from Waters (Single quadrupole mass spectrometer)
Instrument Parameters:
Ionisation method: Electrospray
Polarity: positive ions
Capillary (kV) 3.00, Cone (V) 20.00, Extractor (V) 3.00, Source Temperature (° C.) 150, Desolvation Temperature (° C.) 400, Cone Gas Flow (L/Hr) 60, Desolvation Gas Flow (L/Hr) 700
Mass range: 100 to 800 Da
Column: Waters ACQUITY UPLC HSS T3; Column length: 30 mm; Internal diameter of column: 2.1 mm; Particle Size: 1.8 micron
Temperature: 60° C.
DAD Wavelength range (nm): 210 to 400
Solvent Gradient:

| Time (min) | A (%) | B (%) | Flow (ml/min) |
|---|---|---|---|
| 0 | 100 | 0 | 0.75 |
| 2.5 | 0 | 100 | 0.75 |
| 2.8 | 0 | 100 | 0.75 |
| 3.0 | 100 | 0 | 0.75 |

Solvent A = Water/Methanol 9:1 + 0.1% formic acid
Solvent B = Acetonitrile + 0.1% formic acid Biological Examples

*Alternaria solani*/Tomato/Leaf Disc (Early Blight)

Tomato leaf disks cv. Baby were placed on agar in multiwell plates (24-well format) and sprayed with the formulated test compound diluted in water. The leaf disks were inoculated with a spore suspension of the fungus 2 days after application. The inoculated leaf disks were incubated at 23° C./21° C. (day/night) and 80% relative humidity (rh) under a light regime of 12/12 h (light/dark) in a climate cabinet and the activity of a compound was assessed as percent disease control compared to untreated when an appropriate level of disease damage appears on untreated check disk leaf disks (5-7 days after application). The following compounds gave at least 80% control of *Alternaria solani* at 200 ppm when compared to untreated control leaf disks under the same conditions, which show extensive disease development: 15, 55, 56, 67, 72, 147, 172

*Phytophthora infestans*/Tomato/Leaf Disc Preventative (Late Blight)

Tomato leaf disks were placed on water agar in multiwell plates (24-well format) and sprayed with the formulated test compound diluted in water at an application rate of 200 ppm. The leaf disks were inoculated with a spore suspension of the fungus 1 day after application. The inoculated leaf disks were incubated at 16° C. and 75% relative humidity under a light regime of 24 h darkness followed by 12/12 h (light/dark) in a climate cabinet and the activity of a compound was assessed as percent disease control compared to untreated when an appropriate level of disease damage appears in untreated check leaf disks (5-7 days after application). The following compounds gave at least 80% control of *Phytophthora infestans* at 200 ppm when compared to untreated control leaf disks under the same conditions, which show extensive disease development: 125, 153

*Plasmopara viticola*/Grape/Leaf Disc Preventative (Late Blight)

Grape vine leaf disks were placed on water agar in multiwell plates (24-well format) and sprayed with the formulated test compound diluted in water. The leaf disks were inoculated with a spore suspension of the fungus 1 day after application. The inoculated leaf disks were incubated at 19° C. and 80% relative humidity under a light regime of 12/12 h (light/dark) in a climate cabinet and the activity of a compound was assessed as percent disease control compared to untreated when an appropriate level of disease damage appears in untreated check leaf disks (6-8 days after application). The following compounds gave at least 80% control of *Plasmopara viticola* at 200 ppm when compared to untreated control leaf disks under the same conditions, which show extensive disease development: 19, 40, 45, 48, 79, 109, 118, 135, 137, 139, 144, 145, 146, 149, 151, 153, 154, 155, 156, 160, 161, 163, 165, 166, 169, 172, 174, 176, 178, 180, 182, 184

*Puccinia recondita* f. Sp. *Tritici*/Wheat/Leaf Disc Preventative (Brown Rust):

Wheat leaf segments cultivated variety (cv) Kanzler were placed on agar in 24-well plates and sprayed with formulated test compound diluted in water at an application rate of 200 ppm. The leaf disks were inoculated with a spore suspension of the fungus 1 day after application. The inoculated leaf segments were incubated at 19° C. and 75% relative humidity under a light regime of 12/12 h (light/dark) in a climate cabinet and the activity of a compound was assessed as percent disease control compared to untreated when an appropriate level of disease damage appears in untreated check leaf segments (7-9 days after application). The following compounds gave at least 80% control of *Puccinia recondita* f. sp. *Tritici* at 200 ppm when compared to untreated control leaf disks under the same conditions, which show extensive disease development: 2, 13, 15, 17, 19, 22, 23, 24, 28, 30, 33, 35, 36, 38, 41, 45, 47, 48, 54, 55, 56, 59, 61, 67, 68, 72, 73, 74, 75, 79, 80, 81, 82, 83, 85, 86, 87, 88, 89, 90, 91, 93, 94, 95, 96, 97, 98, 99, 100, 101, 102, 103, 109, 110, 121, 123, 134, 135, 137, 139, 140, 143, 144, 145, 146, 147, 149, 150, 151, 153, 154, 155, 156, 157, 160, 161, 162, 163, 165, 166, 167, 168, 169, 172, 173, 174, 178, 180, 181, 182, 183, 184, 187, 188, 189, 190

*Puccinia recondita* f. Sp. *Tritici*/Wheat/Leaf Disc Curative (Brown Rust):

Wheat leaf segments cv Kanzler were placed on agar in 24-well plates. The leaf segments were inoculated with a spore suspension of the fungus. The plates were stored in darkness at 19° C. and 75% relative humidity. The formulated test compound diluted in water was applied at an application rate of 200 ppm 1 day after inoculation. The leaf segments were incubated at 19° C. and 75% relative humidity under a light regime of 12/12 h (light/dark) in a climate cabinet and the activity of a compound is assessed as percent disease control compared to untreated when an appropriate level of disease damage appears in untreated check leaf segments (6-8 days after application). The following compounds gave at least 80% control of *Puccinia recondita* f. sp. *Tritici* at 200 ppm when compared to untreated control leaf disks under the same conditions, which show extensive disease development: 2, 13, 16, 23, 30, 61, 75, 89, 103, 173, 174

*Phaeosphaeria nodorum* (*Septoria nodorum*)/Wheat/Leaf Disc Preventative (Glume Blotch):

Wheat leaf segments cv Kanzler were placed on agar in a 24-well plate and sprayed with formulated test compound diluted in water at an application rate of 200 ppm. The leaf disks are inoculated with a spore suspension of the fungus 2 days after application. The inoculated test leaf disks are incubated at 20° C. and 75% relative humidity under a light regime of 12/12 h (light/dark) in a climate cabinet and the activity of a compound is assessed as percent disease control compared to untreated when an appropriate level of disease damage appears in untreated check leaf disks (5-7 days after application). The following compounds gave at least 80% control of *Phaeosphaeria nodorum* at 200 ppm when compared to untreated control leaf disks under the same conditions, which show extensive disease development: 13, 15, 19, 22, 23, 30, 33, 37, 38, 39, 45, 48, 55, 59, 61, 66, 67, 68, 72, 73, 74, 75, 76, 79, 80, 83, 86, 88, 89, 90, 93, 94, 96, 98, 100, 101, 102, 103, 118, 121, 123, 137, 143, 144, 145, 147, 149, 151, 153, 155, 156, 165, 171, 172, 173, 174, 176, 182, 184, 188, 190

*Pyrenophora Teres*/Barley/Leaf Disc Preventative (Net Blotch):

Barley leaf segments cv Hasso are placed on agar in a 24-well plate and sprayed with formulated test compound diluted in water at an application rate of 200 ppm. The leaf segments are inoculated with a spore suspension of the fungus two days after application of the test solution. The inoculated leaf segments are incubated at 20° C. and 65% relative humidity under a light regime of 12/12 h (light/dark) in a climate cabinet and the activity of a compound is assessed as disease control compared to untreated when an appropriate level of disease damage appears in untreated check leaf segments (5-7 days after application). The following compounds gave at least 80% control of *Pyrenophora teres* at 200 ppm when compared to untreated control leaf disks under the same conditions, which show extensive disease development: 1, 2, 5, 13, 14, 15, 16, 17, 19, 22, 23, 24, 28, 30, 31, 32, 33, 34, 35, 36, 37, 38, 39, 40, 41, 43, 45, 47, 48, 49, 51, 55, 56, 58, 59, 61, 63, 65, 66, 67, 68, 70, 72, 73, 74, 75, 76, 79, 80, 81, 82, 83, 84, 85, 86, 87, 88, 89, 90, 91, 92, 93, 94, 96, 97, 98, 99, 100, 101, 102, 103, 106, 108, 109, 110, 113, 114, 118, 119, 121, 123, 133, 134, 135, 136, 137, 138, 139, 140, 141, 142, 143, 144, 145, 146, 147, 148, 149, 150, 151, 152, 153, 154, 155, 156, 157, 160, 161, 163, 164, 165, 166, 167, 168, 169, 171, 172, 173, 174, 175, 176, 178, 180, 181, 182, 183, 184, 185, 188, 190

*Botryotinia Fuckeliana* (*Botrytis cinerea*)/Liquid Culture (Gray Mould):

Conidia of the fungus from cryogenic storage were directly mixed into nutrient broth (Vogels broth). After placing a DMSO solution of test compound into a 96-well microtiter plate at an application rate of 200 ppm, the nutrient broth containing the fungal spores was added. The test plates were incubated at 24° C. and the inhibition of growth was determined photometrically 3-4 days after application. The following compounds gave at least 80% control of *Botryotinia fuckeliana* at 20 ppm when compared to untreated control under the same conditions, which show extensive disease development: 1, 2, 13, 15, 16, 17, 19, 22, 23, 24, 25, 28, 29, 30, 31, 33, 34, 35, 37, 38, 39, 41, 43, 45, 46, 48, 49, 52, 54, 55, 56, 59, 61, 66, 67, 68, 72, 73, 74, 75, 76, 79, 80, 81, 82, 83, 84, 85, 86, 87, 88, 89, 90, 91, 92, 93, 94, 96, 97, 98, 99, 100, 101, 102, 103, 106, 109, 110, 118, 121, 123, 126, 133, 134, 135, 137, 138, 139, 140, 141, 143, 144, 145, 146, 147, 149, 150, 151, 153, 154, 155, 156, 161, 163, 165, 166, 169, 171, 172, 173, 174, 176, 177, 178, 179, 180, 181, 182, 183, 184, 185, 188, 190

*Glomerella lagenarium* (*Colletotrichum lagenarium*)/Liquid Culture (Anthracnose):

Conidia of the fungus from cryogenic storage were directly mixed into nutrient broth (PDB potato dextrose broth). After placing a DMSO solution of test compound into a 96-well microtiter plate at an application rate of 200 ppm, the nutrient broth containing the fungal spores was added. The test plates were incubated at 24° C. and the inhibition of growth is measured photometrically 3-4 days after application. The following compounds gave at least 80% control of *Glomerella lagenarium* at 20 ppm when compared to untreated control under the same conditions, which show extensive disease development: 3, 6, 7, 8, 13, 15, 19, 20, 22, 23, 24, 28, 30, 33, 35, 37, 38, 39, 48, 55, 59, 67, 74, 76, 79, 80, 85, 86, 88, 89, 90, 91, 93, 94, 96, 97, 98, 100, 101, 102, 103, 112, 118, 121, 123, 129, 131, 136, 137, 138, 139, 140, 141, 143, 144, 145, 146, 147, 148, 149, 150, 151, 152, 153, 154, 155, 156, 157, 161, 163, 165, 166, 169, 171, 172, 173, 174

*Mycosphaerella Arachidis* (*Cercospora arachidicola*)/Liquid Culture (Early Leaf Spot):

Conidia of the fungus from cryogenic storage were directly mixed into nutrient broth (PDB potato dextrose broth). After placing a DMSO solution of test compound into a 96-well microtiter plate at an application rate of 200 ppm, the nutrient broth containing the fungal spores was added. The test plates are incubated at 24° C. and the inhibition of growth was determined photometrically 4-5 days after application. The following compounds gave at least 80% control of *Mycosphaerella arachidis* at 20 ppm when compared to untreated control under the same conditions, which show extensive disease development: 13, 15, 22, 23, 33, 38, 39, 45, 48, 55, 67, 68, 72, 73, 74, 75, 79, 80, 86, 90, 93, 98, 101, 102, 106, 123, 133, 134, 139, 140, 141, 147, 149, 152, 153, 155, 161, 163, 173, 176, 178, 180, 182, 184

*Mycosphaerella graminicola* (*Septoria tritici*)/Liquid Culture (*Septoria* Blotch):

Conidia of the fungus from cryogenic storage were directly mixed into nutrient broth (PDB potato dextrose broth). After placing a DMSO solution of test compound into a 96-well microtiter plate at an application rate of 200 ppm, the nutrient broth containing the fungal spores was added. The test plates were incubated at 24° C. and the inhibition of growth was determined photometrically 4-5 days after application. The following compounds gave at least 80% control of *Mycosphaerella graminicola* at 20 ppm when compared to untreated control under the same conditions, which show extensive disease development: 1, 2, 13, 15, 17, 19, 21, 22, 23, 24, 25, 28, 29, 33, 34, 35, 36, 37, 38, 39, 40, 41, 43, 45, 46, 48, 49, 52, 54, 55, 56, 59, 61, 66, 67, 68, 70, 72, 73, 74, 75, 76, 79, 80, 81, 82, 83, 84, 85, 86, 87, 88, 89, 90, 91, 92, 93, 94, 95, 96, 97, 98, 99, 100, 101, 102, 103, 106, 108, 109, 110, 118, 119, 121, 123, 133, 134, 135, 137, 138, 139, 140, 141, 143, 144, 145, 146, 147, 148, 149, 150, 151, 152, 153, 154, 155, 156, 157, 160, 161, 162, 163, 164, 165, 166, 167, 168, 169, 171, 172, 173, 174, 176, 177, 178, 179, 180, 181, 182, 183, 184, 185, 187, 188, 189, 190

*Gaeumannomyces graminis*/Liquid Culture (Take-all of Cereals):

Mycelial fragments of the fungus from cryogenic storage were directly mixed into nutrient broth (PDB potato dextrose broth). After placing a DMSO solution of test compound into a 96-well microtiter plate at an application rate of 200 ppm, the nutrient broth Cp.33, containing the fungal spores is added. The test plates were incubated at 24° C. and the inhibition of growth was determined photometrically 4-5 days after application. The following compounds gave at least 80% control of *Gaeumannomyces graminis* at 20 ppm when compared to untreated control under the same conditions, which show extensive disease development: 1, 2, 5, 13, 14, 15, 16, 17, 19, 21, 22, 23, 24, 25, 29, 38, 39, 48, 55, 59, 66, 67, 68, 73, 74, 75, 76, 79, 80, 81, 82, 83, 84, 85, 86, 87, 88, 89, 90, 91, 92, 93, 94, 95, 96, 97, 98, 99, 100, 101, 102, 103, 106, 108, 109, 118, 121, 123, 127, 128, 133, 134, 135, 136, 137, 138, 139, 140, 141, 142, 153, 171, 172, 173, 174, 176, 178, 180, 181, 183, 184, 187, 188, 190

*Thanatephorus cucumeris* (*Rhizoctonia solani*)/Liquid Culture (Foot Rot, Damping-Off):

Mycelia fragments of a newly grown liquid culture of the fungus are directly mixed into nutrient broth (PDB potato dextrose broth). After placing a DMSO solution of the test compounds into a 96-well microtiter plate at an application rate of 200 ppm, the nutrient broth containing the fungal material was added. The test plates were incubated at 24° C. and the inhibition of growth was determined photometrically 3-4 days after application. The following compounds gave at least 80% control of *Thanatephorus cucumeris* at 20 ppm when compared to untreated control under the same conditions, which show extensive disease development: 1, 2, 13, 15, 16, 17, 19, 21, 22, 23, 24, 25, 28, 29, 30, 31, 32, 33, 34, 35, 36, 37, 38, 39, 40, 41, 43, 44, 45, 46, 47, 48, 49, 51, 52, 54, 55, 56, 58, 59, 61, 63, 65, 66, 67, 68, 71, 72, 73, 74, 75, 76, 79, 80, 81, 82, 83, 84, 85, 86, 87, 88, 89, 90, 91, 92, 93, 94, 95, 96, 97, 98, 99, 100, 101, 102, 103, 106, 108, 109, 110, 118, 119, 121, 123, 125, 128, 133, 134, 135, 137, 138, 139, 140, 141, 142, 143, 144, 145, 146, 147, 148, 149, 150, 151, 152, 153, 154, 155, 156, 157, 159, 160, 161, 162, 163, 164, 165, 166, 167, 168, 169, 171, 172, 173, 174, 176, 177, 178, 179, 180, 181, 182, 183, 184, 185, 187, 188, 189, 190

*Monographella nivalis* (*Microdochium nivale*)/Liquid Culture (Foot Rot Cereals):

Conidia of the fungus from cryogenic storage were directly mixed into nutrient broth (PDB potato dextrose broth). After placing a DMSO solution of test compound into a 96-well microtiter plate at an application rate of 200 ppm, the nutrient broth containing the fungal spores was added. The test plates were incubated at 24° C. and the inhibition of growth was determined photometrically 4-5 days after application. The following compounds gave at least 80% control of *Monographella nivalis* at 20 ppm when compared to untreated control under the same conditions, which show extensive disease development: 13, 15, 19, 22, 23, 24, 25, 33, 38, 39, 48, 55, 67, 73, 74, 75, 79, 80, 81, 86, 87, 88, 89, 90, 91, 93, 94, 95, 96, 97, 98, 100, 101, 102, 103, 106, 118, 123, 133, 134, 137, 138, 139, 144, 145, 147, 149, 150, 151, 153, 155, 156, 165, 171, 172, 173, 174, 176, 177, 178, 180, 181, 182, 183, 184, 185, 188, 189, 190

*Blumeria graminis* f. Sp. *Tritici* (*Erysiphe graminis* f. Sp. *Tritici*)/Wheat/Leaf Disc Preventative (Powdery Mildew on Wheat):

Wheat leaf segments cv. Kanzler were placed on agar in a 24-well plate and sprayed with the formulated test compound diluted in water at an application rate of 200 ppm. The leaf disks were inoculated by shaking powdery mildew infected plants above the test plates 1 day after application. The inoculated leaf disks were incubated at 20° C. and 60% relative humidity under a light regime of 24 h darkness followed by 12 h/12 h (dark/light) in a climate chamber and the activity of a compound was assessed as percent disease control compared to untreated when an appropriate level of disease damage appears on untreated check leaf segments (6-8 days after application). The following compounds gave at least 80% control of *Blumeria graminis* at 200 ppm when compared to untreated control leaf disks under the same conditions, which show extensive disease development: 2, 13, 23, 50, 59, 61, 67, 75, 85, 86, 89, 90, 93, 102, 103, 107, 134, 136, 137, 138, 139, 141, 145, 151, 153, 154, 163, 173, 174

*Pythium ultimum*/Liquid Culture (Seedling Damping Off)

Mycelia fragments and oospores of a newly grown liquid culture of the fungus were directly mixed into nutrient broth (potato dextrose broth). After placing a DMSO solution of test compound into a 96-well format microtiter plate at an application rate of 200 ppm, the nutrient broth containing the fungal mycelia/spore mixture was added. The test plates were incubated at 24° C. and the inhibition of growth was determined photometrically 2-3 days after application. The following compounds gave at least 80% control of *Pythium ultimum* at 20 ppm when compared to untreated control under the same conditions, which show extensive disease development: 6, 13, 19, 22, 23, 33, 38, 39, 55, 59, 67, 73, 79, 80, 85, 86, 89, 96, 101, 102, 106, 149, 172, 173, 174, 176, 180, 190

*Fusarium culmorum*/Liquid Culture (Head Blight):

Conidia of the fungus from cryogenic storage were directly mixed into nutrient broth (PDB potato dextrose broth). After placing a DMSO solution of test compound into a microtiter plate (96-well format), the nutrient broth containing the fungal spores was added. The test plates were incubated at 24° C. and the inhibition of growth was determined photometrically 3-4 days after application. The following compounds gave at least 80% control of *Fusarium culmorum* at 20 ppm when compared to untreated control under the same conditions, which show extensive disease development: 15, 23, 74, 79, 86, 88, 89, 90, 93, 96, 98, 100, 101, 102, 106, 123, 147, 149, 153, 176, 178, 180, 182, 184

*Gibberella zeae* (Head Blight/Spikelet):

*Fusarium graminearum*, syn. *Gibberella zeae*, (Head blight): Wheat spikelets were placed on agar in multiwell plates (24-well format) and sprayed with test solutions. After drying, the spikelets were inoculated with a spore suspension of the fungus. After appropriate incubation the activity of a compound was assessed 6 dpi (days after inoculation) as preventative fungicidal activity. The following compounds gave at least 80% control of *Gibberella zeae* at 20 ppm when compared to untreated control under the same conditions, which show extensive disease development: 2, 13, 23, 89, 90, 93, 98, 102, 149.

*Fusarium culmorum* (Head Blight/Spikelet):

*Fusarium culmorum* (Head blight): Wheat spikelets were placed on agar in multiwell plates (24-well format) and sprayed with test solutions. After drying, the spikelets were inoculated with a spore suspension of the fungus. After appropriate incubation the activity of a compound was assessed 6 dpi (days after inoculation) as preventative fungicidal activity. The following compounds gave at least 80% control of *Fusarium culmorum* at 20 ppm when compared to untreated control under the same conditions, which show extensive disease development: 2, 13, 79, 90, 93, 98, 102.

*Sclerotinia sclerotiorum* (Cottony Rot/White Mold):

Mycelia fragments of a newly grown liquid culture of the fungus were directly mixed into nutrient broth (PDB potato dextrose broth). After placing a (DMSO) solution of test compound into a microtiter plate (96-well format) the nutrient broth containing the fungal material was added. The test plates are incubated at 24° C. and the inhibition of growth was determined photometrically 3-4 days after application. The following compounds gave at least 80% control of *Sclerotinia sclerotiorum* at 20 ppm when compared to untreated control under the same conditions, which show extensive disease development: 15, 22, 23, 30, 33, 35, 38, 39, 41, 48, 66, 67, 68, 73, 74, 75, 79, 80, 84, 86, 88, 89, 90, 91, 93, 94, 96, 97, 98, 100, 101, 102, 106, 123, 137, 139, 143, 144, 145, 147, 149, 150, 151, 153, 154, 155, 156, 161, 165, 171, 172, 176, 178, 180, 181, 182, 184, 188, 190

The invention claimed is:

1. A compound of the formula (I):

(I)

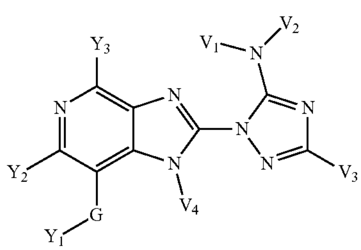

wherein $Y_1$ represents hydrogen, halogen, CN, $NO_2$, $C_1$-$C_6$ alkyl, $C_3$-$C_8$ cycloalkyl, $C_3$-$C_8$ cycloalkenyl, $C_2$-$C_6$ alkenyl, $C_2$-$C_6$ alkynyl, phenyl, naphthyl, a 5- to 10-membered mono- or bicyclic heterocycle containing one to three heteroatoms independently selected from O, S and N, providing that the heterocycle does not contain adjacent oxygen atoms, adjacent sulphur atoms, or adjacent sulphur and oxygen atoms, wherein the heterocycle can be aromatic, or fully or partially saturated, $OR^1$, $CO_2R^1$, $COR^2$, $CON(R^3)_2$, $N(R^3)_2$, $NR^3COR^2$ and $C(R^2)$═N—$OR^1$, wherein the alkyl, cycloalkyl, cycloalkenyl, alkenyl, alkynyl, phenyl, naphthyl, and heterocycle are optionally substituted by one or more groups independently selected from halogen, CN, OH, $NH_2$, $NR^3COR^2$, SH, $NO_2$, $OR^1$, $C_1$-$C_4$ alkyl, $C_1$-$C_4$ haloalkyl, phenyl, halophenyl, $C_1$-$C_4$ alkylphenyl, $C_3$-$C_8$ cycloalkyl, $C_3$-$C_8$ cycloalkenyl, $C_1$-$C_4$ alkylthio, alkylsulphinyl and $C_1$-$C_4$ alkylsulphonyl;

$Y_2$ and $Y_3$ are independently selected from hydrogen, halogen, CN, $NO_2$, $C_1$-$C_8$ alkyl, $C_3$-$C_8$ cycloalkyl, $C_3$-$C_8$ cycloalkenyl, $C_2$-$C_8$ alkenyl, $C_2$-$C_8$ alkynyl, phenyl, phenyl-$C_1$-$C_6$-alkyl, a 5- or 6-membered heterocycle containing one to three heteroatoms independently selected from O, S and N, providing that the heterocycle does not contain adjacent oxygen atoms, adjacent sulphur atoms, or adjacent sulphur and oxygen atoms, $OR^1$, $COR^2$, SH, $C_1$-$C_8$ alkylthio, $C_1$-$C_8$ alkylsulphinyl, $C_1$-$C_8$ alkylsulphonyl, phenylthio, phenylsulphinyl, phenylsulphonyl, $N(R^3)_2$, $CO_2R^1$, $O(CO)R^2$, $CON(R^3)_2$, $NR^3COR^2$ and $C(R^2)$═N—$OR^1$, wherein the alkyl, cycloalkyl, cycloalkenyl, alkenyl, alkynyl, phenyl, benzyl, and heterocycle are optionally substituted by one or more groups independently selected from halogen, CN, OH, $NH_2$, SH, $NO_2$, $OR^1$, $C_1$-$C_4$ alkyl, haloalkyl, alkylthio, alkylsulphinyl and $C_1$-$C_4$ alkylsulphonyl;

or $Y_3$ is defined as above and $Y_1$ and $Y_2$ together with the fragment of the compound to which they are attached form a partially or fully unsaturated 5- to 7-membered carbocyclic ring or a partially or fully unsaturated 5- to 7-membered heterocyclic ring containing one to three heteroatoms independently selected from O, S, N and $N(R^3)$, providing that the heterocycle does not contain adjacent oxygen atoms, adjacent sulphur atoms, or adjacent sulphur and oxygen atoms, and wherein the ring formed by $Y_1$ and $Y_2$ is optionally substituted by one or more groups independently selected from halogen, CN, $NH_2$, $NO_2$, OH, SH, $C_1$-$C_4$ alkyl, $C_1$-$C_4$ haloalkyl, $C_1$-$C_4$ alkoxy and $C_1$-$C_4$ haloalkoxy;

G represents a bond, O, S, S(O), $SO_2$, C(O), $CO_2$, $C(R^4)(R^5)$, $C(R^4)(R^5)$—$C(R^6)(R^7)$, $C(R^4)$═$C(R^5)$, C≡C, O—$C(R^4)(R^5)$, S—$C(R^4)(R^5)$, $C(R^4)(R^5)$—O, $C(R^4)(R^5)$—S or phenyl;

each $R^1$ is independently selected from hydrogen, $C_1$-$C_8$ alkyl, $C_3$-$C_8$ cycloalkyl, $C_3$-$C_8$ cycloalkyl-$C_1$-$C_2$ alkyl, $C_3$-$C_8$ cycloalkenyl, $C_3$-$C_8$ alkenyl, $C_3$-$C_8$ alkynyl, phenyl, benzyl or a 5- or 6-membered heterocycle containing one to three heteroatoms independently selected from O, S, N and $N(R^3)$, providing that the heterocycle does not contain adjacent oxygen atoms, adjacent sulphur atoms, or adjacent sulphur and oxygen atoms, wherein the alkyl, cycloalkyl, cycloalkenyl, alkenyl, alkynyl, phenyl, benzyl and heterocycle are optionally substituted by one or more groups independently selected from halogen, CN, OH, $NH_2$, $NO_2$, SH, $C_1$-$C_4$ alkyl, $C_1$-$C_4$ haloalkyl, $C_1$-$C_4$ alkoxy, $C_1$-$C_4$ haloalkoxy, $C_1$-$C_4$-alkoxy-$C_1$-$C_4$-alkyl and $C_1$-$C_4$ alkoxycarbonyl, and wherein the heterocycle may be attached to the rest of the molecule via a $C_1$-$C_2$ alkylene moiety;

each $R^2$ is independently selected from hydrogen, $C_1$-$C_8$ alkyl, $C_3$-$C_8$ cycloalkyl, $C_3$-$C_8$ cycloalkenyl, $C_2$-$C_8$ alkenyl, $C_2$-$C_8$ alkynyl, phenyl, benzyl and pyridyl, wherein the alkyl, cycloalkyl, cycloalkenyl, alkenyl, alkynyl, phenyl, benzyl and pyridyl groups are optionally substituted by one or more groups independently selected from halogen, CN, $NH_2$, $NO_2$, OH, $C_1$-$C_4$ alkyl, $C_1$-$C_4$ haloalkyl, $C_1$-$C_4$ alkoxy, $C_1$-$C_4$ alkylthio and $C_1$-$C_4$ haloalkoxy;

each $R^3$ is independently selected from hydrogen, $C_1$-$C_8$ alkyl, $C_3$-$C_8$ alkenyl, $C_3$-$C_8$ cycloalkyl, $C_3$-$C_8$ cycloalkenyl, $C_3$-$C_8$ alkynyl, phenyl, benzyl, CN, $OR^1$, $COR^2$, $C_1$-$C_8$ alkylsulphonyl, and a 5- or 6-membered heterocycle containing one to three heteroatoms independently selected from O, S, N and $N(R^8)$, providing that the heterocycle does not contain adjacent oxygen atoms, adjacent sulphur atoms, or adjacent sulphur and oxygen atoms, wherein the alkyl, cycloalkyl, cycloalkenyl, alkenyl, alkynyl, phenyl, benzyl and heterocycle are optionally substituted by one or more groups independently selected from halogen, CN, $NH_2$, $NO_2$, OH, $C_1$-$C_4$ alkyl, $C_1$-$C_4$-haloalkyl, $C_1$-$C_4$ alkoxy, $C_1$-$C_4$ haloalkoxy and $C_1$-$C_4$-alkoxy-$C_1$-$C_4$-alkyl;

wherein when two radicals $R^3$ are attached to the same nitrogen atom, these radicals can be identical or different;

wherein when two radicals $R^3$ are attached to the same nitrogen atom, both of these radicals cannot be $OR^1$;

and wherein when two radicals $R^3$ are attached to the same nitrogen atom, these two radicals together with the nitrogen atom to which they are attached may form a cycle selected from B-1, B-2, B-3, B-4, B-5, B-6, B-7 and B-8:

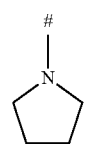

B-1

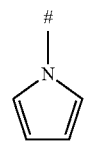

B-2

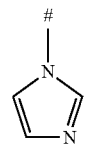

B-3

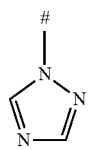

B-4

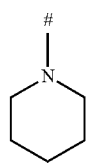

B-5

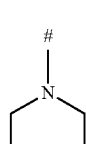

B-6

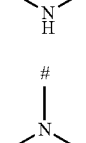

B-7

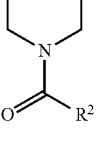

B-8

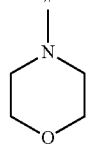

wherein the cycle formed is optionally substituted by one or more groups independently selected from halogen, CN, $NH_2$, $NO_2$, OH, $C_1$-$C_4$ alkyl, $C_1$-$C_4$ haloalkyl, $C_1$-$C_4$ alkoxy and $C_1$-$C_4$ haloalkoxy;

$R^4$, $R^5$, $R^6$ and $R^7$ independently of one another represent hydrogen, halogen, cyano, $C_1$-$C_4$ alkyl, $C_1$-$C_4$ alkoxy, $C_3$-$C_5$ cycloalkyl, $C_1$-$C_4$ haloalkyl, or $C_1$-$C_4$ alkylthio;

wherein two radicals $R^4$ and $R^5$ or $R^6$ and $R^7$ or $R^4$ and $R^6$ together with the carbon atom to which they are attached may form a 3- to 6-membered carbocycle or heterocycle containing one to three heteroatoms independently selected from O, S, N and $N(R^8)$, providing that the heterocycle does not contain adjacent oxygen atoms, adjacent sulphur atoms, or adjacent sulphur and oxygen atoms, wherein carbocycle and heterocycle are optionally substituted by one or more groups independently selected from halogen, CN, $NH_2$, $NO_2$, OH, $C_1$-$C_4$ alkyl, $C_1$-$C_4$-haloalkyl, $C_1$-$C_4$ alkoxy, $C_1$-$C_4$ haloalkoxy and $C_1$-$C_4$-alkoxy-$C_1$-$C_4$-alkyl;

$R^8$ represents hydrogen, $C_1$-$C_8$ alkyl, $C_1$-$C_8$ haloalkyl, $C_3$-$C_8$ cycloalkyl, $C_3$-$C_8$ alkenyl, $C_3$-$C_8$ alkynyl or $C_1$-$C_8$ alkoxy-$C_1$-$C_8$ alkyl;

$V_1$ and $V_2$ independently of one another represent hydrogen, $C_1$-$C_8$ alkyl, $C_3$-$C_8$ alkenyl, $C_3$-$C_8$ cycloalkyl, $C_3$-$C_8$ cycloalkenyl, $C_3$-$C_8$ alkynyl, benzyl, $C_2$-$C_9$ alkoxycarbonyl, $C_4$-$C_9$ alkenyloxycarbonyl, benzyloxycarbonyl or $COR^2$, wherein the alkyl, alkenyl, alkynyl, cycloalkyl, cycloalkenyl and benzyl are optionally substituted by one or more groups independently selected from halogen, CN, OH, $C_1$-$C_4$ alkyl, $C_1$-$C_4$ haloalkyl, $C_1$-$C_4$ alkoxy or $C_1$-$C_4$ haloalkoxy;

and wherein $V_1$ and $V_2$ together with the nitrogen atom to which they are attached may form a cycle selected from B-9, B-10, B-11, B-12 and B-13:

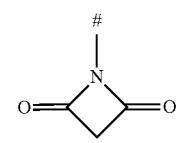

B-9

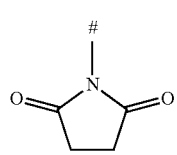

B-10

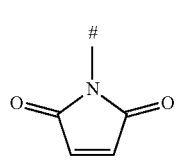

B-11

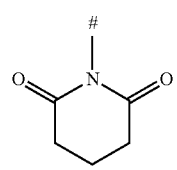

B-12

B-13

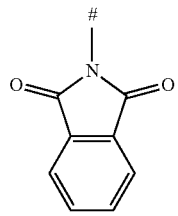

wherein the cycle so formed is optionally substituted by one or more groups independently selected from halogen, CN, $NH_2$, OH, $C_1$-$C_4$ alkyl, $C_1$-$C_4$ haloalkyl, $C_1$-$C_4$ alkoxy and $C_1$-$C_4$ haloalkoxy;

$V_3$ is selected from hydrogen, halogen, CN, $NO_2$, $C_1$-$C_8$ alkyl, $C_3$-$C_8$ cycloalkyl, $C_3$-$C_8$ cycloalkenyl, $C_2$-$C_8$ alkenyl, $C_2$-$C_8$ alkynyl, phenyl, benzyl, a 5- or 6-membered heterocycle containing one to three heteroatoms independently selected from O, S, N and $N(R^3)$, providing that the heterocycle does not contain adjacent oxygen atoms, adjacent sulphur atoms, or adjacent sulphur and oxygen atoms, $OR^1$, $COR^2$, SH, $C_1$-$C_8$ alkylthio, $C_1$-$C_8$ alkylsulphinyl, $C_1$-$C_8$ alkylsulphonyl, phenylthio, phenylsulphinyl, phenylsulphonyl, $N(R^3)_2$, $CO_2R^1$, $O(CO)R^2$, $CON(R^3)_2$, $NR^3COR^2$ and $C(R^2)$=N—$OR^1$, wherein the alkyl, cycloalkyl, cycloalkenyl, alkenyl, alkynyl, phenyl, benzyl, and heterocycle are optionally substituted by one or more groups independently selected from halogen, CN, $NH_2$, SH, $NO_2$, $OR^1$, $C_1$-$C_4$ alkyl and $C_1$-$C_4$ haloalkyl;

$V_4$ is selected from hydrogen, OH, $C_1$-$C_8$ alkyl, $C_1$-$C_8$ alkoxy, $C_3$-$C_8$ alkenyl, $C_3$-$C_8$ alkenyloxy, $C_3$-$C_8$ cycloalkyl, $C_3$-$C_8$ cycloalkenyl, $C_3$-$C_8$ cycloalkoxy, $C_3$-$C_8$ alkynyl, $C_3$-$C_8$ alkynyloxy, phenyl, phenyl-$C_1$-$C_6$-alkyl, benzyloxy, pyridyl, pyridyl-$C_1$-$C_6$-alkyl, $COR^2$, $CO_2R^2$, $CON(R^3)_2$ and $SO_2$—$C_1$-$C_8$-alkyl, wherein the alkyl, alkenyl, alkynyl, cycloalkyl, cycloalkenyl, phenyl, benzyl and pyridyl are optionally substituted by one or more groups independently selected from halogen, CN, $NH_2$, $NO_2$, OH, $C_1$-$C_4$ alkyl, $C_1$-$C_4$ haloalkyl, $C_1$-$C_4$ alkoxy and $C_1$-$C_4$ haloalkoxy;

or an agriculturally acceptable tautomer, salt or N-oxide thereof.

2. A compound according to claim 1 wherein $Y_1$ represents hydrogen, halogen, CN, $C_1$-$C_6$ alkyl, $C_3$-$C_8$ cycloalkenyl, $C_2$-$C_6$ alkenyl, $C_2$-$C_6$ alkynyl, phenyl, a 5- to 10-membered mono- or bicyclic heterocycle containing one or two heteroatoms independently selected from O, S and N, providing that the heterocycle does not contain adjacent oxygen atoms, adjacent sulphur atoms, or adjacent sulphur and oxygen atoms, wherein the heterocycle can be aromatic, or fully or partially saturated, $C_1$-$C_4$ alkoxy, $C_1$-$C_4$ alkoxycarbonyl, $C_1$-$C_4$ alkylcarbonyl, $C_1$-$C_4$ alkenylcarbonyl and $C(R^2)$=N—$OR^1$, wherein the alkyl, cycloalkenyl, alkenyl, alkynyl, phenyl, benzyl and heterocycle are optionally substituted by one or more groups independently selected from halogen, $NH_2$, NHCO($C_1$-$C_4$ alkyl), $C_1$-$C_4$ alkoxy, $C_1$-$C_4$ alkyl, $C_1$-$C_4$ haloalkyl, phenyl, halophenyl, $C_1$-$C_4$ alkylphenyl and $C_3$-$C_6$ cycloalkyl.

3. A compound according to claim 1, wherein $Y_2$ and $Y_3$ are independently selected from hydrogen, halogen, CN, methyl, ethyl, ethynyl, halomethyl, haloethyl, methoxy, halomethoxy, amino, methylamino, dimethylamino, pyrrolidino, piperidino, morpholino, methylthio, halomethylthio, methyl sulfinyl and methyl sulfonyl.

4. A compound according to claim 1, wherein G represents a direct bond, C(O), $C(R^4)(R^5)$, $C(R^4)(R^5)$—$C(R^6)/R^7)$ or $C(R^4)$=$C(R^5)$.

5. A compound according to claim 1, wherein
$V_1$ and $V_2$ are independently selected from hydrogen, $C_1$-$C_8$ alkyl, $C_3$-$C_8$ alkenyl, $C_3$-$C_8$ cycloalkyl, $C_3$-$C_8$ cycloalkenyl, $C_3$-$C_8$ alkynyl, benzyl, and $COR^2$, wherein the alkyl, alkenyl, alkynyl, cycloalkyl, cycloalkenyl and benzyl are optionally substituted by one or more halogen, CN, OH, $C_1$-$C_4$ alkyl, $C_1$-$C_4$ haloalkyl, $C_1$-$C_4$ alkoxy and $C_1$-$C_4$ haloalkoxy, or $V_1$ and $V_2$ together with the nitrogen atom to which they are attached may form the cycle B-10.

6. A compound according to claim 1, wherein
$V_3$ is selected from hydrogen, halogen, $NH_2$, $C_1$-$C_8$ alkyl, $C_3$-$C_8$ cycloalkyl, $C_3$-$C_8$ cycloalkenyl, $C_2$-$C_8$ alkenyl, $C_2$-$C_8$ alkynyl, phenyl and benzyl wherein the alkyl, cycloalkyl, cycloalkenyl, alkenyl, alkynyl, phenyl and benzyl, are optionally substituted by one or more groups independently selected from halogen, CN, $NH_2$, $NO_2$, $OR^1$, $C_1$-$C_4$ alkyl and $C_1$-$C_4$ haloalkyl.

7. A compound according to claim 1, wherein
$V_4$ is selected from hydrogen, $C_1$-$C_8$ alkyl, $C_3$-$C_8$ alkenyl, $C_3$-$C_8$ cycloalkyl, $C_3$-$C_8$ cycloalkenyl, $C_3$-$C_8$ alkynyl, phenyl, phenyl-$C_1$-$C_6$-alkyl, pyridyl, pyridyl-$C_1$-$C_6$-alkyl, $COR^2$, $CO_2R^2$, $CON(R^3)_2$ and $SO_2$—$C_1$-$C_8$-alkyl, wherein the alkyl, alkenyl, alkynyl, cycloalkyl, cycloalkenyl, phenyl and pyridyl are optionally substituted by one or more groups independently selected from halogen, CN, $NH_2$, $NO_2$, OH, $C_1$-$C_4$ alkyl, $C_1$-$C_4$ haloalkyl, $C_1$-$C_4$ alkoxy and $C_1$-$C_4$ haloalkoxy.

8. A compound according to claim 1, wherein
$V_4$ is selected from hydrogen, $C_1$-$C_4$ alkyl, $C_1$-$C_4$ haloalkyl, $C_3$-$C_4$ alkenyl, phenyl-$C_1$-$C_2$-alkyl or $C_3$-$C_8$ cycloalkyl.

9. A compound according to claim 1, wherein
$Y_1$ represents hydrogen, halogen, CN, $C_1$-$C_6$ alkyl, $C_3$-$C_8$ cycloalkenyl, $C_2$-$C_6$ alkenyl, $C_2$-$C_6$ alkynyl, phenyl, a 5- to 10-membered mono- or bicyclic heterocycle containing one or two heteroatoms independently selected from O, S and N, providing that the heterocycle does not contain adjacent oxygen atoms, adjacent sulphur atoms, or adjacent sulphur and oxygen atoms, wherein the heterocycle can be aromatic, or fully or partially saturated, $C_1$-$C_4$ alkoxy, $C_1$-$C_4$ alkoxycarbonyl, $C_1$-$C_4$ alkylcarbonyl, alkenylcarbonyl and $C(R^2)$=N—$OR^1$, wherein the alkyl, cycloalkenyl, alkenyl, alkynyl, phenyl, benzyl and heterocycle are optionally substituted by one or more groups independently selected from halogen, $NH_2$, NHCO($C_1$-$C_4$ alkyl), $C_1$-$C_4$ alkoxy, $C_1$-$C_4$ alkyl, $C_1$-$C_4$ haloalkyl, phenyl, halophenyl, alkylphenyl and $C_3$-$C_6$ cycloalkyl;

$Y_2$ and $Y_3$ are independently selected from hydrogen and halogen;

each $R^1$ is independently selected from hydrogen, $C_1$-$C_8$ alkyl, $C_3$-$C_8$ cycloalkyl, $C_3$-$C_8$ cycloalkyl-$C_1$-$C_2$ alkyl, $C_3$-$C_8$ cycloalkenyl, $C_3$-$C_8$ alkenyl, $C_3$-$C_8$ alkynyl, phenyl, benzyl or a 5- or 6-membered heterocycle containing one to two heteroatoms independently selected from O, S and N, providing that the heterocycle does not contain adjacent oxygen atoms, adjacent sulphur atoms, or adjacent sulphur and oxygen atoms, wherein the alkyl, cycloalkyl, cycloalkenyl, alkenyl, alkynyl, phenyl, benzyl and heterocycle are optionally substituted by one or more groups independently selected from halogen, CN, OH, $NH_2$, $NO_2$, SH, $C_1$-$C_4$ alkyl, $C_1$-$C_4$ haloalkyl, $C_1$-$C_4$ alkoxy, $C_1$-$C_4$ haloalkoxy and $C_1$-$C_4$ alkoxycarbonyl, and wherein the heterocycle may be attached to the rest of the molecule via a $C_1$-$C_2$ alkylene moiety;

$R^2$ independently of one another represents hydrogen, $C_1$-$C_4$ alkyl or $C_1$-$C_4$ haloalkyl;

$V_1$ and $V_2$ are independently selected from hydrogen and $C_1$-$C_4$-alkylcarbonyl, or $V_1$ and $V_2$ together with the nitrogen atom to which they are attached may form the cycle B-10;

$V_3$ is selected from hydrogen, halogen, $C_1$-$C_6$ alkyl, $C_1$-$C_4$ haloalkyl, phenyl, benzyl, $C_3$-$C_8$ cycloalkyl, or amino;

$V_4$ is selected from hydrogen, $C_1$-$C_4$ alkyl, $C_1$-$C_4$ haloalkyl, $C_3$-$C_4$ alkenyl, phenyl-$C_1$-$C_2$-alkyl or $C_3$-$C_8$ cycloalkyl;

G represents a direct bond, C(O), $C(R^4)(R^5)$, $C(R^4)(R^5)$—$C(R^6)(R^7)$ or $C(R^4)$=$C(R^5)$.

10. A compound according to claim 1, wherein $V_1$ is hydrogen.

11. A compound according to claim 1, wherein $V_1$ is hydrogen and $V_2$ is selected from hydrogen and $C_1$-$C_4$-alkylcarbonyl.

12. A compound according to claim 1, wherein $V_3$ is selected from hydrogen, halogen, $C_1$-$C_6$ alkyl, $C_1$-$C_4$ haloalkyl, phenyl, benzyl, cyclopropyl or amino.

13. A compound according to claim 1, wherein $Y_1$ represents hydrogen, halogen, CN, $C_1$-$C_6$ alkyl, $C_3$-$C_8$ cycloalkenyl, $C_2$-$C_6$ alkenyl, $C_2$-$C_6$ alkynyl, phenyl, a 5- to 10-membered mono- or bicyclic heterocycle containing one or two heteroatoms independently selected from O, S and N, providing that the heterocycle does not contain adjacent oxygen atoms, adjacent sulphur atoms, or adjacent sulphur and oxygen atoms, wherein the heterocycle can be aromatic, or fully or partially saturated, $C_1$-$C_4$ alkoxy, $C_1$-$C_4$ alkoxycarbonyl, $C_1$-$C_4$ alkenylcarbonyl and $C(R^2)$=N—$OR^1$, wherein the alkyl, cycloalkenyl, alkenyl, alkynyl, phenyl, benzyl and heterocycle are optionally substituted by one or more groups independently selected from halogen, $NH_2$, $NHCO(C_1$-$C_4$ alkyl), $C_1$-$C_4$ alkoxy, $C_1$-$C_4$ alkyl, $C_1$-$C_4$ haloalkyl, phenyl, halophenyl, $C_1$-$C_4$ alkylphenyl and $C_3$-$C_6$ cycloalkyl;

$Y_2$ and $Y_3$ are preferably independently selected from hydrogen and bromine;

G represents a direct bond, $C(R^4)(R^5)$, $C(R^4)(R^5)$—$C(R^6)(R^7)$ or $C(R^4)$=$C(R^5)$;

each $R^1$ is independently selected from hydrogen, $C_1$-$C_8$ alkyl, $C_3$-$C_6$ cycloalkyl-$C_1$-$C_2$ alkyl, $C_3$-$C_6$ alkenyl, phenyl, benzyl, pyridyl or pyridyl-$C_1$-$C_2$ alkyl wherein the alkyl, cycloalkyl, alkenyl, phenyl, benzyl and pyridyl are optionally substituted by one or more groups independently selected from halogen, CN, OH, $NH_2$, $NO_2$, SH, $C_1$-$C_4$ alkyl, $C_1$-$C_4$ haloalkyl, $C_1$-$C_4$ alkoxy, $C_1$-$C_4$ haloalkoxy and $C_1$-$C_4$ alkoxycarbonyl;

each $R^2$ independently of one another represents hydrogen, $C_1$-$C_4$ alkyl or $C_1$-$C_4$ haloalkyl;

$V_1$ is hydrogen;

$V_2$ is selected from hydrogen and $C_1$-$C_4$-alkylcarbonyl;

or $V_1$ and $V_2$ together with the nitrogen atom to which they are attached may form the cycle B-10;

$V_3$ is selected from hydrogen, halogen, $C_1$-$C_6$ alkyl, $C_1$-$C_4$ haloalkyl or cyclopropyl;

$V_4$ is selected from hydrogen, $C_1$-$C_4$ alkyl, $C_1$-$C_4$ haloalkyl, $C_3$-$C_4$ alkenyl, phenyl-$C_1$-$C_2$-alkyl, cyclopropyl, cyclopentyl or cyclohexyl.

14. A compound according to claim 1 wherein $V_4$ is hydrogen, $C_1$-$C_4$ alkyl, $C_3$-$C_4$ alkenyl, phenyl-$C_1$-$C_2$-alkyl, cyclopropyl, cyclopentyl or cyclohexyl.

15. A compound according to claim 1 wherein $V_1$ and $V_2$ are both hydrogen.

16. An agrochemical composition for controlling microorganisms or for infestation of plants therewith, wherein the active ingredient is a compound of the formula (I) as claimed in claim 1, together with a suitable carrier, and, optionally, further comprising an adjuvant.

17. A method of controlling infestation of cultivated plants by phytopathogenic microorganisms by application of a compound of formula (I) as claimed in claim 1 to plants, to parts of plants or to the locus thereof.

18. The method of claim 17 wherein the microorganisms are fungal organisms.

* * * * *